United States Patent
Barbosa et al.

(10) Patent No.: US 9,624,238 B2
(45) Date of Patent: Apr. 18, 2017

(54) 4H-THIENO[3,2-C]CHROMENE-BASED INHIBITORS OF NOTUM PECTINACETYLESTERASE AND METHODS OF THEIR USE

(71) Applicants: Joseph Barbosa, Lambertville, NJ (US); Kenneth Gordon Carson, Princeton, NJ (US); Michael Walter Gardyan, Feasterville, PA (US); Jason Patrick Healy, Flemington, NJ (US); Qiang Han, Plainsboro, NJ (US); Ross Mabon, Lambertville, NJ (US); Praveen Pabba, Pennington, NJ (US); James Tarver, Jr., Morrisville, PA (US); Kristen M. Terranova, Lawrenceville, NJ (US); Ashok Tunoori, Princeton, NJ (US); Xiaolian Xu, Princeton, NJ (US)

(72) Inventors: Joseph Barbosa, Lambertville, NJ (US); Kenneth Gordon Carson, Princeton, NJ (US); Michael Walter Gardyan, Feasterville, PA (US); Jason Patrick Healy, Flemington, NJ (US); Qiang Han, Plainsboro, NJ (US); Ross Mabon, Lambertville, NJ (US); Praveen Pabba, Pennington, NJ (US); James Tarver, Jr., Morrisville, PA (US); Kristen M. Terranova, Lawrenceville, NJ (US); Ashok Tunoori, Princeton, NJ (US); Xiaolian Xu, Princeton, NJ (US)

(73) Assignee: Lexicon Pharmaceuticals, Inc., The Woodlands, TX (US)

(*) Notice: Subject to any disclaimer, the term of this patent is extended or adjusted under 35 U.S.C. 154(b) by 0 days.

(21) Appl. No.: 14/284,106

(22) Filed: May 21, 2014

(65) Prior Publication Data
US 2014/0256784 A1    Sep. 11, 2014

Related U.S. Application Data

(63) Continuation of application No. 13/478,529, filed on May 23, 2012, now abandoned.
(60) Provisional application No. 61/490,839, filed on May 27, 2011.

(51) Int. Cl.
*C07D 333/52*    (2006.01)
*C07D 495/04*    (2006.01)

(52) U.S. Cl.
CPC ......... *C07D 495/04* (2013.01); *C07D 333/52* (2013.01)

(58) Field of Classification Search
CPC ........................... C07D 333/52; C07D 495/04
See application file for complete search history.

(56) References Cited

U.S. PATENT DOCUMENTS

| 2004/0082602 A1 | 4/2004 | Clare |
| 2006/0189678 A1 | 8/2006 | Taguchi et al. |
| 2009/0247567 A1 | 10/2009 | Do |
| 2012/0302562 A1* | 11/2012 | Barbosa ............... C07D 495/04 514/232.8 |

FOREIGN PATENT DOCUMENTS

| DE | 2628878 | 1/1978 |
| WO | WO 00/54789 | 9/2000 |

OTHER PUBLICATIONS

International Search Report for International Application No. PCT/US2012/039087 filed May 23, 2012.
Torisu, Y., et al., Cancer Sci., 99(6):1139-1146, 1143 (2008).
Guo, H., et al., J. Med. Chem., 53 (Feb. 25, 2010), pp. 1819-1829, 1819.
Allen, J.G. et al., J. Med. Chem., 53 (Jun. 10, 2010), pp. 4332-4353.
Hegab, M; Abdulla, M., Archiv der Pharmazie (Weinheim, Germany) (2006), 339(1), 41-47.
Pal, S.K., et al., J. Photochem. Photobiol. 174 (2005) 138-148.

* cited by examiner

*Primary Examiner* — Erich A Leeser
(74) *Attorney, Agent, or Firm* — Max Bachrach

(57) ABSTRACT

Compounds that may be used to inhibit Notum Pectinacetylesterase are described, as well as compositions comprising them, and methods of their use to treat diseases and disorders affecting bone.

13 Claims, 7 Drawing Sheets

4H-THIENO[3,2-C]CHROMENE-BASED INHIBITORS OF NOTUM PECTINACETYLESTERASE AND METHODS OF THEIR USE

This application claims priority to U.S. patent application Ser. No. 13/478,529, filed May 23, 2012, and provisional patent application No. 61/490,839, filed May 27, 2011, the entireties of which are incorporated herein by reference.

1. FIELD OF THE INVENTION

This invention relates small molecule inhibitors of Notum Pectinacetylesterase, compositions comprising them, and methods of their use.

2. BACKGROUND OF THE INVENTION

Bone health depends on the coordinated activities of bone forming osteoblasts and bone resorbing osteoclasts. "Bone turnover reflects a balance between these anabolic and catabolic cellular functions and ensures that the mature skeleton can repair itself when damaged and sustain its endocrine function by release of minerals such as calcium and phosphorous into the circulation." Allen, J. G. et al., *J. Med. Chem.*, 53 (Jun. 10, 2010), pp. 4332-4353, 4332. Many disease states alter this balance, resulting in increased or decreased bone mass or changes in bone quality. Gradual loss of bone mineral density is known as osteopenia; severe loss of bone is known as osteoporosis. Id.

The current standard of care for the treatment and prevention of osteoporosis utilizes the bisphosphonate class of oral, small molecule antiresportives. Id. at 4333. Zoledronic acid, raloxifene, calcium, and vitamin D supplements are also typically used in the osteoporosis treatment. Id. While antiresporptive agents can help prevent bone loss, anabolic agents "are capable of increasing bone mass to a greater degree . . . and also have the capacity to improve bone quality and increase bone strength." Guo, H., et al., *J. Med. Chem.*, 53 (Feb. 25, 2010), pp. 1819-1829, 1819. In the United States, human PTH is the only FDA-approved anabolic agent. Id.; Allen at 4333. "Because of the paucity of available anabolic agents for osteoporosis treatment, there is an urgent need to develop small molecular compounds to treat this disease that are nontoxic, cost-effective, and easy to administer." Guo, at 1819.

"Although the development of pharmacological agents that stimulate bone formation is less advanced compared to antiresporptive therapies, several pathways are known to facilitate osteoblast function." Allen at 4338. These pathways include bone morphogenic proteins, transforming growth factor β, parathyroid hormone, insulin-like growth factor, fibroblast growth factor, and wingless-type MMTV integration site (WNT) signaling. Id.Guo and coworkers recently reported results concerning the first of these pathways. Guo, supra. In particular, they reported that certain substituted benzothiophene and benzofuran compounds enhance bone morphogenic protein 2 expression in mice and rats. Two of the compounds reportedly stimulate bone formation and trabecular connectivity restoration in vivo. Id. at 1819.

Another of these pathways is the WNT pathway, which is implicated in a variety of developmental and regenerative processes. Allen at 4340. The pathway is complex, however, and much about it and about how its components affect bone remains unclear. For example, it has been suggested that LRP-5, mutations of which are associated with increased bone mass in humans, and β-catenin, through which canonical WNT signaling occurs, "may not be linked directly via WNT signaling to the control of bone mass." Id.

Recent analysis of gene expression data has led to the identification of new targets of WNT signaling. See, e.g., Torisu, Y., et al., *Cancer Sci.*, 99(6):1139-1146, 1143 (2008). One such target is Notum Pectinacetylesterase, also known as NOTUM and LOC (174111).

3. SUMMARY OF THE INVENTION

This invention encompasses compounds of the formula:

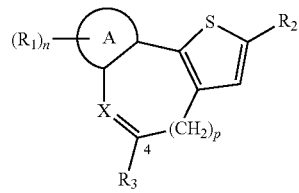

and pharmaceutically acceptable salt thereof, wherein: A is aryl or a 5- or 6-membered heterocycle; X is $C(R_4)_2$, $C(R_4)$, O, S, S(O), or $S(O)_2$; each $R_1$ is independently $R_{1A}$ or alkyl or heteroalkyl optionally substituted with one or more $R_{1A}$; each $R_{1A}$ is independently alkoxyl, amido, amino, carbamide, carboxyl, cyano, halo, hydroxyl, nitro, sulfanyl, sulfinyl, sulfonyl, or thio; n is 0-4; $R_2$ is $-C(O)R_{2A}$ or 5- or 6-membered cycloalkyl or heterocycle optionally substituted with one or more $R_{2B}$; $R_{2A}$ is $-OR_{2C}$, $-N(R_{2C})_2$, $-C(R_{2C})_2NO_2$, $-C(R_{2C})_2OR_{2C}$, $-C(R_{2C})_2CN$, or aryl or 5- or 6-membered heterocycle optionally substituted with one or more $R_{2B}$; each $R_{2B}$ is independently alkoxyl, amido, amino, carboxamide, carboxyl, cyano, halo, hydroxyl, nitro, sulfanyl, sulfinyl, sulfonyl, or thio; each $R_{2C}$ is independently hydrogen, alkyl, aryl, heteroalkyl, or 5- or 6-membered heterocycle; one of $R_3$ is $C_{1-2}$-alkyl or cycloalkyl, and the other $R_3$ is H or $C_{1-2}$-alkyl; p is 0-1; m is 0-2; and each $R_4$ is independently H, fluoro or $C_{1-2}$-alkyl. Particular compounds inhibit Notum Pectinacetylesterase ("NOTUM").

This invention also encompasses pharmaceutical compositions comprising the compounds disclosed herein, and methods of their use.

This invention further encompasses methods of inhibiting NOTUM, methods of stimulating endocortical bone formation, and methods of treating, managing, and preventing diseases and disorders associated with bone loss, such as osteoporosis.

4. BRIEF DESCRIPTION OF THE FIGURES

Certain aspects of the invention may be understood with reference to the attached figures.

FIG. 1 provides a graphical representation of differences between the cortical thicknesses of various bone sites in NOTUM homozygous knockout mice ("HOM") and those in their wildtype littermates ("WT").

FIG. 2 provides a graphical representation of an increase in cortical bone thicknesses observed in both NOTUM homozygous and heterozygous ("HET") knockout mice as compared to their wildtype littermates.

FIG. 3 provides a graphical representation of results obtained from femur breaking strength and spine compression tests performed on the bones of male NOTUM homozygous and heterozygous knockout mice and their wildtype littermates.

FIG. 4 provides a graphical representation of results obtained from femur breaking strength and spine compression tests performed on the bones of female NOTUM homozygous and heterozygous knockout mice and their wildtype littermates FIG. 5 shows the effects of administering 6,9-difluoro-4H-thieno[3,2-c]thiochromene-2-carboxylic acid on the midshaft femur cortical thickness of mice.

5. DETAILED DESCRIPTION OF THE INVENTION

Figure 1:
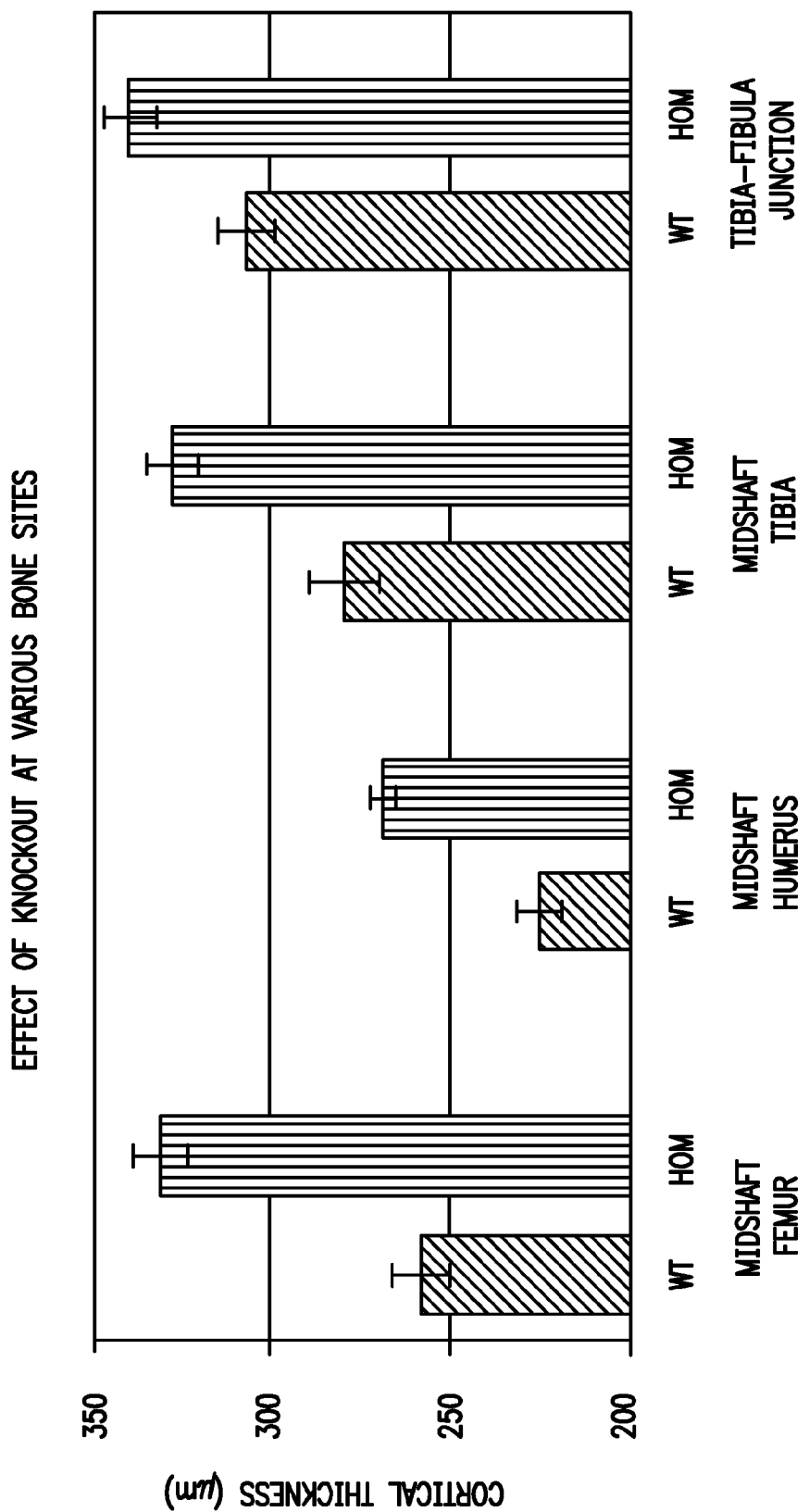

This invention is based, in part, on the discovery that inhibition of NOTUM can affect endocortical bone formation. Particular aspects of the invention are based on studies of mice lacking a functional NOTUM gene ("knockout mice"), on the discovery of compounds that inhibit NOTUM, and on the discovery that such compounds can be used to stimulate cortical bone formation in mice and rats.

5.1. Definitions

Unless otherwise indicated, the term "alkenyl" means a $C_{2-20}$ (e.g., $C_{2-10}$, $C_{2-4}$) straight chained, branched or cyclic hydrocarbon containing at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkyl" means a $C_{1-20}$ (e.g., $C_{1-10}$, $C_{1-4}$) straight chained, branched or cyclic hydrocarbon. $C_{1-4}$ alkyl moieties are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkoxy" means an —O-alkyl group. Examples of alkoxy groups include —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Unless otherwise indicated, the term "alkynyl" means a $C_{2-20}$ (e.g., $C_{2-10}$, $C_{2-4}$) straight chain, branched or cyclic hydrocarbon containing at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means a $C_{6-12}$ aromatic or partially aromatic ring or ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heterocycle" refers to 5-12-membered (e.g., 5,6-membered) monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "hydrogen" or "H" encompasses both hydrogen and deuterium. Thus, a generic (e.g., markush) chemical structure comprising hydrogen atoms is to be interpreted as encompassing their deuterated equivalents.

Unless otherwise indicated, the terms "manage," "managing" and "management" encompass preventing the recurrence of the specified disease or disorder, or of one or more of its symptoms, in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences*, 18th ed. (Mack Publishing, Easton Pa.: 1990) and *Remington: The Science and Practice of Pharmacy*, 19th ed. (Mack Publishing, Easton Pa.: 1995).

Unless otherwise indicated, the terms "prevent," "preventing" and "prevention" contemplate an action that occurs before a patient begins to suffer from the specified disease or disorder, which inhibits or reduces the severity of the disease or disorder, or of one or more of its symptoms. The terms encompass prophylaxis.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound is an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, CONH-alkyl, CONH-aryl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-). In a particular embodiment, the term substituted refers to a derivative of that structure or moiety wherein one or more of its hydrogen atoms is substituted with alcohol, alkoxy, alkyl (e.g., methyl, ethyl, propyl, t-butyl), amide (—C(O)NH-alkyl- or -alkyl-NHC(O)alkyl), amidinyl (—C(NH)NH-alkyl or —C(NR)NH$_2$), amine (primary, secondary and tertiary such as alkylamino, arylamino, arylalkylamino), aryl, carbamoyl (—NHC(O)O-alkyl- or —OC(O)NH-alkyl), carbamyl (e.g., CONH$_2$, as well as CONH-alkyl, CONH-aryl), halo, haloalkyl (e.g., —CCl$_3$, —CF$_3$, —C(CF$_3$)$_3$), heteroalkyl, imine (primary and secondary), isocyanate, isothiocyanate, thiol (e.g., sulfhydryl, thioether) or urea (—NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound is an amount of therapeutic agent, alone or in combination with other therapies, that provides a therapeutic benefit in the treatment or management of the disease or condition. The term "therapeutically effective amount" encompasses an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

Unless otherwise indicated, the term "include" has the same meaning as "include, but are not limited to" and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit. This invention encompasses tautomers and solvates (e.g., hydrates) of the compounds disclosed herein.

5.2. Compounds of the Invention

This invention encompasses compounds, and methods of using compounds, of the formula:

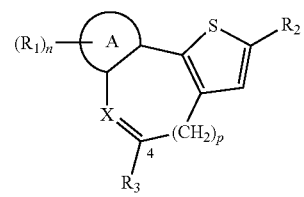

and pharmaceutically acceptable salts thereof, wherein: A is aryl or a 5- or 6-membered heterocycle; X is C(R$_4$)$_2$, C(R$_4$), O, S, S(O), or S(O)$_2$; each R$_1$ is independently R$_{1A}$ or alkyl or heteroalkyl optionally substituted with one or more R$_{1A}$; each R$_{1A}$ is independently alkoxyl, amido, amino, carbamide, carboxyl, cyano, halo, hydroxyl, nitro, sulfanyl, sulfinyl, sulfonyl, or thio; n is 0-4; $R_2$ is —C(O)$R_{2A}$ or a 5- or 6-membered cycloalkyl or heterocycle optionally substituted with one or more $R_{2B}$; $R_{2A}$ is —O$R_{2C}$, —N($R_{2C}$)$_2$, —C($R_{2C}$)$_2$NO$_2$, —C($R_{2C}$)$_2$O$R_{2C}$, —C($R_{2C}$)$_2$CN, or aryl or 5- or 6-membered heterocycle optionally substituted with one or more $R_{2B}$; each $R_{2B}$ is independently alkoxyl, amido, amino, carboxamide, carboxyl, cyano, halo, hydroxyl, nitro, sulfanyl, sulfinyl, sulfonyl, or thio; each $R_{2C}$ is independently hydrogen, alkyl, aryl, heteroalkyl, or 5- or 6-membered heterocycle; one of $R_3$ is $C_{1-2}$-alkyl or cycloalkyl, and the other $R_3$ is H or $C_{1-2}$-alkyl; p is 0-1; m is 0-2; and each $R_4$ is independently H, fluoro or $C_{1-2}$-alkyl. The bond drawn from X to $C_4$ can be single or double.

Certain compounds of the invention are of the formula:

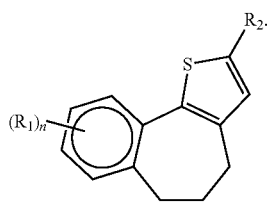

Others are of the formula:

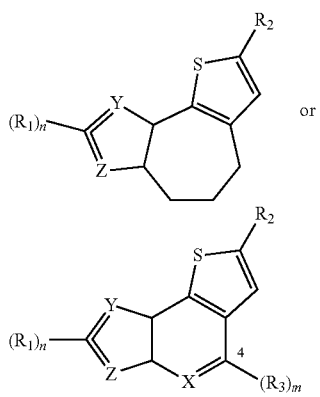

wherein X and Z are each independently CH, CH$_2$, N, NH, O, or S. In one embodiment of the invention, Y is S and Z is N or NH. In another, Y is CH and Z is O. In another, Y is S and Z is CH.

Particular embodiments of the invention encompass compounds of the formula:

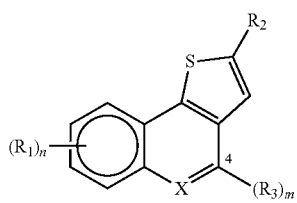

and pharmaceutically acceptable salts thereof, wherein: X is C($R_4$)$_2$, C($R_4$), O, S, S(O), or S(O)$_2$; each $R_1$ is independently $R_{1A}$ or alkyl or heteroalkyl optionally substituted with one or more $R_{1A}$; each $R_{1A}$ is independently alkoxyl, amido, amino, carbamide, carboxyl, cyano, halo, hydroxyl, nitro, sulfanyl, sulfinyl, sulfonyl, or thio; n is 0-4; $R_2$ is —C(O)$R_{2A}$ or a 5- or 6-membered cycloalkyl or heterocycle optionally substituted with one or more $R_{2B}$; $R_{2A}$ is —O$R_{2C}$, —N($R_{2C}$)$_2$, —C($R_{2C}$)$_2$NO$_2$, —C($R_{2C}$)$_2$O$R_{2C}$, —C($R_{2C}$)$_2$CN, or aryl or 5- or 6-membered heterocycle optionally substituted with one or more $R_{2B}$; each $R_{2B}$ is independently alkoxyl, amido, amino, carboxamide, carboxyl, cyano, halo, hydroxyl, nitro, sulfanyl, sulfinyl, sulfonyl, or thio; each $R_{2C}$ is independently hydrogen, alkyl, aryl, heteroalkyl, or 5- or 6-membered heterocycle; and one of $R_3$ is $C_{1-2}$-alkyl or cycloalkyl, and the other $R_3$ is H or $C_{1-2}$-alkyl; m is 0-2; and each $R_4$ is independently H, fluoro or $C_{1-2}$-alkyl; wherein the bond between X and $C_4$ is a double bond if X is C($R_4$).

In a particular embodiment, when X is CH$_2$, n is O, m is O, and $R_2$ is —C(O)$R_{2A}$, $R_{2A}$ is not —O$R_{2C}$ or —N($R_{2C}$)$_2$. In a particular embodiment, when X is O, n is O, m is O, and $R_2$ is —C(O)$R_{2A}$, $R_{2A}$ is not —O-alkyl. In a particular embodiment, when X is O, n is 1, $R_1$ is fluoro, m is O, and $R_2$ is —C(O)$R_{2A}$, $R_{2A}$ is not —O-alkyl. In a particular embodiment, when X is O, n is O, $R_3$ is not methyl.

In particular compounds, X is C($R_4$)$_2$. In some, at least one $R_4$ is H.

In particular compounds, the bond between X and $C_4$ is a single bond.

In particular compounds, X is O. In some, X is S, S(O), or S(O)$_2$.

In particular compounds, at least one $R_1$ is $R_{1A}$. In some, $R_{1A}$ is halo. In some, $R_{1A}$ is cyano. In some, $R_{1A}$ is nitro.

In particular compounds, $R_2$ is C(O)OH. In some, $R_2$ is optionally substituted 5- or 6-membered heterocycle.

In particular compounds, n is 2. In some, n is 3.

In particular compounds, m is 0 (i.e., one or two hydrogen atoms are bound to the $C_4$ carbon, depending on whether there is a double bond between it and X).

In particular compounds, m is 1 and $R_3$ is methyl.

Compounds of the invention can be prepared by methods known in the art and by methods described herein. For example, thieno[3,2-c]chromene carboxylic acids, dihydronaptho[1,2-b]thiophene-2-carboxylic acids, and thieno[3,2-c]thiochromene-2-carboxylic acid derivatives were synthesized from the corresponding substituted chroman-4-ones, dihydronaphthalen-1(2H)-ones and thiochroman-4-ones, as shown in Scheme 1.

Scheme 1

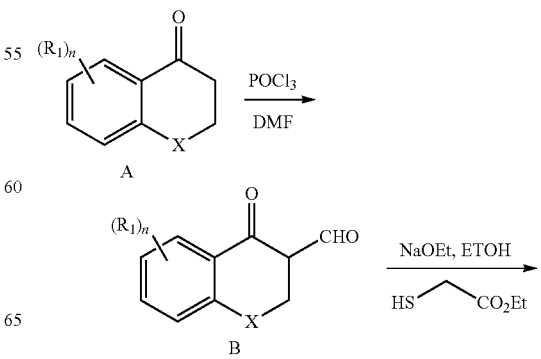

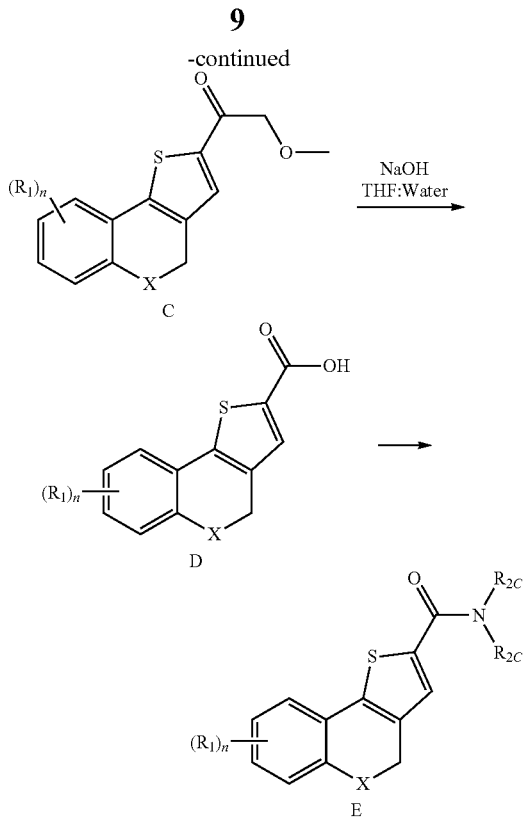

Commerically available or prepared ketones (A) were treated with phosphorus oxychloride and dimethylformamide under Vislmeier-Hack conditions to generate the α,β-unsaturated β-chloroaldehydes (B). Subsequent treatment with ethyl mercaptoacetate and sodium ethoxide effected cyclization to generate substituted thiophenes (C). Saponification of the esters with aqueous base yielded a range of carboxylic acids (D). These acids could be further functionalized to amides, heterocycles or ketoacids, as demonstrated herein.

5.3. Methods of Use

This invention encompasses methods of inhibiting NOTUM, which comprise contacting NOTUM with a compound of the invention (i.e., a compound disclosed herein).

This invention also encompasses a method of upregulating the WNT pathway, which comprises contacting NOTUM with a compound of the invention.

This invention encompasses a method of stimulating endocortical bone formation in a patient, which comprises administering to a patient in need thereof an effective amount of a compound of the invention. It also encompasses a method of increasing cortical bone thickness, comprising administering to a patient in need thereof an effective amount of a compound of the invention.

This invention encompasses a method of treating, managing, or preventing a disease or disorder associated with bone loss, which comprises administering to a patient in need thereof a therapeutically or prophylactically effective amount of a compound of the invention. Examples of diseases and disorders include osteoporosis (e.g., postmenopausal osteoporosis, steroid- or glucocorticoid-induced osteoporosis), osteopenia, and Paget's disease.

Also encompassed by the invention is a method of accelerating or facilitating bone healing in a patient, which comprises administering to a patient in need thereof a therapeutically or prophylactically effective amount of a compound of the invention.

This invention also encompasses a method of treating, managing, or preventing bone fractures, which comprises administering to a patient in need thereof a therapeutically or prophylactically effective amount of a compound of the invention. Particular bone fractures are associated with metastatic bone disease, i.e., cancer that has metastasized to bone. Examples of cancers that can metastasize to bone include prostate, breast, lung, thyroid, and kidney cancer.

This invention also encompasses a method of treating, managing, or preventing bone loss associated with, or caused by, a disease or disorder, which comprises administering to a patient in need thereof a therapeutically or prophylactically effective amount of a compound of the invention. Examples of diseases and disorders include celiac disease, Crohns Disease, Cushing's syndrome, hyperparathyroidism, inflammatory bowel disease, and ulcerative colitis.

Examples of patients that may benefit from methods of this invention include men and women aged 55 years or older, post-menopausal women, and patients suffering from renal insufficiency.

Compounds of the invention can be administered in combination (e.g., at the same or at different times) with other drugs known to be useful in the treatment, management, or prevention of diseases or conditions affecting the bone. Examples include: androgen receptor modulators; bisphosphonates; calcitonin; calcium sensing receptor antagonists; cathepsin K inhibitors; estrogen and estrogen receptor modulators; integrin binders, antibodies, and receptor antagonists; parathyroid hormone (PTH) and analogues and mimics thereof; and Vitamin D and synthetic Vitamin D analogues.

Examples of androgen receptor modulators include finasteride and other 5α-reductase inhibitors, nilutamide, flutamide, bicalutamide, liarozole, and abiraterone acetate.

Examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof.

Examples of cathepsin K inhibitors include VEL-0230, AAE581 (balicatib), MV061194, SB-462795 (relacatib), MK-0822 (odanacatib), and MK-1256.

Examples of estrogen and estrogen receptor modulators include naturally occurring estrogens (e.g., 7-estradiol, estrone, and estriol), conjugated estrogens (e.g., conjugated equine estrogens), oral contraceptives, sulfated estrogens, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

Examples of integrin binders, antibodies, and receptor antagonists include vitaxin (MEDI-522), cilengitide and L-000845704.

5.4. Pharmaceutical Formulations

This invention encompasses pharmaceutical compositions comprising one or more compounds of the invention, and optionally one or more other drugs, such as those described above.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed. (Mack Publishing, Easton Pa.: 1990).

Pharmaceutical compositions of this invention are preferably administered orally. Discrete dosage forms suitable for oral administration include tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., *Remington's Pharmaceutical Sciences,* 18th ed. (Mack Publishing, Easton Pa.: 1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or nonaqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

5.4.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

5.4.2. Parenteral Dosage Forms

Parenteral dosage forms can be administered to patients by various routes including subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

6. EXAMPLES

6.1. Knock-Out Mouse

Mice homozygous for a genetically engineered mutation in the murine ortholog of the human NOTUM gene were generated using corresponding mutated embryonic stem (ES) cell clones from the OMNIBANK collection of mutated murine ES cell clones (see generally, U.S. Pat. No. 6,080,576). In brief, ES cell clones containing a mutagenic viral insertion into the murine NOTUM locus were microinjected into blastocysts which were in turn implanted into pseudopregnant female hosts and carried to term. The resulting chimeric offspring were subsequently bred to C57 black 6 female mice and the offspring checked for the germline transmission of the knocked-out NOTUM allele. Animals heterozygous for the mutated NOTUM allele were subsequently bred to produce offspring that were homozygous for the mutated NOTUM allele, heterozygous for the mutated NOTUM allele, or wild type offspring at an approximate ratio of 1:2:1.

Mice homozygous (−/−) for the disruption of the NOTUM gene were studied in conjunction with mice heterozygous (+/−) for the disruption of the NOTUM gene and wild-type (+/+) litter mates. During this analysis, the mice were subject to a medical work-up using an integrated suite of medical diagnostic procedures designed to assess the function of the major organ systems in a mammalian subject. By studying the homozygous (−/−) "knockout" mice in the described numbers and in conjunction with heterozygous (+/−) and wild-type (+/+) litter mates, more reliable and repeatable data were obtained.

Figure 2:
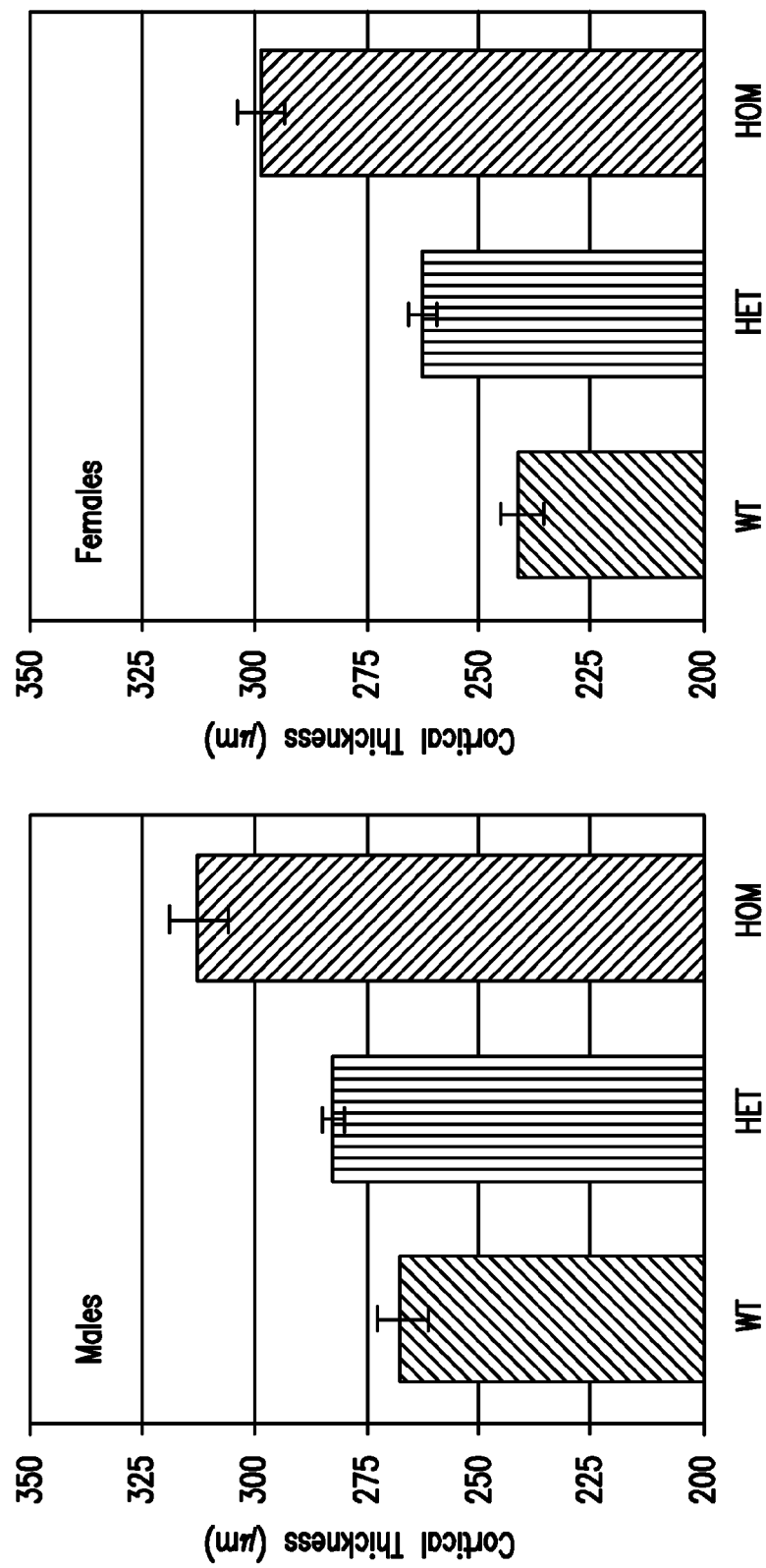

As shown in FIG. 1, male mice having homozygous disruption of the NOTUM gene ("homs") exhibited greater cortical thicknesses at various bone sites, compared to their wildtype littermates at 16 weeks of age (number of mice N=10 for both groups). These differences, which were measured by microCT (Scanco µCT40), were: 28% ($p<0.001$) at midshaft femur; 19% ($p<0.001$) at midshaft humerous; 17% ($p<0.001$) at midshaft tibia; and 11% ($p<0.001$) at tibia-fibula junction. As shown in FIG. 2, at 16 weeks of age, the midshaft femur cortical bone thickness of mice heterozygous for the NOTUM mutation ("hets") was also greater than that of their wildtype littermates: male hets (N=50) exhibited a 6% (p=0.007) increase compared to their wildtype littermates (N=23); and female hets (N=57) exhibited a 9% ($p<0.001$) increase compared to their wildtype littermates (N=22).

Figure 3:
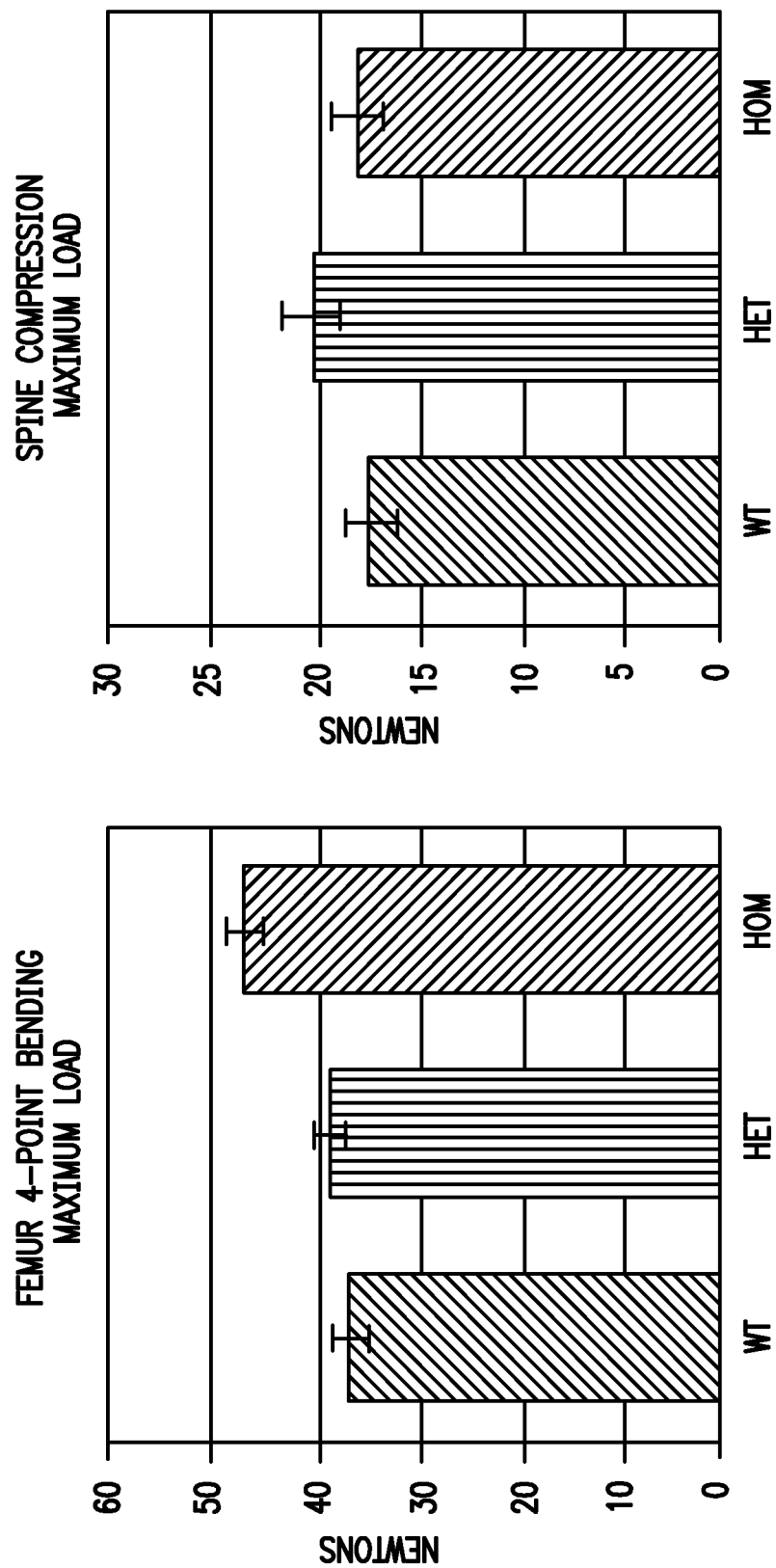
Figure 4:
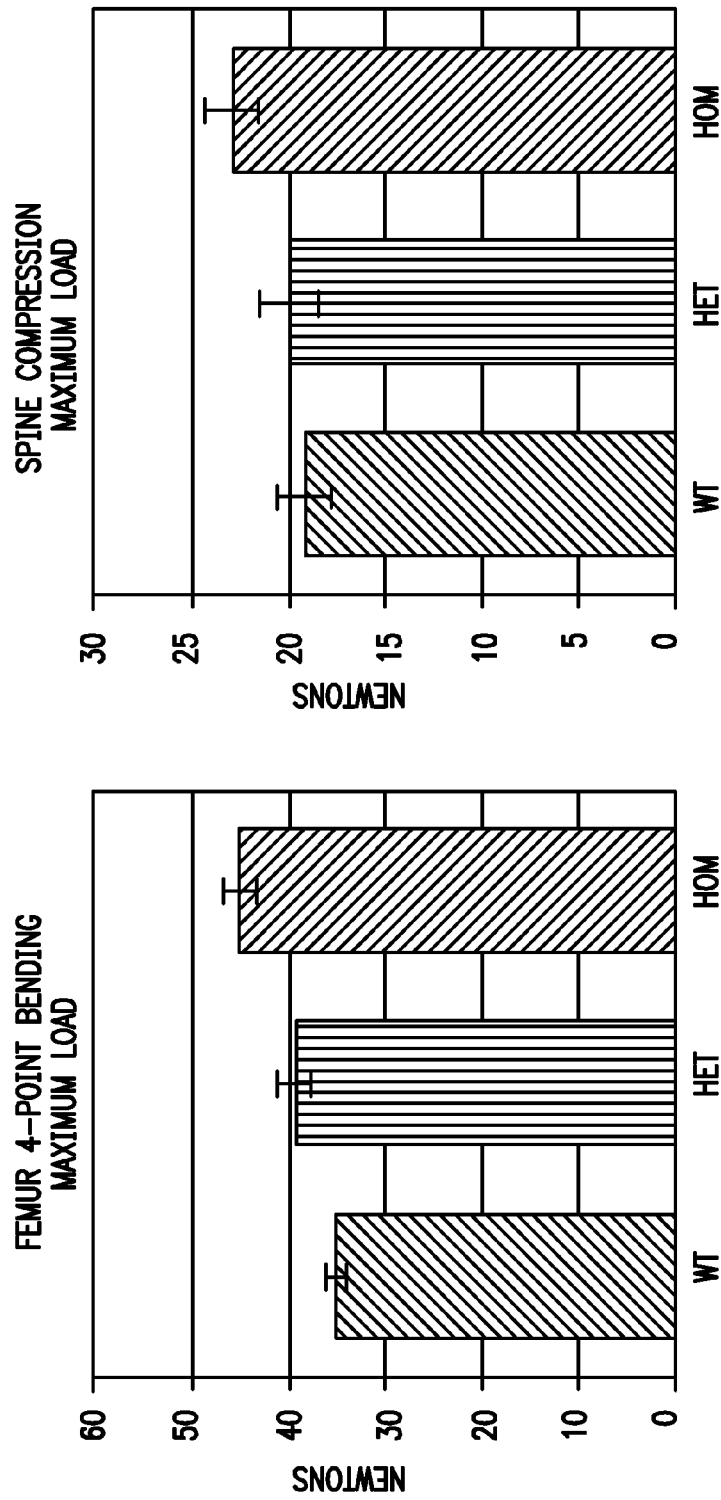

Practical manifestations of the observed redistribution of bone formation in NOTUM animals is reflected in FIGS. 3 and 4, which show results of femur breaking strength tests (performed by SkeleTech, now Ricerca Biosciences) using a standard 4-point bending test. As shown in FIG. 3, which provides results obtained for male mice at 16 weeks of age, hets (N=20) exhibited a 5% (p=0.54) increase in femur breaking strength compared to their wildtype littermates (N=23), whereas homs (N=17) exhibited a 28% ($p<0.001$) increase. On the other hand, spine compression tests of both NOTUM homs and hets did not show a significant reduction in maximum spine compression loads as compared to wild-type controls. Similar results were obtained for female mice at 16 weeks of age. As shown in FIG. 4, hets (N=20) exhibited a 12% (p=0.04) increase in femur breaking strength compared to their wildtype littermates (N=21), whereas homs (N=18) exhibited a 28% ($p<0.001$) increase. Analyzation of these and other data revealed a strong correlation between cortical thickness and femur breaking strength.

6.2. Reporter Assay

Compounds' $EC_{50}$ values were determined using this assay, which utilized conditioned media that was prepared as follows. Plasmid containing human notum pectinacetyltransferase in pcDNA3.1(+) vector was transfected into HEK (293 cells and clones were selecting by growing in presence of 400 ug/mL of G418. The clone containing highest expression of human notum pectinacetyltransferase in the conditioned media was maintained for all future activity assays. L cells overexpressing and secreting Wnt3a into the conditioned media were purchased from ATCC.

The assay protocol was as follows. Approximately 5 million CellSensor® LEF/TCF-blaFreeStyle™ 293F cells were grown to near confluency in 15-cm plates. The cell growth medium consisted of DMEM with 10% Dialyzed FBS, 5 µg/ml Blasticidin (Invitrogen, R210-01), 0.1 mM NEAA, 25 mM HEPES and 1×GPS. Cells were then trypsinized by first rinsing with PBS, followed by addition of 5 mL of trypsin and incubation of plates at room temperature for two minutes. A total of 10 mL of assay media (Opti-MEM, plus 0.5% dialyzed FBS, 0.1 mM NEAA, 1 mM sodium pyruvate, 10 mM HEPES, 1×GPS) was then added per 15 cm plate. Cells were counted and suspended at 0.75 million cells per mL. Cells were seeded into Biocoat 384-well plates (Fisher, Catalogue #356663) at a density of 15000 cells per 20 µL per well. After incubation of cells at 37° C. for 3 hours, 10 µL of 30 mM LiCl in assay medium was added per well, followed by incubation at 37° C. for another 3 hours. Meanwhile, compounds were acoustically pinged into Greiner 384-well plates (catalog #781076) using an ECHO, followed by addition of 10 µL per well of Wnt3a conditioned media and 10 µL per well of notum pectinacetylesterase-conditioned media. Ten µL of the Wnt3a/notum pentinacetyltransferase mixture was then transferred from Greiner plates to each well of the 384-well plates containing the CellSensor cells. After incubation of cells overnight at 37° C., reactions were developed by addition of 5 µL of 1×CCF4 (Invitrogen, Catalogue number K (1085) to each well, covering the entire 384-well plate, and gentle rocking in the dark at room temperature for 3 hours. Plates were then read on an Envision Plate Reader using an excitation wavelength of 400 nm and emission wavelengths of 460 nm and 535 nm.

6.3. Concanavalin A (ConA)-Induced Hepatitis Disease Model

This model was generally conducted as follows. C57Bl/6-Albino/129SvEv mice were injected intravenously (i/v) via the lateral tail vein with a single sublethal dose of Concanavalin A from *Canavalia ensiformis* (Jack bean, Type IV-S, lyophilized powder, aseptically processed; Sigma) administered at 10-16 mg/kg mouse body weight in a total volume of 0.1-0.3 ml of pyrogen-free PBS. The tail vein injections of mice restrained in a Plexiglas mouse restrainer were performed without anesthesia, using a 1 ml syringe with a 27 gauge needle. At six and 24 hr post-injection, blood samples were collected by retro-orbital bleeding. The animals were sacrificed and sera from the blood samples were analyzed for the presence of IL-12, TNF-α, MCP-1, IFN-γ, IL-10, and IL-6 using a mouse inflammation cytometric bead array (CBA) kit (BD Biosciences, Mountain View, Calif.), according to the manufacturer's instructions. Data were acquired with a FACSCalibur flow cytometer and analyzed with BD CBA Software (BD Biosciences). Biochemical markers of liver failure were assessed by measuring serum liver damage enzymes, aspartate aminotransferase (AST) and alanine aminotransferase (ALT), using a standard clinical biochemical analyzer. Livers of ConA-treated mice were sectioned and stained with H&E to evaluate the degree of T cell-mediated immune inflammation.

6.4. Binding Assay

Compounds' $IC_{50}$ values were determined using this assay, which utilized trisodium 8-octanoyloxypyrene-1,3,6- trisulfonate (OPTS), a water soluble enzyme substrate for fluorimetric assays of esterases and lipases. Plasmid containing human notum pectinacetyltransferase in pcDNA3.1 (+) vector was transfected into HEK (293 cells and clones were selecting by growing in presence of 400 ug/mL of G418. Condition media from these cells was used for the assay.

An ECHO was used to acoustically dispense 75 nL of compounds into dry Greiner 384-well plates (catalog #781076), followed by addition of 10 uL of 50 mM Tris/HCl (pH 6.8) to every well of these 384-well assay plates. Conditioned media containing human notum pectinacetyltransferase was diluted 75× with Assay Buffer (50 mM Tris, pH 6.8, 5 mM CaCl (2, 0.5 mM MgCl (2), and 25 μL of this "Enzyme Mix" was added to each well followed by a 10 minute pre-incubation. Enzyme reactions were initiated by addition of 15 μL OPTS substrate (Sigma, catalog #74875) to a final concentration of 5 μM and reaction times were for 10 minutes at room temperature. All plates were read on an Envision Plate Reader with an excitation wavelength of 485 nm and emission wavelength of 535 nm.

6.5. Synthetic Method A: Preparation of 8-chloro-6-fluoro-4H-thieno[3,2-c]chromene-2-carboxylic acid

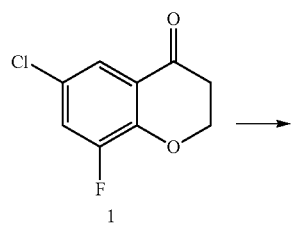

1

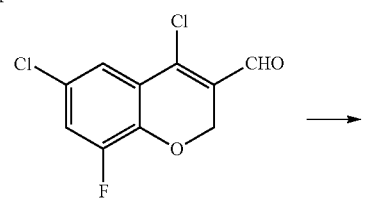

2

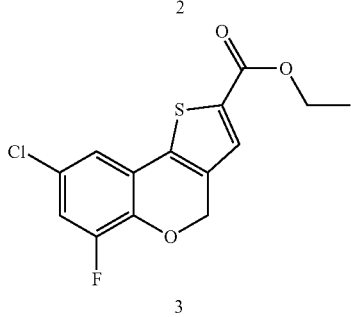

3

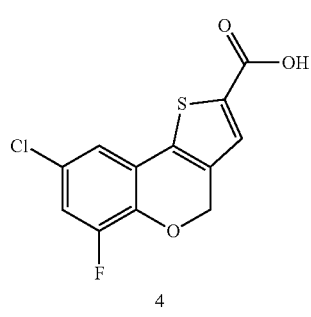

4

6-chloro-8-fluorochroman-4-one 1 (5 g, 24.9 mmol) was added dropwise to a solution of phosphorous oxychloride (2.3 mL, 24.9 mmol) in 15 mL of DMF at 0° C. The reaction mixture was stirred at 0° C. for 30 minutes then heated to 80° C. for 1.5 hours. Reaction was then cooled to room temperature and quenched with 1N NaOAc solution and extracted with dichloromethane (2×25 mL). The organic layer was concentrated in vacuo and carried to the next step without further purification.

Synthesis of 4: In a 100 mL round bottom flask, 4,6-dichloro-8-fluoro-2H-chromene-3-carbaldehyde 2 (6.1 g, 24.9 mmol) in 30 mL of ethanol was added to a solution of ethyl mercapto acetate (2.73 mL, 24.9 mmol) in sodium ethoxide (21 wt % in ethanol, 18.7 mL, 49.8 mmol) solution at 0° C. The reaction mixture was allowed to warm up to room temperature and stirred overnight. The crude reaction mixture was filtered, washed with water to collect the precipitate as desired product 3.

Without further purification, ester 3 was taken up in THF and excess 1N NaOH solution and stirred at 50° C. for 24 hr. The reaction mixture was cooled to room temperature, washed with $CH_2Cl_2$ (2×50 mL) and acidified with 1 N HCl. The resulting solid product was filtered, washed with water and dried to obtain 8-chloro-6-fluoro-4H-thieno[3,2-c]chromene-2-carboxylic acid 4 (3.89 g, 55% yield) as an off white solid.

6.6. Synthetic Method B: Preparation of 7-Methoxy-4,5-dihydronaphtho[1,2-b]thiophene-2-carboxylic acid and 6,7-difluoro-4,5-dihydronaptho[1,2-b]thiophene-2-carboxylic acid

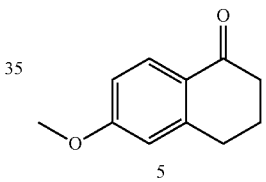

5

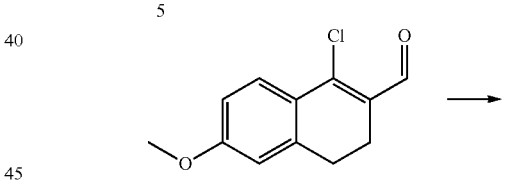

6

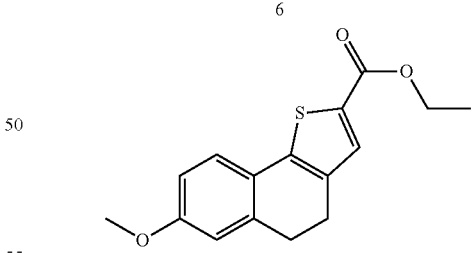

7

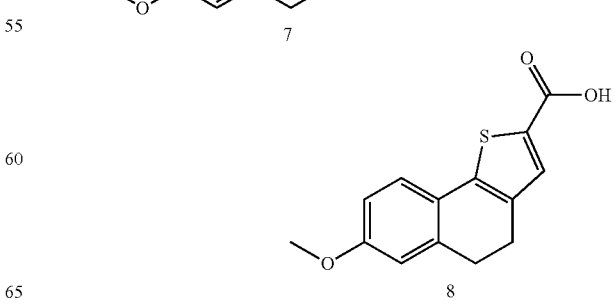

8

Under $N_2$, phosphorous oxychloride (0.444 g, 2.90 mmol) was added drop-wise to DMF (1 mL) at 0° C. then stirred vigorously for 30 minutes. 6-Methoxy-3,4-dihydronaphtha-len-1(2H)-one 5(0.500 g, 2.83 mmol) was added at 0° C. and stirred at 0° C. for 30 minutes, followed by heating at 80° C. for 90 minutes. The reaction was cooled to room temperature, poured into a 25% aqueous NaOAc solution, and extracted with diethyl ether. The combined organic layers were washed with brine solution, dried over $MgSO_4$ and concentrated in vacuo. The crude mixture was purified by silica gel chromatography (ethyl acetate-hexanes) to give 1-chloro-6-methoxy-3,4-dihydronaphthalene-2-carbalde-hyde 6 (0.327 g, 1.46 mmol, 51% yield) as an orange solid. In some cases, the aldehyde could be carried to next step without chromatographic purification.

Sodium (0.041 g, 1.78 mmol) was dissolved in ethanol (5 mL) at 0° C., followed by addition of ethyl mercaptoacetate (0.171 g, 1.43 mmol). A solution of 6 (0.320 g, 1.43 mmol) in ethanol (2 mL) was added via syringe at 0° C. The reaction was stirred at 0° C. for 30 minutes and then heated at 80° C. for 30 minutes. The reaction was cooled to room temperature, poured into $H_2O$ and extracted with dichloromethane thrice. The combined organic layers were washed with brine solution, dried over $MgSO_4$ and concentrated in vacuo. The crude mixture was purified by silica gel chromatography (ethyl acetate-hexanes) to give ethyl 7-methoxy-4,5-dihydronaphtho[1,2-b]thiophene-2-carboxy-late 7 (0.292 g, 1.01 mmol, 71% yield) as a pale yellow waxy solid. In some cases, the ester could be carried to next step without chromatographic purification.

1N NaOH (1.5 mL) was added to a stirred solution of 7 (0.288 g, 1.00 mmol) in 1:1 MeOH:THF (2 mL), then heated at 50° C. for 2 hours. The reaction was cooled to room temperature, and 10 mL of $H_2O$ was added to the reaction mixture. The mixture was thrice extracted with dichloromethane and acidified with 1N HCl to pH 5. The resulting solid was filtered, washed with $H_2O$ then dried to give 7-methoxy-4,5-dihydronaphtho[1,2-b]thiophene-2-carbox-ylic acid 8 (0.180 g, 0.691 mmol, 69% yield) as a yellow solid.

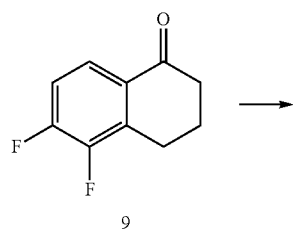

9

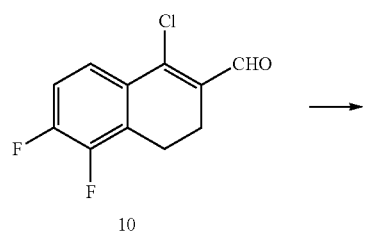

10

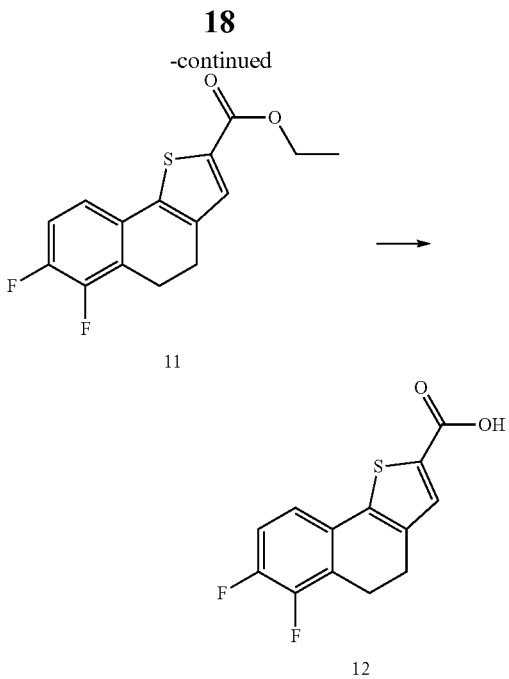

11

12

5,6-difluoro-3,4-dihydronapthalene-1(2H)-one 9 (8.5 g, 46.7 mmol) was added drop wise to a solution of phosphorous oxychloride (4.4 mL, 46.7 mmol) in DMF (20 mL) at 0° C. The reaction mixture was stirred at 0° C. for 30 minutes before heated to 80° C. for 1.5 h. The reaction was cooled to room temperature and quenched with 1N NaOAc solution and extracted with dichloromethane. The organic layer was then concentrated in vacuo and carried over to the next step.

A 100 mL round bottom flask was charged with ethyl mercaptoacetate (5.1 mL, 46.7 mmol) and sodium ethoxide/ethanol solution (21% by wt) (35 mL, 93.4 mmol) and cooled to 0° C. To the cooled reaction was added crude 10 (10.7 g, 46.7 mmol) in ethanol (30 mL). The reaction mixture was allowed to warm up to room temperature and stirred overnight. The crude reaction mixture was filtered, washed with water to collect the precipitate as desired product ester 11.

Without further purification, ester 11 was taken up in THF and excess 1N NaOH solution and stirred at 50° C. for 24 hr. The reaction mixture was cooled to room temperature and washed with dichloromethane then acidified with 1 N HCl. The resulting solid product was filtered, washed with water and dried to obtain 6,7-difluoro-4,5-dihydronaptho[1,2-b]thiophene-2-carboxylic acid 12 (7.69 g, 65% yield) as a white solid.

6.7. Synthetic Method C: Preparation of 6,9-difluoro-4H-thieno[3,2-c]thiochromene-2-carboxylic acid

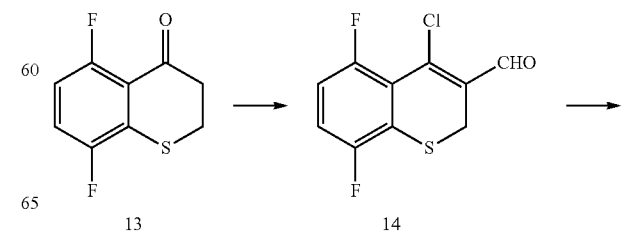

13    14

-continued

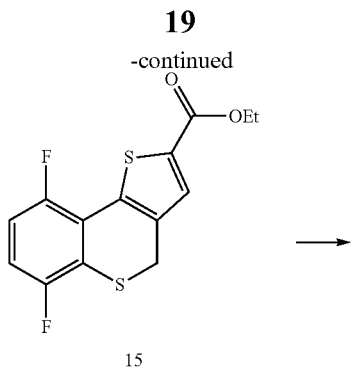

15

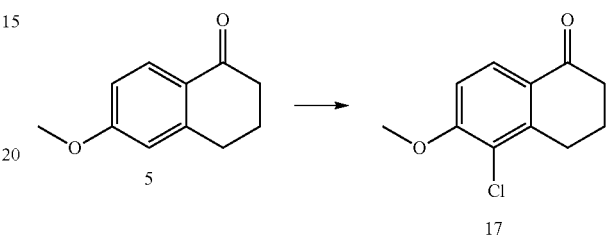

Phosphorous oxychloride (58.99 mmol, 5.4 mL) was added drop wise to dry DMF (26 mL) at 0° C., 10.4 g 5,8-difluorothiochroman-4-one 13 (51.74 mmol) was added slowly while keeping the temperature less than 5° C. The reaction mixture was stirred for 0.5 hours and then heated at 80° C. for 1.5 hours. The reaction mixture was cooled to room temperature, and then poured into 9 mL ice cold aqueous sodium acetate (25%, W/V) solution. The mixture was extracted by diethyl ether twice. The organic layer was combined, washed with brine, dried under Na$_2$SO$_4$ and concentrated in vacuo to afford 4-chloro-5,8-difluoro-2H-thiochromene-3-carbaldehyde 14 as a brown oil of 10.7 g.

18.24 mL sodium ethanolate (21% in EtOH) (48.9 mmol) in 250 mL EtOH was cooled to 0° C., 5.20 mL ethyl 2-mercaptoacetate (47.4 mmol) was added drop wise at <5° C., 10.7 g 4-chloro-5,8-difluoro-2H-thiochromene-3-carbaldehyde 14 (43.4 mmol) was then added slowly at 0° C. The reaction mixture was stirred at room temperature overnight before heated to 70° C. for 2 hours. The product precipitated from the crude reaction upon cooling. The reaction mixture was filtered, rinsed with 1:3 MeOH/H2O solution, and dried under vacuum to afford 8.91 g ethyl 6,9-difluoro-4H-thieno[3,2-c]thiochromene-2-carboxylate 15 as an off-white solid.

To a solution of NaOH (5.2 g, 130 mmol, 5.07 eq) in H$_2$O (50 mL) was added ethyl 6,9-difluoro-4H-thieno[3,2-c]thiochromene-2-carboxylate 15 (8.0 g, 25.6 mmol, 1 eq) in THF (90 mL). The reaction mixture was heated to 60° C. for 2 h, and after 25 mL of H$_2$O and 25 mL of THF were added to maintain solution the reaction was heated at 68° C. for 1 h. The reaction mixture was cooled to room temperature and concentrated to remove organic solvent. The reaction mixture was diluted with H$_2$O and 1N HCl was added until pH=2 to precipitate out the product. The precipitate was filtered, rinsed with H$_2$O and 1:3 MeOH/H$_2$O, and dried under vacuum overnight to afford 5.8 g 6,9-difluoro-4H-thieno[3,2-c]thiochromene-2-carboxylic acid 16 as a pale yellow solid.

6.8. Synthetic Method D: Preparation of 5-chloro-6-methoxy-3,4-dihydronapthalen-1(2H)-one

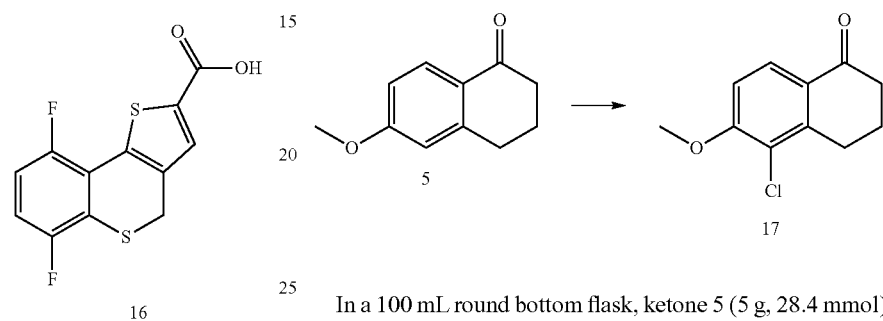

In a 100 mL round bottom flask, ketone 5 (5 g, 28.4 mmol) and N-chlorosuccinimide (3.78 g, 28.4 mmol) were suspended in water and stirred at 60° C. Then 40% aqueous sulfuric acid (7.6 mL, 56.7 mmol) was added slowly and the reaction mixture stirred at 60° C. for 6 hours. Then the reaction mixture was cooled to room temperature, filtered and washed with water. The solid was re-dissolved in dichloromethane (25 mL), dried over MgSO$_4$ and concentrated in vacuo to obtain crude 5-chloro-6-methoxy-3,4-dihydronapthalene-1(2H)-one 17 (2 g, 34% yield) as a solid, which was used in the next step without further purification.

6.9. Synthetic Method E: Preparation of 5-fluoro-6-methoxy-3,4-dihydronaphthalen-1(2H)-one

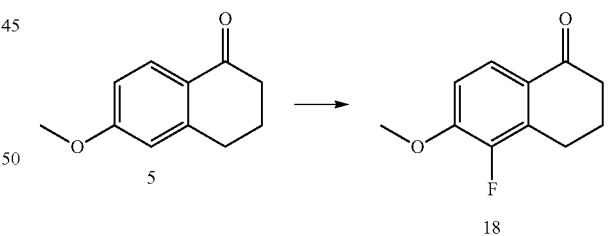

In a 100 mL round bottom flask, ketone 5 (1 g, 5.68 mmol) was taken up in acetonitrile (8 mL) and selectfluor (3.02 g, 8.5 mmol) was added and the reaction stirred at room temperature for 2 hours before heated to 40° C. for 48 hours. Then the reaction mixture was cooled to room temperature and concentrated in vacuo then re-dissolved in methanol and filtered. The methanol layer was concentrated in vacuo and purification by silica gel column chromatography with hexane/ethyl acetate (0 to 30%) to produce 5-fluoro-6-methoxy-3,4-dihydronapthalen-1(2H)-one 18 (395 mg, 36% yield).

6.10. Synthetic Method F: Preparations of 5-bromo-6-methoxy-3,4-dihydronapthalen-1(2H)-one and 2-methoxy-5-oxo-5,6,7,8-tetrahydronaphthalene-1-carbonitrile

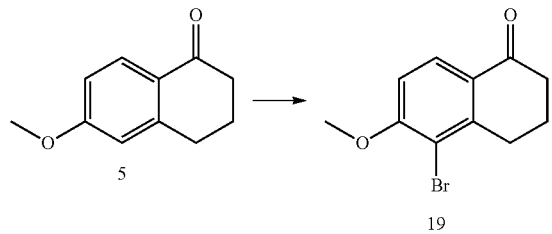

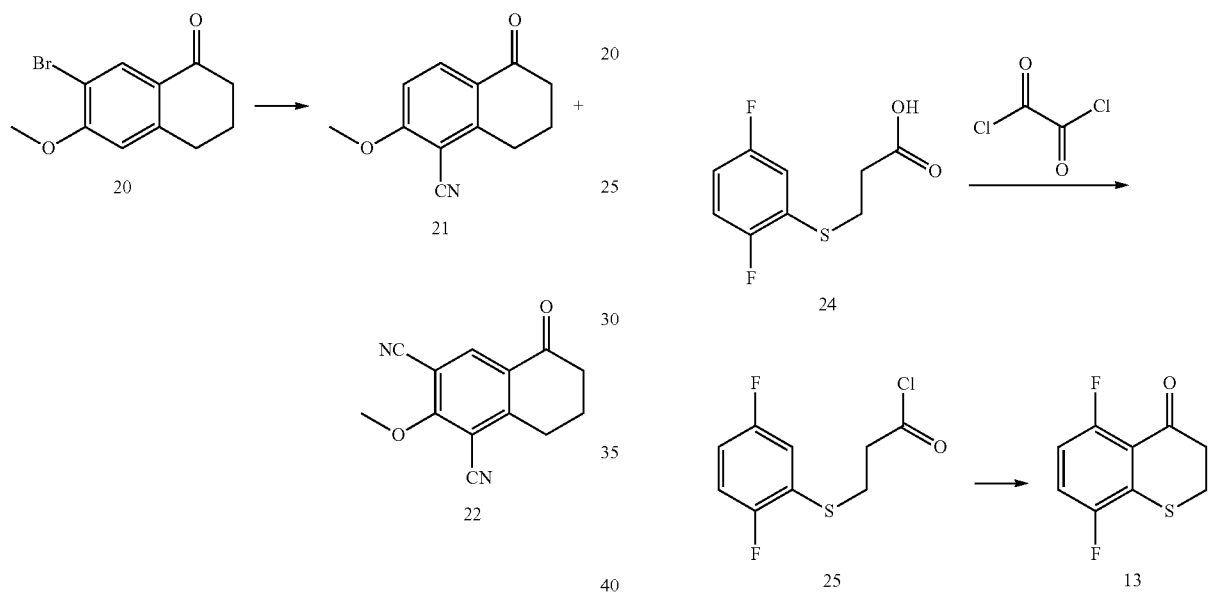

In a 100 mL round bottom flask, ketone 5 (5 g, 28.4 mmol) and N-bromosuccinimide (5.05 g, 28.4 mmol) were taken up in water and stirred at 60° C. Then 40% aqueous sulfuric acid (7.6 mL, 56.7 mmol) was added slowly and the reaction mixture was stirred at 60° C. for 5 hours. The reaction mixture was cooled to room temperature and product filtered off and washed twice with water. It was dried over night under vacuum to afford a 3:1 mixture of 5-bromo-6-methoxy-3,4-dihydronapthalene-1(2H)-one 19 and 7-bromo-6-methoxy-3,4-dihydronapthalene-1(2H)-one 20 as a solid, which was directly used in the next step (6.7 g, 92% yield).

In a microwave vial a mixture of 19 and 20 (0.660 g, 1 eq, 0.78 mmol) and copper (II) cyanide (0.254 g, 1.1 eq, 0.86 mmol) were suspended in NMP. The mixture was heated in a microwave reactor at 160° C. for 30 minutes. The reaction was cooled, diluted with methanol and filtered. The filtrate was concentrated then taken up in water and solid product filtered off and dried. The solid mixture was purified by silica gel chromatography (hexane: ethyl acetate) to obtain pure 2-methoxy-5-oxo-5,6,7,8-tetrahydronaphthalene-1-carbonitrile 21 (0.155 g, 30%) and 3-methoxy-8-oxo-5,6,7,8-tetrahydronaphthalene-2-carbonitrile 22 (0.06 g, 12%).

6.11. Synthetic Method G: Preparation of 5,8-difluorothiochroman-4-one

To a solution of NaOH (3.83 g, 95.8 mmol) dissolved in $H_2O$ (20 mL) in a 100 mL round bottom flask at 0° C., was added 2,5-difluorobenzenethiol (23 (11 g, 75.3 mmol) slowly. The resulting solution was stirred 5 minutes, then (11.0 g, 101.8 mmol) 3-chloropropanoic acid was slowly added. The mixture was heated at 70° C. overnight. Additional NaOH (1.2 g, 30.0 mmol) in $H_2O$ (1 mL) was added and the reaction was allowed to heat for 24 h at 70° C. The reaction was cooled to 0° C. and upon acidification with 1N HCl, the product precipitated out. The precipitate was filtered, rinsed with water, and dried in vacuo to afford 3-((2,5-difluorophenyl)thio)propanoic acid 24 (17.4 g, 100%) as a white solid.

To a solution of 24 (17.4 g, 79.82 mmol) in dichloromethane (250 mL) at 0° C., oxalylchloride (10.4 mL, 119.20 mmol) was added slowly, then a catalytic amount of DMF was added drop wise. The reaction mixture was stirred at room temperature for 6 hours. Another portion of oxalylchloride (2 mL, 22.84 mmol) and catalytic amount of DMF were added in at room temperature. The reaction was stirred overnight and the reaction mixture was concentrated in vacuo to afford the crude 3-((2,5-difluorophenyl)thio)propanoyl chloride 25, which was used directly without further purification.

A solution of freshly prepared acid chloride 25 (79.8 mmol) in dichloromethane (350 mL) was cooled to 0° C., then AlCl₃ (15 g, 112.49 mmol) was added slowly. The reaction mixture was stirred at room temperature overnight under N₂. The reaction was quenched with ice water and extracted twice with ethyl acetate. The combined organic layer was washed with brine, dried over Na₂SO₄ and concentrated in vacuo to afford 3 (13 g, 81.5%) as a yellow solid.

6.12. Synthetic Method H: Preparation of 7-(trifluoromethyl)chroman-4-one and 5-(trifluoromethyl)chroman-4-one

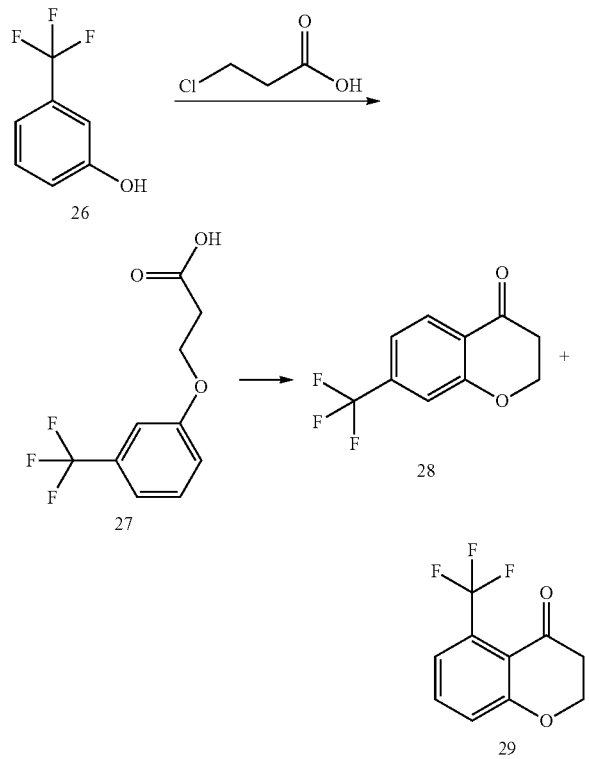

In a 100 mL round bottom flask, 3-(trifluoromethyl) phenol 26 (4.68 g, 30 mmol) and 3-chloropropanoic acid (6.3 mL, 60 mmol) were taken up in 2N NaOH (40 mL) and refluxed for 1 hour. Then the reaction mixture was cooled to room temperature, acidified with 6N HCl and extracted with ethyl acetate (2×25 mL). The combined organic layer was washed with brine, dried over $_{NA2}SO_4$ and concentrated in vacuo to obtain acid 27, which was used directly without further purification.

In a 100 mL round bottom flask, crude acid 27 (7.02 g, 30 mmol) was suspended in polyphosphoric acid (15 mL) and heated at 100° C. for 20 minutes. Then the reaction mixture was cooled to room temp and ice was added while stirring. The resulting solid precipitate was filtered and washed twice with cold water. This crude mixture was purified by silica gel chromatography (ethyl acetate-hexanes) to afford 7-(trifluoromethyl)chroman-4-one 28 (0.899 g, 14.4% yield) and 5-(trifluoromethyl)chroman-4-one 29 (0.214 g, 3.4% yield).

6.13. Synthetic Method I: Preparation of 6,9-difluoro-4H-thieno[3,2-c]thiochromene-2-carboxamide, Synthesis of 7,9-difluoro-4H-thieno[3,2-c]chromene-2-carboxamide, 6,8-dimethyl-4,5-dihydronaphtho[1,2-b]thiophene-2-carboxamide, 2-(6,8-dimethyl-4,5-dihydronaphtho[1,2-b]thiophene-2-carboxamido)acetate, and N-(2-hydroxyethyl)-4,5-dihydronaphtho[1,2-b]thiophene-2-carboxamide

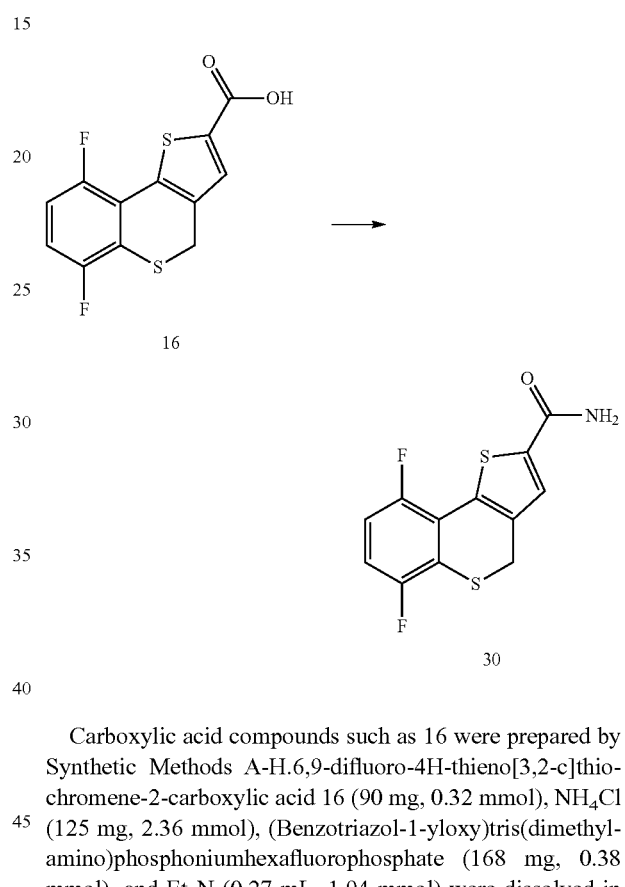

Carboxylic acid compounds such as 16 were prepared by Synthetic Methods A-H. 6,9-difluoro-4H-thieno[3,2-c]thiochromene-2-carboxylic acid 16 (90 mg, 0.32 mmol), NH₄Cl (125 mg, 2.36 mmol), (Benzotriazol-1-yloxy)tris(dimethylamino)phosphoniumhexafluorophosphate (168 mg, 0.38 mmol), and Et₃N (0.27 mL, 1.94 mmol) were dissolved in DMF (2 mL) and stirred at room temperature for 2 hours. Addition of water to the reaction mixture precipitated the product. The precipitate was filtered, rinsed by 1:3 MeOH/H2O, H2O, heptanes, and dried in vacuo to afford carboxamide 30 (69.4 mg, 77%) as a white solid.

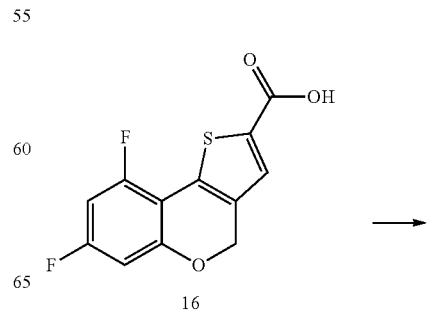

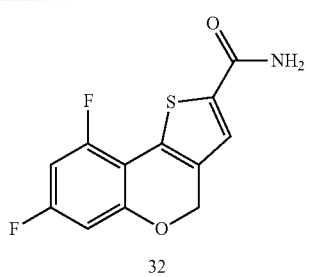

32

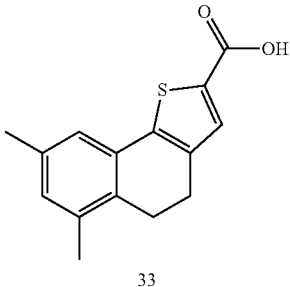

33

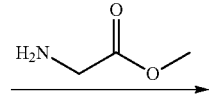

Carboxylic acid compounds such as 31 were prepared by Synthetic Methods A-H. In a 50-mL round bottom flask, acid 31 (0.154 g, 0.57 mmol) was suspended in DMF (3 mL). To the suspension was added ammonium chloride (0.307 g, 5.7 mmol), HATU (0.327 g, 0.86 mmol) and triethyl amine (960 µL, 6.9 mmol) sequentially at room temperature and stirred for 10 h. The reaction was diluted with water and the crude precipitate product was purified by preparative HPLC to yield carboxamide 32 (0.054 g, 35% yield).

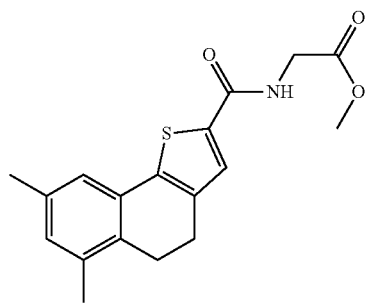

35

Acid 33 (0.06 g, 0.232 mmol, 1 eq.) was dissolved in dichloromethane (1.2 mL). This solution was treated with oxalyl chloride (0.20 mL, 2.32 mmol, 10 eq.) and 1 drop DMF. After stirring for 1 hour the reaction was concentrated thrice from dichloromethane. The crude yellow orange solid (0.0.0782 g, quant.) was dissolved in THF (1.5 mL) and was added to a solution of methyl 2-aminoacetate (0.0437 g, 0.348 mmol, 1.5 eq) in THF (0.5 mL). TEA (0.10 mL, 0.696 mmol, 3 eq.) was then added and the reaction stirred overnight. The reaction was then poured into 1 N HCl and water and was thrice extracted with Ethyl acetate. The combined organic layers were washed with sat. aq. NaHCO₃, water and brine, dried over MgSO₄, filtered and concentrated. The crude clear yellow oil was purified using silica gel column chromatography with 20 to 30% ethyl acetate in hexanes, yielding 35 as an off white solid (0.0576 g, 74%).

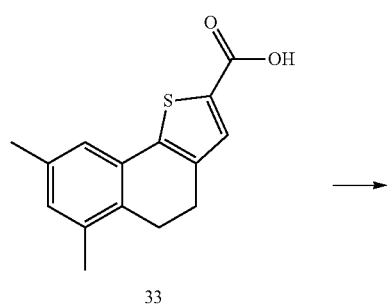

33

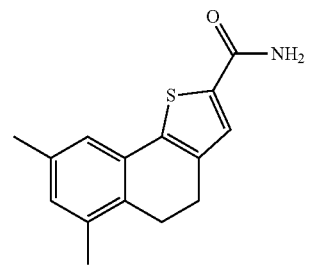

34

Carboxylic acid compounds such as 33 were prepared by Synthetic Methods A-H. A solution of acid 33(0.04 g, 0.155 mmol) in dichloromethane (0.8 mL) was treated with oxalyl chloride (0.14 mL, 1.55 mmol) and 1 drop DMF. After stirring for 1 hour the reaction was concentrated thrice from dichlormethane. The crude yellow orange solid (0.052 g, quant.) was dissolved in THF (1 mL) and added to an ice cold solution of ammonium hydroxide (30 µL, 0.755 mmol) in THF. The reaction slowly warmed to room temperature and stirred overnight. The reaction was then poured into 1 N HCl. The layers were separated and the aqueous portion was thrice extracted with Ethyl acetate. The combined organic layers were washed with sat. aq. NaHCO₃, water and brine, dried over MgSO₄, filtered and concentrated. The crude light yellow solid was triturated with methanol to yield carboxamide 34 (can also be found in patent WO2006/80406 A (1) as an off white solid (0.0174 g, 44% yield).

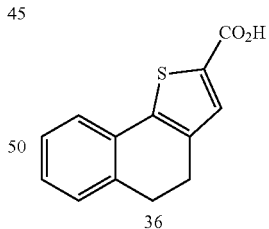

36

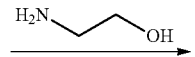

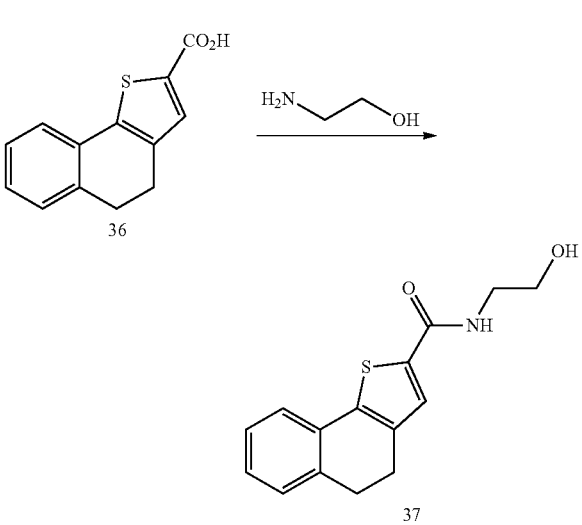

37

Carboxylic acid compounds such as 36 were prepared by Synthetic Methods A-H. Acid 36 (25 mg, 1 eq, 0.11 mmol), 2-amino-ethanol (7 mg. 1 eq), EDCl (26 mg, 1.2 eq) and HOBT (18 mg, 1.2 eq) were combined in dichloromethane (1.5 mL) and the mixture stirred at room temperature over night. The mixture was diluted with Ethyl acetate, washed with H2O, dried over MgSO4 and concentrated. Purification by preparative HPLC afforded the desired product 37 (10 mg, 33%). Compounds were purified by silica gel chromatography or preparative HPLC.

6.14. Synthetic Method J: Preparations of 2-(6,8-dimethyl-4,5-dihydronaphtho[1,2-b]thiophene-2-carboxamido)acetic acid) and N-(2-aminoethyl)-4,5-dihydronaphtho[1,2-b]thiophene-2-carboxamide

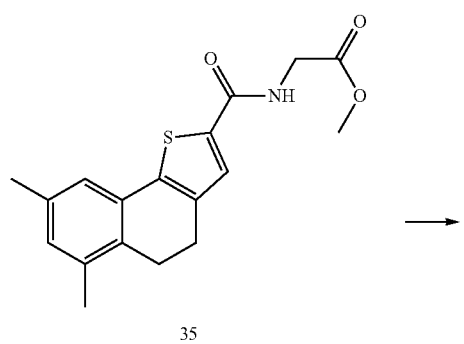

35

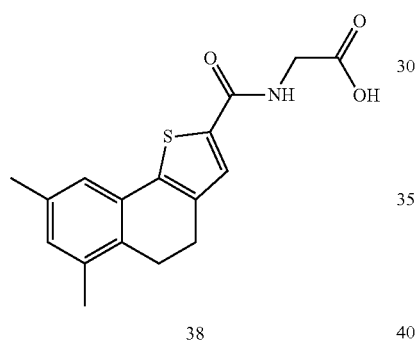

38

Synthesis of 38: Compounds such as 35 were prepared using Synthetic Method I. Ester 35 (0.043 g, 0.130 mmol) was dissolved in THF (0.2 mL) and methanol (0.3 mL) and aqueous sodium hydroxide (1.0 N, 0.14 mL, 0.143 mmol) was added. After stirring at ambient temperature for 30 minutes the reaction was concentrated. The solid residue was suspended in 1 N aqueous NaOH and water, cooled to 0° C. and acidified with 1 N aqueous HCl to pH~2. The solid was collected via vacuum filtration, washed with water and dried, yielding acid 38 as an off-white solid (0.035 g, 86%).

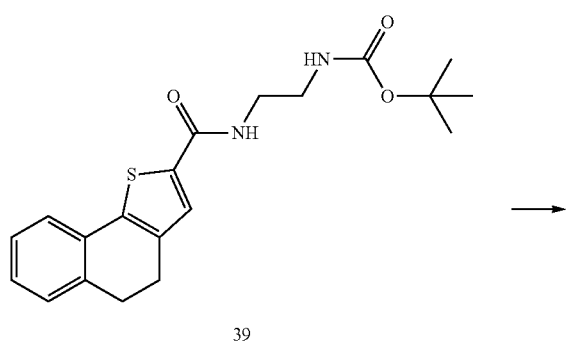

39

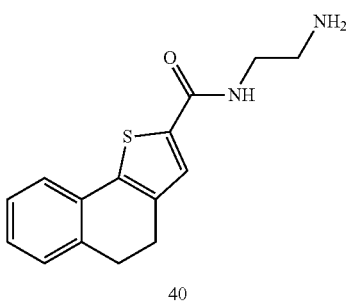

40

Compounds such as amide 39 were prepared using Synthetic Method I. To a solution of 39 (25 mg, 0.067 mmol) in dioxane/MeOH (1:1, 1 mL) was added HCl (4 N solution in dioxane, 12 mg, 0.34 mmol, 83 µL) and the mixture stirred over night at room temperature. The mixture was concentrated and purified by preparative HPLC to afford the desired product 40 (6 mg, 33%).

6.15. Synthetic Method K: Preparation of 6,8-difluoro-4H-thieno[3,2-c]thiochromene-2-carboxylic acid 5-oxide

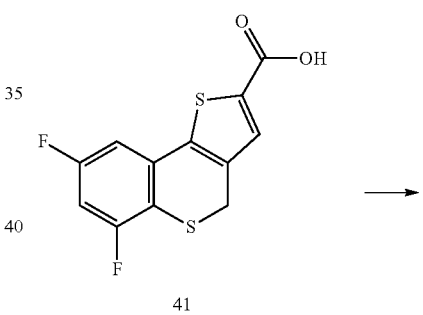

41

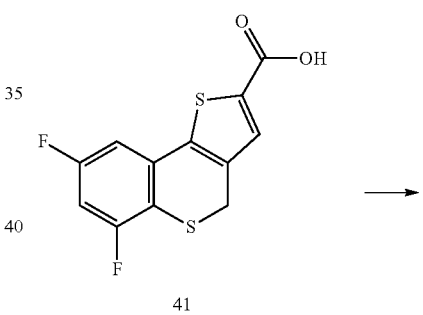

42

Compounds such as 41 were prepared using Synthetic Methods C and G. Acid 41 (200 mg, 0.70 mmol) and m-CPBA (77%) (152 mg, 0.70 mmol) in dichloromethane was stirred at room temperature for 3 hrs. 100 µl dimethylsulfide was added to quench excess m-CPBA and the resulting mixture was stirred for 1.5 hour. No peroxide was observed by a low level peracetic acid test strip and a peroxide test strip. The reaction was concentrated in vacuo and the residue was purified by preparative HPLC to afford 42 (28.7 mg, 13.6%) as a white solid.

6.16. Synthetic Method L: Preparation of 6,8-difluoro-4H-thieno[3,2-c]thiochromene-2-carboxylic acid 5,5-dioxide

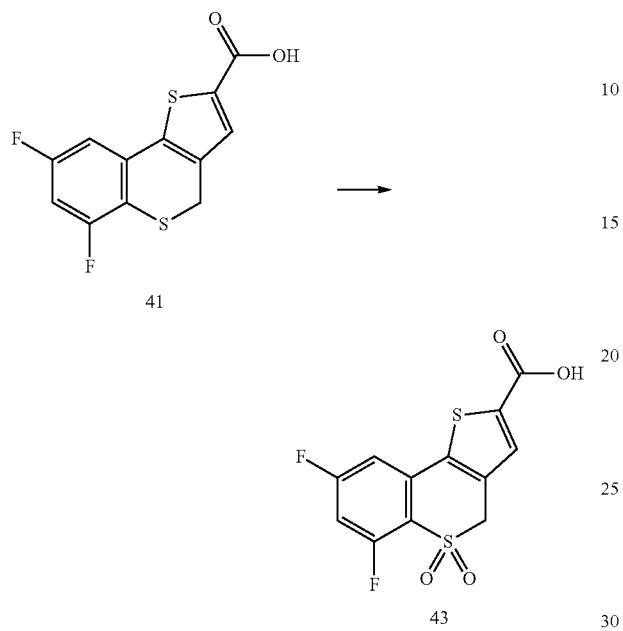

Method 1: 6,8-difluoro-4H-thieno[3,2-c]thiochromene-2-carboxylic acid 41 (100 mg, 0.35 mmol, 1.0 eq) and m-CPBA (77%) (304 mg, 1.40 mmol) in dichloromethane was stirred at room temperature for 6 hrs. The reaction was quenched with 100 µL dimethylsulfide. No peroxide was observed by a low level peracetic acid test strip and a peroxide test strip. The crude product was purified by preparative HPLC to afford 43 (13.1 mg, 12%) as a white solid.

Method 2: A solution of acid 41 (100 mg, 0.35 mmol) in peracetic acid (35% in acetic acid, 0.4 mL) was stirred at room temperature for 1 hr. The reaction mixture was quenched with dimethyl sulfide and the resulting mixture was stirred overnight. No peroxide was observed by a low level peracetic acid test strip and a peroxide test strip. The reaction was diluted with water, extracted with ethyl acetate twice and concentrated in vacuo. Preparative HPLC purification afforded 43 (65 mg, 59%) as a white solid.

6.17. Synthetic Method M: Preparation of 3-amino-4H-thieno[3,2-c]thiochromene-2-carboxylic acid

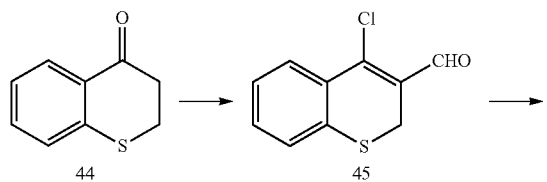

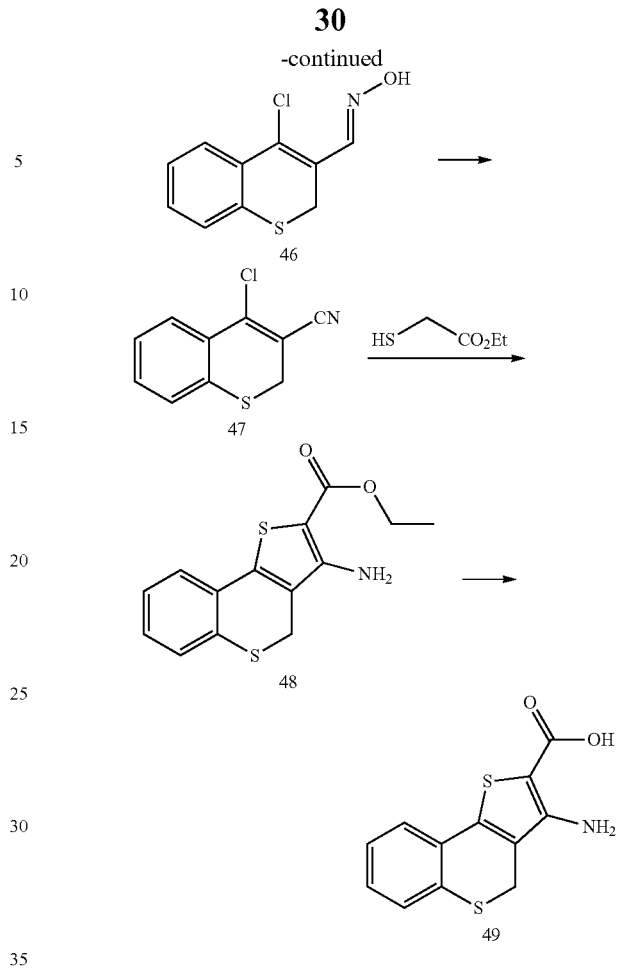

Thiochroman-4-one 44 (0.82 g, 1.0 eq., 5 mmol) was added dropwise to a solution of phosphorous oxychloride (0.46 mL, 1.0 eq., 5 mmol) in 5 mL DMF at 0° C. The reaction mixture was stirred at 0° C. for 30 minutes before heated to 80° C. for 1.5 hours. The reaction was then cooled to room temperature, quenched with 1N aq. NaOAc and extracted with dichloromethane (2×25 mL). The organic layer was concentrated in vacuo to afford crude 45, which was carried over to the next step directly without further purification.

A solution of crude 45 from reaction above and NH2OH.HCl (420 mg, 6 mmol) in isopropanol (10 mL) was heated to reflux for 3 hrs. The reaction was concentrated down and dried over high vacuum to a yellow solid 46 of 0.79 g, which was pure enough to use in the next reaction without further purification.

To a solution of crude 46 (0.79 g, 3.5 mmol) in 10 mL toluene was added SOCL (2 (1.19 g, 10 mmol) and the reaction was allowed to stir at room temperature overnight. The reaction was concentrated to a yellow brown solid 47 of 0.62 g and used directly without further purification.

To a mixture of ethyl thioglycolate (0.44 g, 1.2 eq., 3.6 mmol) and potassium carbonate (0.83 g, 6 mmol) in isopropanol (10 mL) was added crude 33 (0.62 g, 3 mmol) in isopropanol (5 mL), and the reaction was stirred at room temperature for 2 hrs before heated to 80° C. for 2 hrs. The reaction was concentrated after cooled to room temperature, diluted with water and extracted with ethyl acetate twice. The organic layers were combined, washed with brine, dried over sodium sulfate and concentrated to a brown yellow residue 48.

The ethyl ester crude 48 from reaction above was hydrolyzed with aq. NaOH using Synthetic Method J to afford 49 as a brown solid (112 mg, 8.5% overall yield for 5 steps).

6.18. Synthetic Method N: Preparation of 3-methyl-3,4-dihydronaphthalen-1(2H)-one

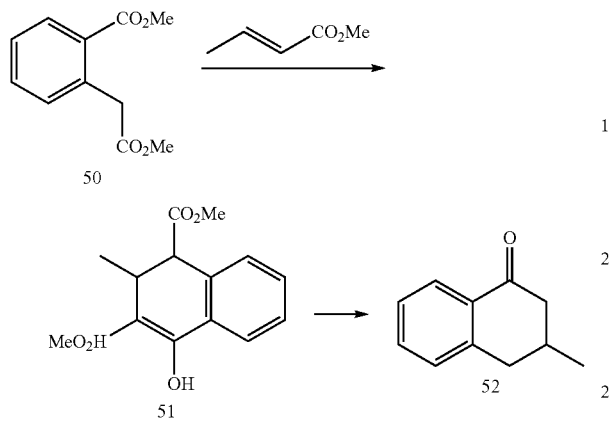

To a 50 mL round bottom flask with methanol (3 mL) was added sodium metal (130 mg), and the mixture was stirred at room temperature for 30 min to prepare the sodium methoxide. Methyl 2-(2-methoxy-2-oxoethyl)benzoate 50 (416 mg, 2 mmol) was added and the reaction was stirred for 10 mins. After addition of methyl crotonate (300 mg, 3 mmol), the reaction was heated to 85° C. for 4 hrs. The reaction was acidified with 1N HCl, extracted with ethyl acetate (50 mL×3). The organic layers were combined, washed with brine, dried over sodium sulfate and concentrated to a dark brown residue 51, which was used directly without further purification.

To a high pressure vessel with crude 51 from reaction above in dry DMSO (2 mL) was added sodium chloride (100 mg) and heated to 200° C. for 2 hrs. The dark brown solution was cooled to room temperature and diluted with water (50 mL). The reaction mixture was extracted with ether (25 mL×3), washed with brine, dried over sodium sulfate, and concentrated to a reddish brown residue 52 (176 mg, 55% over 2 steps).

6.19. Synthetic Method O: Preparation of 6,7-difluoro-4,4-dimethyl-3,4-dihydronaphthalen-1(2H)-one

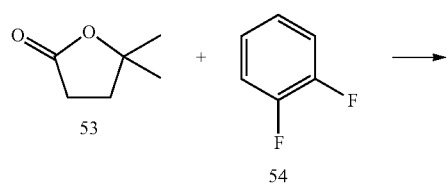

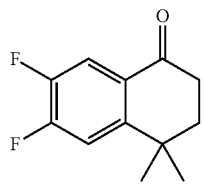

To 5,5-dimethyl-dihydro-furan-2-one 53 (1.14 g, 10 mmol) and 1,2-difluorobenzene 54 (1.14 g, 10 mmol) in a sealed tube was added aluminum chloride (3.55 g, 12 mmol) and the reaction was heated to 100° C. overnight. The resulting dark brown residue was dissolved in ice water, and extracted with ethyl acetate (50 mL×3). The organic layers were combined, washed with sat. $NaHCO_3$, brine, dried over $Na_2SO_4$ and concentrated to get the desired product 55 which was used directly without further purification.

6.20. Synthetic Method P: Preparation of 6,7-difluoro-4-methyl-3,4-dihydronaphthalen-1(2H)-one

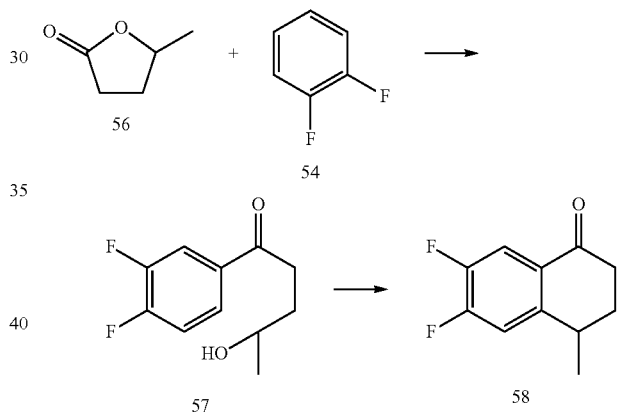

To 5-methyl-dihydro-furan-2-one 56 (1 g, 1.0 eq., 10 mmol) and 1,2-difluorobenzene 54 (1.14 g, 1.0 eq., 10 mmol) in a seal tube was added aluminum chloride (3.55 g, 1.2 eq., 12 mmol) and the reaction was heated to 100° C. overnight. The resulting dark brown residue was dissolved in ice water, and extracted with ethyl acetate (50 mL×3). The organic layers were combined, washed with sat. $NaHCO_3$, brine, dried over sodium sulfate and concentrated to yield crude 57, which was used in the next step without further purification.

To a sealed tube with crude 57 from reaction above was added trifluoromethanesulfonic acid (1.5 g, 1.0 eq., 10 mmol) and phosphorus pentoxide (2.8 g, 2.0 eq., 20 mmol), and the solid was mixed carefully with a stirrer. The reaction mixture was heated to 80° C. for 5 hrs. After cooled to room temperature, the reaction was diluted with ice water, extracted with ether (25 mL×3), washed with sat. $NaHCO_3$, brine, dried over $Na_2SO_4$ and concentrated to give 58 of 1.27 g (65% overt steps).

6.21. Synthetic Method Q: Preparation of 5-Oxo-5,6,7,8-tetrahydronaphthalene-1-carbonitrile

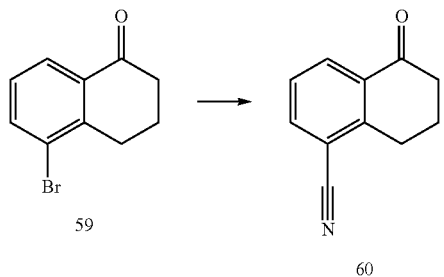 [SMILES: O=C1CCCc2c(Br)cccc21 ; N#Cc1cccc2c1CCCC2=O]

Under N$_2$, bromide 59 (1.00 g, 4.44 mmol), potassium cyanide (0.318 g, 4.88 mmol), NiCl$_2$(PPh$_3$)$_2$ (0.145 g, 0.222 mmol), triphenyl phosphine (0.116 g, 0.444 mmol) and zinc (0.087 g, 1.33 mmol) were suspended in acetonitrile (10 mL) then heated at 70° C. overnight. The reaction was cooled to room temperature then diluted with DCM (50 mL) and washed with H2O, brine solution, dried over MgSO$_4$ then concentrated in vacuo. The crude product was crystallized from hot ethyl acetate/hexanes to give nitrile 60 (0.380 g, 2.21 mmol, 50% yield) as a crystalline white solid.

6.22. Synthetic Method R: Preparation of 6,8-difluorospiro[chroman-2,1'-cyclopentan]-4-one

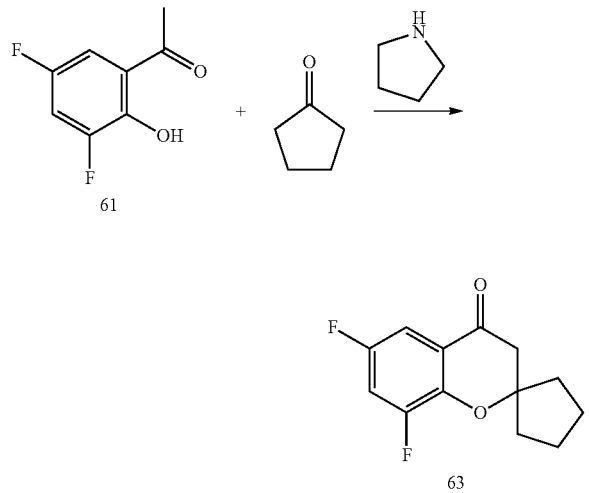

To a solution of 3',5'-difluoro-2'-hydroxyacetophenone 61 (1.72 g, 10 mmol) and cyclopentanone 62 (1.01 g, 12 mmol) in toluene (20 mL) was added pyrrolidine (0.214 g, 3 mmol) drop wise. The reddish brown solution was stirred at room temperature for 1 hr before heated to reflux for 6 hrs with a Dean-Stark on top to remove the water generated. After cooled to room temperature, the reaction mixture was poured onto crushed ice and extracted with ether (50 mL×3). The organic layer was combined, washed with brine, dried over NA2SO$_4$ and concentrated to brown yellow oil 63, which was used directly without further purification.

6.23. Synthetic Method S: Preparation of 8-Oxo-5,6,7,8-tetrahydronaphthalene-2-carbonitrile

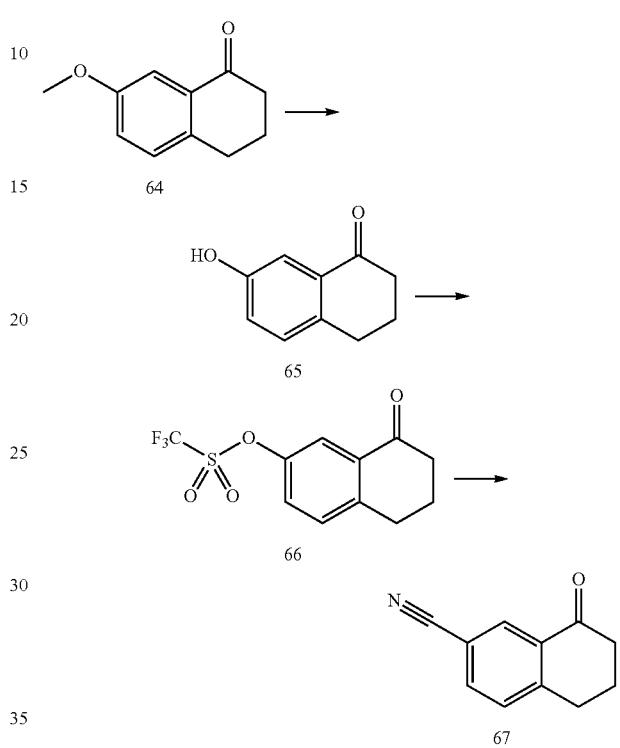

Under N$_2$, ether 64 (0.700 g, 3.97 mmol) was added to a suspension of aluminum chloride (1.32 g, 9.92 mmol) in toluene (10 mL) at room temperature, then refluxed for 30 minutes. The reaction was cooled to room temperature and quenched with H$_2$O (50 mL). The mixture was extracted with ethyl acetate thrice and the combined organic layers were washed with brine solution, dried over MgSO$_4$ and concentrated in vacuo. The crude product was crystallized by dissolving in acetone (5 mL) followed by addition of hexanes (25 mL) then cooled overnight to give phenol 65 (0.536 g, 3.30 mmol, 83% yield) as an orange crystalline solid.

Under N$_2$, 2,6-lutidine (0.418 g, 3.91 mmol) and DMAP (0.079 g, 0.652 mmol) were added to a suspension of 65 (0.529 g, 3.26 mmol) in DCM cooled to −40° C. Trifluoromethanesulfonic anhydride (1.11 g, 3.91 mmol) was added dropwise. The reaction was stirred at −40° C. for 5 minutes, removed from the cooling bath and stirred at room temperature for 4 hours. The reaction was washed with H$_2$O, 1N HCl, brine solution, dried over MgSO$_4$ and concentrated in vacuo to give triflate 66 (0.924 g, 3.14 mmol, 96% yield) as an orange crystalline solid.

Under N$_2$, triflate 66 (0.924 g, 3.14 mmol), potassium cyanide (0.224 g, 3.45 mmol), NiCl$_2$(PPh$_3$)$_2$ (0.102 g, 0.157 mmol), PPh$_3$ (0.082 g, 0.314 mmol) and Zn (0.065 g, 1.00 mmol) were suspended in acetonitrile (10 mL) and heated at 70° C. for 4 hours. The reaction was cooled to room temperature then diluted in DCM (50 mL) and washed with H$_2$O, brine solution, dried over MgSO$_4$ and concentrated in vacuo. The crude oil was purified by silica gel chromatography (ethyl acetate-hexanes gradient) to give nitrile 67 (0.408 g, 75%) as a crystalline white solid.

6.24. Synthetic Method T: Preparation of 6-Methyl-3,4-dihydronaphthalen-1(2H)-one (4a)

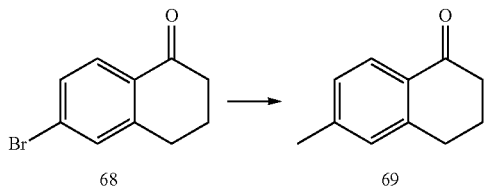

Under N$_2$, bromide 68 (1.00 g, 4.44 mmol), Pd(PPh$_3$)$_4$ (0.796 g, 0.689 mol), and K$_2$CO$_3$ (1.84 g, 13.3 mmol) were suspended in DMF (10 mL). Trimethylboroxine (1.26 g, 10.0 mmol) was added dropwise via syringe at room temperature, then the reaction was heated at 105° C. overnight. The crude reaction was cooled to room temperature, diluted with DCM (50 mL), washed with H$_2$O (3×), brine solution, dried over MgSO$_4$ and concentrated in vacuo. The crude oil was purified by silica gel chromatography (ethyl acetate-hexanes gradient) to give ketone 69 (0.648 g, 91% yield) as a clear oil.

6.25. Synthetic Method U: Preparation of 4-(2-fluoro-4-methylphenyl)-4-oxobutanoic acid and 4-(2-fluoro-3-methylphenyl)-4-oxobutanoic acid

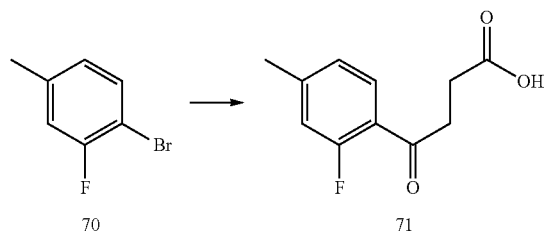

4-Bromo-3-fluorotoluene 70 (1.34 g, 7.10 mmol) was taken up in THF (70 mL) and cooled to −78° C. and n-butyllithium (2.5 M in hexanes, 3.4 mL, 8.52 mmol) was added dropwise over 30 minutes. This reaction then stirred at −78° C. for 1 hour. In another flask succinic anhydride 3 (0.924 g, 9.23 mmol) was suspended in THF (12 mL) and cooled to −78° C. The anion solution was then transferred dropwise via cannula to the succinic anhydride solution over 25 minutes. The reaction slowly warmed to room temperature as it stirred overnight. The reaction was diluted with ethyl acetate and thrice extracted with 3 N aqueous NaOH. The combined aqueous portions were cooled to 0° C., acidified to pH~1 with concentrated HCl and was thrice extracted with ethyl acetate. These combined organic layers were washed with water and brine, dried over MgSO$_4$, filtered and concentrated. Keto-acid 71 was isolated as a yellow solid (0.718 g, 48%) and used without further purification.

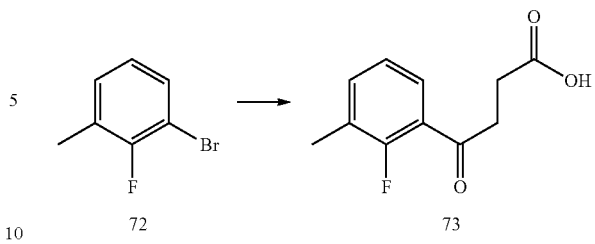

3-Bromo-2-fluorotoluene 72 (0.465 g, 2.46 mmol) was taken up in THF (25 mL) and cooled to −78° C. n-Butyllithium (2.5 M in hexanes, 1.2 mL, 2.95 mmol) was added and the reaction stirred for 30 minutes. Another round bottom flask was charged with succinic anhydride (0.320 g, 3.20 mmol) and THF (4 mL), cooled to −78° C. and equipped with a jacketed addition funnel, which was cooled to −78° C. After the stirring period, the anion solution was transferred quickly to the cold addition funnel. The anion solution was added to the anhydride solution over 10 minutes. After stirring for 90 minutes, the reaction was quenched with small amount of water while still cold, and then allowed to warm to room temperature slowly overnight. The reaction was diluted with Ethyl acetate and thrice extracted with 1 N aqueous NaOH. The combined aqueous layers were cooled to 0° C. and acidified to pH~1 with concentrated HCl. This acidic aqueous portion was thrice extracted with ethyl acetate and the combined organic layers were washed with water and brine, dried over MgSO$_4$, filtered and concentrated, yielding acid 73 as a pale yellow solid (0.344 g, 67%), which was used without further purification.

6.26. Synthetic Method V: Preparation of 5-fluoro-7-methyl-3,4-dihydronaphthalen-1(2H)-one and 5-fluoro-6-methyl-3,4-dihydronaphthalen-1(2H)-one

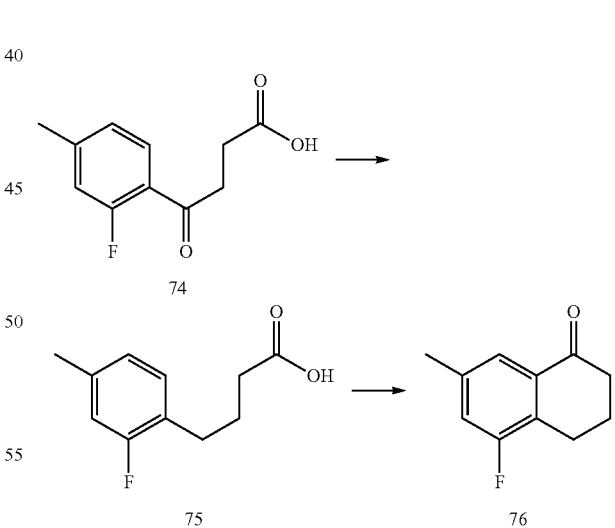

Keto-acid 74 (1.62 g, 7.71 mmol) was dissolved in TFA (8 mL) and triethylsilane (3.7 mL, 23.1 mmol) was added. After stirring at ambient temperature overnight, the reaction was concentrated. The residue was taken up in ethyl acetate and washed twice with water. The organic phase was thrice extracted with 3 N NaOH and the combined aqueous layers were cooled to 0° C. and acidified with concentrated HCl to pH~1. This acidic aqueous portion was thrice extracted with ethyl acetate and the combined organic layers were washed with water and brine, dried over MgSO₄, filtered and concentrated. Acid 75 was isolated as a yellow solid (1.06 g, 70%) and used without further purification.

Acid 75 (0.204 g, 1.04 mmol) was dissolved in DCM (5 mL) and treated with oxalyl chloride (0.9 mL, 10.4 mmol) and 1 drop DMF. After stirring for 1 hour at ambient temperature this reaction was thrice concentrated from DCM. The isolated red-brown oil was taken up in dichloroethane (26 mL) and cooled to 0° C. Aluminum chloride (0.277 g, 2.08 mmol) was added in portions. After stirring at 0° C. for 1 hour the reaction was quenched by the dropwise addition of water and 1 N aqueous HCl. This aqueous portion was thrice extracted with Ethyl acetate and the combined organic layers were washed with saturated aq. NaHCO₃ and brine, dried over MgSO₄, filtered and concentrated. The crude brown oil was purified using silica gel column chromatography (0-2% ethyl acetate-hexanes) yielding ketone 76 as a yellow oil (0.122 g, 66%).

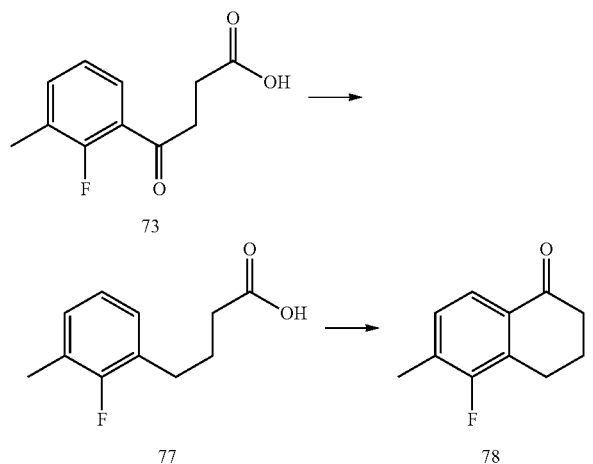

Compounds such as 73 were prepared using Synthetic Method U. Keto-acid 73 (0.433 g, 2.06 mmol) was dissolved in THF (12 mL) and 2 drops of concentrated sulfuric acid were added. 10% Palladium on carbon (50% wetted, 0.150 g, 35 mol %) was added and the flask was sealed. The flask was evacuated and backfilled three times with nitrogen, and then evacuated and backfilled three times with hydrogen; hydrogen was added to the flask until the pressure reached 50 psi. After 68 hours, the catalyst was filtered off using Celite and ethyl acetate. The filtrate was washed with water and brine, dried over MgSO₄, filtered and concentrated, yielding acid 77 as a yellow oil (0.333 g, 83%), which was used without further purification.

Acid 77 (0.320 g, 0.163 mmol) was dissolved in DCM (8.5 mL) and treated with oxalyl chloride (1.5 mL, 16.3 mmol) and 1 drop DMF. After stirring for 1 hour at ambient temperature this reaction was thrice concentrated from DCM. The isolated clear yellow-brown oil (0.419 g, quant.) was taken up in dichloromethane (48 mL) and cooled to 0° C. Aluminum chloride (0.435 g, 3.26 mmol) was then added in portions. The reaction slowly warmed to room temperature with stirring overnight and was quenched by dropwise addition of water and 1 N aqueous HCl. This aqueous phase was thrice extracted with ethyl acetate and the combined organic phase was washed with saturated aq. NaHCO₃ and brine, dried over MgSO₄, filtered and concentrated. The crude yellow-brown oil was purified by silica gel column chromatography (0-2% ethyl acetate-hexanes) yielding ketone 78 as a yellow oil (0.171 g, 59%).

6.27. Synthetic Method W: Preparation of ethyl 6-amino-7-methyl-4,5-dihydronaphtho[1,2-b]thiophene-2-carboxylate (Scheme 32)

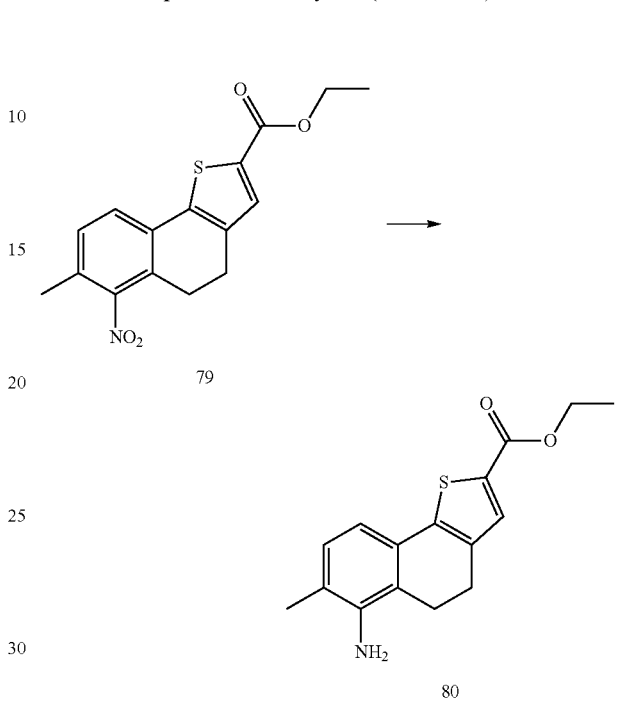

Nitro-ester 79 (0.2060 g, 0.6491 mmol) was dissolved in ethyl acetate (6.5 mL). 10% palladium on carbon (50% wet, 0.0412 g, 10 mol %) was added and the flask was sealed. The flask was evacuated and backfilled three times with nitrogen, and then evacuated and backfilled three times with hydrogen (via balloon). Hydrogen was bubbled through the reaction for 5 minutes and the reaction was heated to 55° C. After 6 hours at 55° C., more 10% palladium on carbon (50% wet, 0.0412 g, 10 mol %) was added and the reaction was equipped with a fresh hydrogen balloon, following the same evacuation/backfilling/purging procedure used previously. The reaction was heated at 55° C. overnight. The catalyst was filtered off using Celite with ethyl acetate. The filtrate was concentrated, yielding 80 as a yellow-brown solid (0.190 g, quant.).

6.28. Method X: Preparation of Ethyl 6-cyano-7-methyl-4,5-dihydronaphtho[1,2-b]thiophene-2-carboxylate

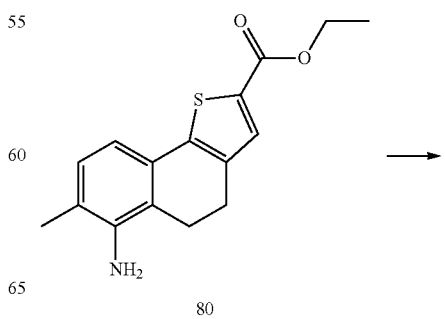

-continued

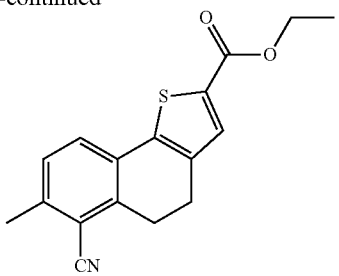

81

Method 1: Aniline 80 (0.129 g, 0.448 mmol) was taken up in water (0.6 mL) and concentrated HCl (0.3 mL) and cooled to 0° C. A solution of sodium nitrite (0.040 g, 0.584 mmol) in water (0.3 mL) was added and the reaction stirred at 0° C. for 10 minutes. After the stirring period, a solution of copper (I) cyanide (0.048 g, 0.538 mmol) and sodium cyanide (0.075 g, 1.52 mmol) in water (0.6 mL) was added dropwise to the reaction flask. After stirring at 0° C. for 30 minutes, the reaction was heated at 60° C. for 30 minutes. The reaction was diluted with water and thrice extracted with ethyl acetate. The combined organic layers were washed with water and brine, dried over MgSO$_4$, filtered and concentrated. The crude dark orange oil was purified by silica gel column chromatography (0-5% ethyl acetate-hexanes), yielding nitrile 81 as a pale yellow solid (0.010 g, 8%).

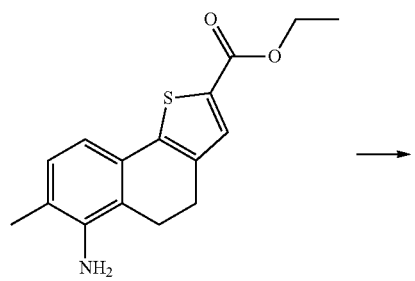

80

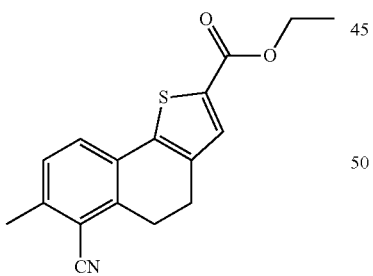

81

Method 2: Copper (I) cyanide (0.014 g, 0.156 mmol) was taken up in dry DMSO (0.2 mL) and warmed to 60° C. t-Butylnitrite (50.6 µL, 0.426 mmol) was added in one portion. A solution of ethyl 6-amino-7-methyl-4,5-dihydronaphtho[1,2-b]thiophene-2-carboxylate 80 (0.041 g, 0.142 mmol) in DMSO (0.2 mL) was then added dropwise and the reaction stirred at 60° C. for 1 hour. The reaction was cooled to 45° C. and 5 M aqueous HCl was slowly added. After cooling to room temperature, the reaction was diluted with water and thrice extracted with ethyl acetate. The combined organic layers were washed with water and brine, dried over MgSO$_4$, filtered and concentrated. The crude yellow orange solid was purified by silica gel column chromatography (0-3% ethyl acetate-hexanes) yielding 81 as an off white solid (0.0082 g, 19%), which was contaminated with ~10% (by NMR) of the fully aromatic byproduct (ethyl 6-cyano-7-methylnaphtho[1,2-b]thiophene-2-carboxylate).

6.29. Method Y: Preparation of 6-Chloro-3,4-dihydronaphthalen-1(2H)-one

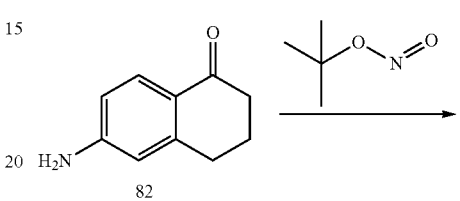

Under N$_2$, t-butyl nitrite (0.954 g, 9.30 mmol) was added drop-wise at room temperature to a stirred suspension of copper (II) chloride (1.00 g, 7.44 mmol) in acetonitrile (10 mL). The suspension was heated to 60° C., aniline 82 was added and the reaction was stirred at 60° C. for 30 minutes. The reaction was cooled to room temperature, diluted with diethyl ether, washed successively with 1N HCl, H$_2$O (3×), and brine. The organic layer was dried over MgSO$_4$ and concentrated in vacuo to give crude product as brown oil. The mixture was purified by silica gel column chromatography (ethyl acetate-hexanes gradient) to give chloride 83 (0.785 g, 70%) as a clear oil.

6.30. Method Z: Preparation of 6-Bromo-3,4-dihydronaphthalen-1(2H)-one

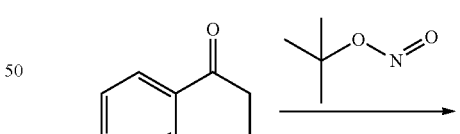

83

68

Under N$_2$, t-butyl nitrite (2.05 g, 19.9 mmol) was added dropwise at room temperature to a stirred suspension of copper (II) bromide (3.56 g, 15.9 mmol) in acetonitrile (60 mL). The suspension was heated to 60° C., aniline 83 was added to the reaction then stirred at 60° C. overnight. The reaction was cooled to room temperature, quenched with 2N HCl (200 mL) then extracted thrice with diethyl ether. The combined organic layers were washed with brine, dried over MgSO$_4$ and concentrated in vacuo to give crude product as black oil. The mixture was purified by silica gel column chromatography (ethyl acetate-hexanes gradient) to give bromide 68 (0.820 g, 27% yield) as a white solid.

6.31. Method AA: Preparation of 6-(Methylamino)-3,4-dihydronaphthalen-1(2H)-one and 6-(dimethyl-amino)-3,4-dihydronaphthalen-1(2H)-one

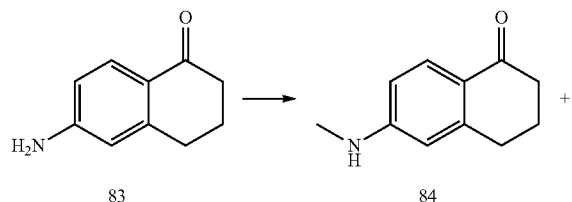

To a solution of aniline 83 (0.4 g, 2.5 mmol) in methanol was added iodomethane (232 µL, 3.7 mmol) and sodium carbonate (1.05 g, 10 mmol) and the reaction stirred at 62° C. for 18 h. The reaction was filtered and concentrated in vacuo. The crude residue was purified by silica gel chromatography (ethyl acetate-hexanes gradient) to give an inseparable mixture of 84 and 85 (0.32 g) which were used as a mixture in the next step.

6.32. Method AB: Preparation of 4-(2,3-dichlorophenoxy) butanoic acid

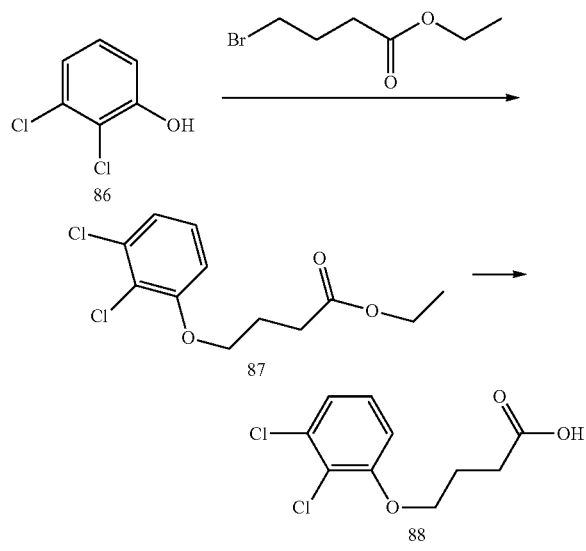

A solution of 2.74 g 2,3-dichlorophenol (2.74 g, 16.8 mmol), ethyl 4-bromobutanoate (2.6 mL, 18.5 mmol) K$_2$CO$_3$ (2.31 g, 16.8 mmol) in 20 ml DMF was stirred at 100° C. for 1 hour. LC-MS showed the completion of the reaction. Added H$_2$O to the reaction mixture, product separated from aqueous phase and stayed on the bottom of the flask. Concentrated the aqueous phase to recover 87 as an oil (3.5 g).

The mixture of 1.8 g ethyl 4-(2,3-dichlorophenoxy) butanoate (1.8 g, 6.50 mmol), 5 ml 5N NaOH (excess), and 5 ml THF was stirred at 60° C. for 2 hours. LC-MS showed the completion of the reaction. 1N HCl was added to neutralize the reaction mixture and was then extracted with ethyl acetate. The organic phase dried over Na$_2$SO$_4$ and concentrated in vacuo to afford 88 a white solid (1.1 g). Intermediates could be further elaborated to final products by using General Method A.

6.33. Method AC: Preparation of -chloro-4,5-dihydrobenzo[1,2-b:6,5-b']dithiophene-2-carboxylic acid

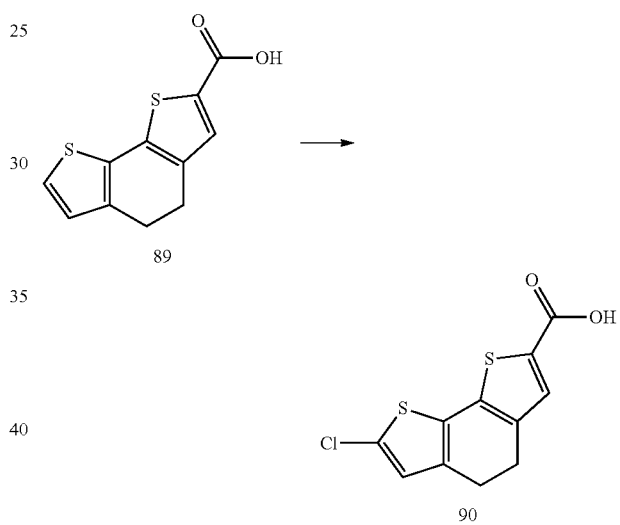

Compound 89 was prepared by General Method B. A mixture of mg 4,5-dihydrobenzo[1,2-b:6,5-b']dithiophene-2-carboxylic acid (100 mg, 0.42 mmol), NCS (83 mg, 0.63 mmol), and 1.5 ml THF was stirred at 55° C. for 1.5 hour. The reaction was followed by LC-MS. Upon completion of the reaction, the mixture was purified by Prep HPLC, to recover 90 as a white solid (15 mg).

6.34. Additional Compounds

Numerous compounds were made and tested for their activity in one or more of the assays described herein. Some of those compounds are listed below in Table 1, in which the column "Prep" indicates the general synthetic method used to make the named compound (the symbol "†" indicates that the compound was obtained commercially). The column "HPLC Method & Time (min)" refers to the following HPLC conditions:

A: Sunfire C (18 5 µm 4.6×50 mm, 10% to 90% B, gradient time=2 min, flow rate=3.5 mL/min, wavelength=220 and 254 nm, solvent A=10 mM aqueous ammonium acetate, solvent B=acetonitrile.

B: Sunfire C (18 3.5 μm 4.6×50 mm, 5% to 100% B, gradient time=4 min, flow rate=3 mL/min, wavelength=220 and 254 nm, solvent A=water with 0.1% trifluoroacetic acid, solvent B=95% methanol/5% water with 0.1% trifluoroacetic acid (v/v).

C: Sunfire C (18 3.5 μm 4.6×50 mm, 10% to 90% B, gradient time=2 min, flow rate=3 mL/min, wavelength=220 and 254 nm, solvent A=10 mM aqueous ammonium acetate, solvent B=acetonitrile.

D: X-Bridge RP18 3.5 μm 4.6×50 mm, 10% to 90% B, gradient time=2 min, flow rate=3.5 mL/min, wavelength=220 and 254 nm, solvent A=10 mM aqueous ammonium acetate, solvent B=acetonitrile.

E: X-Bridge RP18 3.5 μm 4.6×50 mm, 10% to 90% B, gradient time=2 min, flow rate=3.5 mL/min, wavelength=220 and 254 nm, solvent A=in house carbon filtered nanopure water, solvent B=95% methanol/5% water with 0.1% trifluoroacetic acid (v/v).

F: Sunfire C (18 5 μm 4.6×50 mm, 10% to 90% B, gradient time=2 min, flow rate=3.5 mL/min, wavelength=254 and 280 nm, solvent A=purified water, solvent B=95% methanol/5% water with 0.1% trifluoroacetic acid (v/v).

G: Sunfire C (18 3.5 μm 4.6×50 mm, 5% to 100% B, gradient time=4 min, flow rate=3 mL/min, wavelength=220 and 254 nm, solvent A=10 mM aqueous ammonium acetate, solvent B=acetonitrile H: Sunfire C (18 3.5 μm 4.6×50 mm, 10% to 90% B, gradient time=2 min, flow rate=3 ml/min, wavelength=220 and 254. Solvent A=10 mM aqueous ammonium formate (aq.), solvent B=acetonitrile.

I: Sunfire C (18 3.5 μm 4.6×50 mm, 10% to 90% B, gradient time=6 min, flow rate=3 ml/min, wavelength=220 and 254. Solvent A=10 mM aqueous ammonium formate (aq.), solvent B=acetonitrile.

J: Sunfire C (18 3.5 μm 4.6×50 mm, 10% to 90% B, gradient time=4 min, flow rate=3 ml/min, wavelength=220 and 254. Solvent A=10 mM aqueous ammonium formate (aq.), solvent B=acetonitrile.

K: Sunfire C (18 3.5 μm 4.6×50 mm, 10% to 90% B, gradient time=2 min, flow rate=3.5 ml/min, wavelength=220 and 254. Solvent A=10 mM aqueous ammonium formate (aq.), solvent B=acetonitrile.

L: Sunfire C (18 3.5 μm 4.6×50 mm, 10% to 90% B, gradient time=4 min, flow rate=3 mL/min, wavelength=220 and 254 nm, solvent A=10 mM aqueous ammonium acetate, solvent B=acetonitrile.

The column "$IC_{50}$" provides the compounds' $IC_{50}$ as measured using the binding assay described herein, wherein: ** means a value of less than or equal to 0.05 μM; * means a value of less than or equal to 0.1 μM; ** means a value of less than or equal to 1.0 μM; * means a value of less than or equal to 2.0 μM; and—means that the $IC_{50}$ was not determined. The column "$EC_{50}$" provides the compounds' $EC_{50}$ as measured using the reporter assay described herein, wherein: ** means a value of less than or equal to 0.05 μM; * means a value of less than or equal to 0.1 μM; ** means a value of less than or equal to 0.5 μM; * means a value of less than or equal to 1.0 μM; and—means that the $EC_{50}$ was not determined.

TABLE 1

| Compound | Prep | HPLC Method & Time (min) | Purity (%) | $IC_{50}$ | $EC_{50}$ |
| --- | --- | --- | --- | --- | --- |
| N-methyl-4,5-dihydronaphtho[1,2-b]thiophene-2-carboxamide | † | n/a | 90 | *** | **** |
| N,N-dimethyl-4,5-dihydronaphtho[1,2-b]thiophene-2-carboxamide | † | n/a | 90 | ** | **** |
| methyl 4,5-dihydronaphtho[1,2-b]thiophene-2-carboxylate | † | n/a | 90 | ** | **** |
| N-cyclopropyl-4,5-dihydronaphtho[1,2-b]thiophene-2-carboxamide | † | n/a | 90 | >2 | **** |
| methyl 4H-thieno[3,2-c]chromene-2-carboxylate | † | — | 97 | ** | — |
| ethyl 8-fluoro-4H-thieno[3,2-c]chromene-2-carboxylate | † | — | 97 | >2 | — |
| 8-methyl-4H-thieno[3,2-c]chromene-2-carboxylic acid | A | A (1.433) | 100 | ** | **** |
| 6-chloro-4,5-dihydronaphtho[1,2-b]thiophene-2-carboxylic acid | B | A (1.802) | 100 | *** | **** |
| 6-chloro-4,5-dihydronaphtho[1,2-b]thiophene-2-carboxamide | I | A (2.14) | 98.5 | ** | **** |
| 8-bromo-5,5-dimethyl-4,5-dihydronaphtho[1,2-b]thiophene-2-carboxylic acid | B | A (2.027) | 99.1 | >2 | — |
| 6-bromo-7-methoxy-4,5-dihydronaphtho[1,2-b]thiophene-2-carboxylic acid | F, B | A (1.68) | 99 | **** | **** |
| 6-chloro-4H-thieno[3,2-c]chromene-2-carboxylic acid | A | A (1.625) | 99 | ** | **** |
| 6-methoxy-4H-thieno[3,2-c]chromene-2-carboxylic acid | A | A (1.397) | 98.3 | >2 | ** |
| 6-fluoro-4H-thieno[3,2-c]chromene-2-carboxylic acid | A | A (1.5) | 93.6 | ** | **** |
| 6-methyl-4H-thieno[3,2-c]chromene-2-carboxylic acid | A | A (1.617) | 97.7 | * | **** |
| 6,8-difluoro-4H-thieno[3,2-c]chromene-2-carboxylic acid | A | A (1.35) | 99.7 | **** | **** |
| 6,7-dichloro-4H-thieno[3,2-c]chromene-2-carboxylic acid | A | A (1.515) | 98.3 | **** | **** |

TABLE 1-continued

| Compound | Prep | HPLC Method & Time (min) | Purity (%) | IC$_{50}$ | EC$_{50}$ |
|---|---|---|---|---|---|
| 7,9-dimethyl-4H-thieno[3,2-c]chromene-2-carboxylic acid | A | A (1.902) | 99.6 | >2 | **** |
| 6,8-dimethyl-4H-thieno[3,2-c]chromene-2-carboxylic acid | A | A (1.752) | 99.6 | ** | **** |
| 6-chloro-4H-thieno[3,2-c]chromene-2-carboxamide | A | A (2.043) | 99.8 | ** | **** |
| 6-fluoro-4H-thieno[3,2-c]chromene-2-carboxamide | I | A (1.895) | 99.9 | **** | **** |
| 6-methyl-4H-thieno[3,2-c]chromene-2-carboxamide | I | A (2.052) | 98.6 | ** | **** |
| 6,8-difluoro-4H-thieno[3,2-c]chromene-2-carboxamide | I | A (2.003) | 99.9 | **** | **** |
| 7,9-dimethyl-4H-thieno[3,2-c]chromene-2-carboxamide | I | A (2.13) | 99.1 | * | **** |
| 6,8-dimethyl-4H-thieno[3,2-c]chromene-2-carboxamide | I | A (2.152) | 99.9 | * | **** |
| 6,7-dichloro-4H-thieno[3,2-c]chromene-2-carboxamide | I | A (2.175) | 97 | *** | **** |
| 8-nitro-4H-thieno[3,2-c]chromene-2-carboxylic acid | A | A (1.302) | 99.6 | ** | **** |
| 7,8-dichloro-4,5-dihydronaphtho[1,2-b]thiophene-2-carboxylic acid | B | A (1.59) | 97.1 | *** | **** |
| 7,8-dichloro-4,5-dihydronaphtho[1,2-b]thiophene-2-carboxamide | I | A (2.433) | 99.9 | ** | **** |
| 7-chloro-6-fluoro-4H-thieno[3,2-c]chromene-2-carboxylic acid | A | A (1.488) | 98.9 | *** | **** |
| 6-bromo-8-chloro-4H-thieno[3,2-c]chromene-2-carboxylic acid | A | A (1.608) | 98.9 | ** | **** |
| 7-cyano-4H-thieno[3,2-c]chromene-2-carboxamide | I | A (1.622) | 97.9 | >2 | >1 |
| 7-chloro-6-fluoro-4H-thieno[3,2-c]chromene-2-carboxamide | I | A (1.938) | 96.2 | **** | **** |
| 6-chloro-7-methoxy-4,5-dihydronaphtho[1,2-b]thiophene-2-carboxylic acid | D, B | A (1.51) | 98.3 | **** | **** |
| 7-methoxy-4H-thieno[3,2-c]chromene-2-carboxylic acid | A | A | 97 | * | *** |
| 6-fluoro-4,5-dihydronaphtho[1,2-b]thiophene-2-carboxylic acid | B | A (1.355) | 95.3 | **** | **** |
| 8-bromo-4H-thieno[3,2-c]chromene-2-carboxylic acid | A | A (1.403) | 99.7 | *** | **** |
| 7,8-difluoro-4H-thieno[3,2-c]chromene-2-carboxylic acid | A | A (1.362) | 99 | *** | **** |
| 6-fluoro-7-methoxy-4,5-dihydronaphtho[1,2-b]thiophene-2-carboxylic acid | E, B | A (3.69) | 97 | *** | **** |
| 7-methoxy-4H-thieno[3,2-c]chromene-2-carboxamide | I | A (1.713) | 96.9 | ** | *** |
| 6-fluoro-4,5-dihydronaphtho[1,2-b]thiophene-2-carboxamide | I | A (1.873) | 100 | **** | **** |
| 8-bromo-4H-thieno[3,2-c]chromene-2-carboxamide | I | A (1.957) | 98.7 | ** | **** |
| 7,8-difluoro-4H-thieno[3,2-c]chromene-2-carboxamide | I | A (1.882) | 99.2 | *** | **** |
| 6-bromo-7-methoxy-4,5-dihydronaphtho[1,2-b]thiophene-2-carboxamide | I | A (1.975) | 98.1 | **** | **** |
| 6-chloro-7-methoxy-4,5-dihydronaphtho[1,2-b]thiophene-2-carboxamide | I | A (1.94) | 98.3 | **** | **** |
| 6-cyano-7-methoxy-4,5-dihydronaphtho[1,2-b]thiophene-2-carboxylic acid | F, B | A (1.696) | 99.2 | **** | **** |
| 6-chloro-7-methoxy-N-(2-methoxyethyl)-4,5-dihydronaphtho[1,2-b]thiophene-2-carboxamide | I | A (2.812) | 98.6 | ** | **** |
| 6-chloro-N-(2-hydroxyethyl)-7-methoxy-4,5-dihydronaphtho[1,2-b]thiophene-2-carboxamide | I | A (1.992) | 99.4 | ** | **** |
| N-(2-(1H-tetrazol-5-yl)ethyl)-6-chloro-7-methoxy-4,5-dihydronaphtho[1,2-b]thiophene-2-carboxamide | I | A (1.67) | 100 | ** | **** |
| 6-chloro-N-(2-cyanoethyl)-7-methoxy-4,5-dihydronaphtho[1,2-b]thiophene-2-carboxamide | I | A (2.158) | 99.9 | ** | **** |

TABLE 1-continued

| Compound | Prep | HPLC Method & Time (min) | Purity (%) | IC$_{50}$ | EC$_{50}$ |
|---|---|---|---|---|---|
| 6-chloro-7-methoxy-N-(2-morpholinoethyl)-4,5-dihydronaphtho[1,2-b]thiophene-2-carboxamide | I | A (2.058) | 99.7 | ** | **** |
| 7-fluoro-4,5-dihydronaphtho[1,2-b]thiophene-2-carboxylic acid | B | A (1.457) | 97.1 | ** | **** |
| 6-fluoro-N-(2-methoxyethyl)-4,5-dihydronaphtho[1,2-b]thiophene-2-carboxamide | I | A (1.933) | 100 | *** | **** |
| 7-fluoro-4,5-dihydronaphtho[1,2-b]thiophene-2-carboxamide | I | A (1.728) | 100 | **** | **** |
| N-(2-cyanoethyl)-6-fluoro-4,5-dihydronaphtho[1,2-b]thiophene-2-carboxamide | I | A (1.897) | 100 | *** | *** |
| N-(2-(1H-tetrazol-5-yl)ethyl)-6-fluoro-4,5-dihydronaphtho[1,2-b]thiophene-2-carboxamide | I | A (1.335) | 100 | ** | **** |
| 6-fluoro-N-(2-hydroxyethyl)-4,5-dihydronaphtho[1,2-b]thiophene-2-carboxamide | I | A (1.667) | 100 | ** | **** |
| 6-cyano-7-methoxy-4,5-dihydronaphtho[1,2-b]thiophene-2-carboxamide | I | A (1.563) | 97.4 | ** | **** |
| 7-(trifluoromethyl)-4H-thieno[3,2-c]chromene-2-carboxylic acid | H, A | A (1.755) | 94.6 | — | — |
| N-(2-(1H-imidazol-1-yl)ethyl)-6-fluoro-4,5-dihydronaphtho[1,2-b]thiophene-2-carboxamide | I | A (1.697) | 97.2 | >2 | ** |
| 6-fluoro-N-(oxazol-2-ylmethyl)-4,5-dihydronaphtho[1,2-b]thiophene-2-carboxamide | I | A (1.872) | 100 | *** | **** |
| 6,8-difluoro-4,5-dihydronaphtho[1,2-b]thiophene-2-carboxylic acid | B | A (1.498) | 98.8 | ** | **** |
| 6,7-difluoro-4H-thieno[3,2-c]chromene-2-carboxylic acid | A | A (1.303) | 97.1 | ** | **** |
| 6-fluoro-7-methoxy-4,5-dihydronaphtho[1,2-b]thiophene-2-carboxamide | I | A (1.685) | 96.1 | *** | **** |
| 6,8-difluoro-4,5-dihydronaphtho[1,2-b]thiophene-2-carboxamide | I | A (1.728) | 100 | **** | **** |
| 6,7-difluoro-4H-thieno[3,2-c]chromene-2-carboxamide | I | A (1.667) | 98.1 | **** | **** |
| 7,8-difluoro-4,5-dihydronaphtho[1,2-b]thiophene-2-carboxylic acid | A | A (2.067) | 98.1 | **** | **** |
| 9-(trifluoromethyl)-4H-thieno[3,2-c]chromene-2-carboxylic acid | H, A | A (1.567) | 95.1 | ** | **** |
| 8-isopropyl-4H-thieno[3,2-c]chromene-2-carboxylic acid | A | A (1.827) | 95.6 | >2 | *** |
| 6-chloro-9-methyl-4H-thieno[3,2-c]chromene-2-carboxylic acid | A | A (1.603) | 94.9 | ** | **** |
| 8-cyano-7-methoxy-4,5-dihydronaphtho[1,2-b]thiophene-2-carboxylic acid | F, B | A (1.163) | 97.7 | >2 | >1 |
| 7,8-difluoro-4,5-dihydronaphtho[1,2-b]thiophene-2-carboxamide | I | A (1.773) | 100 | **** | **** |
| 9-(trifluoromethyl)-4H-thieno[3,2-c]chromene-2-carboxamide | I | A (1.757) | 100 | **** | **** |
| 8-isopropyl-4H-thieno[3,2-c]chromene-2-carboxamide | I | A (1.945) | 100 | >2 | * |
| 6-cyano-4H-thieno[3,2-c]chromene-2-carboxylic acid | A | A (1.312) | 95 | *** | **** |
| 6,7-difluoro-4,5-dihydronaphtho[1,2-b]thiophene-2-carboxylic acid | B | A (1.308) | 99.6 | **** | **** |
| 6,9-dimethyl-4H-thieno[3,2-c]chromene-2-carboxylic acid | A | A (1.358) | 96.5 | * | **** |
| 8-bromo-6-chloro-4H-thieno[3,2-c]chromene-2-carboxylic acid | A | A (1.432) | 97.8 | **** | **** |
| 6-chloro-9-methyl-4H-thieno[3,2-c]chromene-2-carboxamide | I | A (1.812) | 98.9 | **** | **** |
| 7-chloro-4H-thieno[3,2-c]chromene-2-carboxylic acid | A | A (1.362) | 97.7 | *** | **** |
| 8-chloro-6-fluoro-4H-thieno[3,2-c]chromene-2-carboxylic acid | A | A (1.333) | 99 | **** | **** |
| 7-fluoro-6-methyl-4H-thieno[3,2-c]chromene-2-carboxylic acid | A | A (1.333) | 99.6 | ** | **** |
| 6-cyano-4H-thieno[3,2-c]chromene-2-carboxamide | I | A (1.492) | 95.1 | ** | **** |

TABLE 1-continued

| Compound | Prep | HPLC Method & Time (min) | Purity (%) | IC$_{50}$ | EC$_{50}$ |
|---|---|---|---|---|---|
| 6,7-difluoro-4,5-dihydronaphtho[1,2-b]thiophene-2-carboxamide | I | A (1.793) | 98.2 | **** | **** |
| 6,9-dimethyl-4H-thieno[3,2-c]chromene-2-carboxamide | I | A (1.823) | 99.6 | *** | **** |
| 8-bromo-6-chloro-4H-thieno[3,2-c]chromene-2-carboxamide | I | A (2.013) | 96.7 | ** | **** |
| 7-chloro-4H-thieno[3,2-c]chromene-2-carboxamide | I | A (1.805) | 99.8 | *** | **** |
| 8-chloro-6-fluoro-4H-thieno[3,2-c]chromene-2-carboxamide | I | A (1.825) | 99.6 | *** | **** |
| 7-fluoro-6-methyl-4H-thieno[3,2-c]chromene-2-carboxamide | I | A (1.807) | 97 | **** | **** |
| 6,9-dichloro-4H-thieno[3,2-c]chromene-2-carboxylic acid | A | A (1.337) | 95.7 | *** | **** |
| 6-cyano-7-fluoro-4,5-dihydronaphtho[1,2-b]thiophene-2-carboxylic acid | B | A (1.225) | 100 | **** | **** |
| 6,9-dichloro-4H-thieno[3,2-c]chromene-2-carboxamide | I | A (1.852) | 94.3 | **** | **** |
| 7-(methylamino)-4,5-dihydronaphtho[1,2-b]thiophene-2-carboxylic acid | AA, B, B | A (1.17) | 95 | * | **** |
| 7-(dimethylamino)-4,5-dihydronaphtho[1,2-b]thiophene-2-carboxylic acid | AA, B, B | A (1.318) | 96.3 | * | ** |
| 8-cyano-7-fluoro-4H-thieno[3,2-c]chromene-2-carboxylic acid | A | A (1.228) | 99.9 | >2 | *** |
| 7-fluoro-4H-thieno[3,2-c]chromene-2-carboxylic acid | A | A (1.203) | 99 | * | **** |
| 1-(6,7-dichloro-4H-thieno[3,2-c]chromene-2-carbonyl)pyrrolidine-3-carbonitrile | I | A (2.132) | 96.5 | *** | **** |
| 9-fluoro-4H-thieno[3,2-c]chromene-2-carboxylic acid | A | A (1.182) | 98.4 | ** | **** |
| 8-chloro-7-(trifluoromethyl)-4H-thieno[3,2-c]chromene-2-carboxylic acid | A | A (1.498) | 96.7 | ** | **** |
| (6,7-dichloro-4H-thieno[3,2-c]chromen-2-yl)(3-fluoropyrrolidin-1-yl)methanone | I | A (2.225) | 99.1 | ** | **** |
| 8-chloro-7-(trifluoromethyl)-4H-thieno[3,2-c]chromene-2-carboxamide | I | A (2.032) | 98.1 | >2 | ** |
| (6-chloro-7-methoxy-4,5-dihydronaphtho[1,2-b]thiophen-2-yl)(3-fluoropyrrolidin-1-yl)methanone | I | A (2.108) | 100 | **** | **** |
| 1-(6-chloro-7-methoxy-4,5-dihydronaphtho[1,2-b]thiophene-2-carbonyl)pyrrolidine-3-carbonitrile | I | A (2.013) | 100 | *** | **** |
| 9-fluoro-4H-thieno[3,2-c]chromene-2-carboxamide | I | A (1.61) | 100 | **** | **** |
| (6-fluoro-4,5-dihydronaphtho[1,2-b]thiophen-2-yl)(3-fluoropyrrolidin-1-yl)methanone | I | A (2.048) | 100 | ** | **** |
| 1-(6-fluoro-4,5-dihydronaphtho[1,2-b]thiophene-2-carbonyl)pyrrolidine-3-carbonitrile | I | A (1.958) | 100 | *** | **** |
| 1-(6,7-dichloro-4H-thieno[3,2-c]chromene-2-carbonyl)pyrrolidin-3-one | I | A (2.062) | 98.7 | *** | **** |
| 7,9-difluoro-4H-thieno[3,2-c]chromene-2-carboxylic acid | A | A (1.252) | 97.2 | * | — |
| 7,8,9-trifluoro-4H-thieno[3,2-c]chromene-2-carboxylic acid | A | A (1.335) | 99.9 | **** | **** |
| 8-chloro-6-methyl-4H-thieno[3,2-c]chromene-2-carboxylic acid | A | A (1.455) | 98.4 | ** | **** |
| rac-1-(6,7-dichloro-4H-thieno[3,2-c]chromene-2-carbonyl)-4-(2-fluorophenyl)pyrrolidine-3-carboxylic acid | I | A (2.088) | 95.9 | **** | **** |
| 6,9-difluoro-4H-thieno[3,2-c]chromene-2-carboxylic acid | A | A (1.19) | 98.4 | *** | **** |
| 6-chloro-9-fluoro-4H-thieno[3,2-c]chromene-2-carboxylic acid | A | A (1.293) | 96.9 | ** | **** |
| 7,9-difluoro-4H-thieno[3,2-c]chromene-2-carboxamide | I | A (1.728) | 100 | **** | **** |

TABLE 1-continued

| Compound | Prep | HPLC Method & Time (min) | Purity (%) | IC$_{50}$ | EC$_{50}$ |
|---|---|---|---|---|---|
| 7,8,9-trifluoro-4H-thieno[3,2-c]chromene-2-carboxamide | I | A (1.76) | 100 | **** | **** |
| 6,9-difluoro-4H-thieno[3,2-c]chromene-2-carboxamide | I | A (1.618) | 99.7 | **** | — |
| 6-chloro-9-fluoro-4H-thieno[3,2-c]chromene-2-carboxamide | I | A (1.755) | 100 | **** | **** |
| 7-(dimethylamino)-4,5-dihydronaphtho[1,2-b]thiophene-2-carboxamide | I | A (1.758) | 99 | * | — |
| 8-chloro-6-methyl-4H-thieno[3,2-c]chromene-2-carboxamide | I | A (1.933) | 100 | ** | **** |
| (6-chloro-7-methoxy-4,5-dihydronaphtho[1,2-b]thiophen-2-yl)(3-methoxypyrrolidin-1-yl)methanone | I | A (2.085) | 100 | **** | **** |
| (6-fluoro-4,5-dihydronaphtho[1,2-b]thiophen-2-yl)(3-methoxypyrrolidin-1-yl)methanone | I | A (2.063) | 100 | **** | **** |
| 6-chloro-8-methyl-4,5-dihydronaphtho[1,2-b]thiophene-2-carboxylic acid | B | A (1.503) | 95.5 | **** | **** |
| 6-chloro-8-methyl-4,5-dihydronaphtho[1,2-b]thiophene-2-carboxamide | I | A (2.063) | 100 | **** | **** |
| (6,7-difluoro-4,5-dihydronaphtho[1,2-b]thiophen-2-yl)(3-fluoropyrrolidin-1-yl)methanone | I | A (2.133) | 100 | *** | **** |
| (8-chloro-6-fluoro-4H-thieno[3,2-c]chromen-2-yl)(3-fluoropyrrolidin-1-yl)methanone | I | A (2.142) | 100 | ** | **** |
| 6-fluoro-8-methyl-4H-thieno[3,2-c]chromene-2-carboxylic acid | H, A | A (1.433) | 97.2 | **** | **** |
| 8-chloro-7,9-dimethyl-4H-thieno[3,2-c]chromene-2-carboxylic acid | I | A (1.487) | 98.4 | ** | **** |
| 6-fluoro-8-methoxy-4,5-dihydronaphtho[1,2-b]thiophene-2-carboxylic acid | B | A (1.318) | 97.2 | ** | **** |
| 9-methyl-4H-thieno[3,2-c]chromene-2-carboxylic acid | A | A (1.693) | 100 | >2 | — |
| 4H-thieno[3,2-c]thiochromene-2-carboxylic acid 5,5-dioxide | L | A (1.755) | 100 | **** | **** |
| 8,9-dimethyl-4,5-dihydronaphtho[1,2-b]thiophene-2-carboxylic acid | B | A (1.847) | 100 | * | — |
| 6,7-dimethyl-4,5-dihydronaphtho[1,2-b]thiophene-2-carboxylic acid | B | A (1.788) | 100 | ** | — |
| 7,8-dimethyl-4,5-dihydronaphtho[1,2-b]thiophene-2-carboxylic acid | B | A (1.758) | 99.4 | * | — |
| 4H-thieno[3,2-c]thiochromene-2-carboxylic acid | G, C | A (1.595) | 99.5 | ** | — |
| 8,9-dimethyl-4,5-dihydronaphtho[1,2-b]thiophene-2-carboxamide | I | A (1.857) | 100 | ** | — |
| 6,7-dimethyl-4,5-dihydronaphtho[1,2-b]thiophene-2-carboxamide | I | A (1.782) | 100 | ** | — |
| 7,8-dimethyl-4,5-dihydronaphtho[1,2-b]thiophene-2-carboxamide | I | A (1.777) | 100 | * | — |
| 4H-thieno[3,2-c]thiochromene-2-carboxylic acid 5-oxide | K | A (1.233) | 100 | * | — |
| 4H-thieno[3,2-c]thiochromene-2-carboxamide 5,5-dioxide | I | A (1.6) | 98.5 | ** | **** |
| 8-methyl-4H-thieno[3,2-c]thiochromene-2-carboxylic acid | G, C | A (1.748) | 98.2 | >2 | — |
| 8-chloro-4H-thieno[3,2-c]thiochromene-2-carboxylic acid | G, C | A (1.808) | 96 | * | — |
| 8-methyl-4H-thieno[3,2-c]thiochromene-2-carboxamide | I | A (2.698) | 100 | * | **** |
| 8-chloro-4H-thieno[3,2-c]thiochromene-2-carboxamide | I | A (2.761) | 100 | ** | **** |
| 8-fluoro-4H-thieno[3,2-c]thiochromene-2-carboxylic acid | G, C | A (2.527) | 98 | *** | **** |

TABLE 1-continued

| Compound | Prep | HPLC Method & Time (min) | Purity (%) | IC$_{50}$ | EC$_{50}$ |
|---|---|---|---|---|---|
| 8-fluoro-4H-thieno[3,2-c]thiochromene-2-carboxylic acid 5,5-dioxide | L | A (1.94) | 100 | ** | **** |
| 6-fluoro-4H-thieno[3,2-c]thiochromene-2-carboxylic acid | G, C | A (2.228) | 100 | *** | **** |
| 6-fluoro-4H-thieno[3,2-c]thiochromene-2-carboxylic acid 5,5-dioxide | L | A (1.543) | 100 | *** | **** |
| 8-methoxy-4H-thieno[3,2-c]thiochromene-2-carboxylic acid 5,5-dioxide | G, C, L | A (1.647) | 100 | >2 | ** |
| 6-methoxy-4H-thieno[3,2-c]thiochromene-2-carboxylic acid 5,5-dioxide | G, C, L | A (1.642) | 100 | >2 | * |
| 6,9-dimethyl-4H-thieno[3,2-c]thiochromene-2-carboxylic acid | G, C | A (2.408) | 100 | >2 | **** |
| 6,9-dimethyl-4H-thieno[3,2-c]thiochromene-2-carboxylic acid 5,5-dioxide | L | A (1.885) | 95.6 | >2 | ** |
| 7,8-difluoro-4H-thieno[3,2-c]thiochromene-2-carboxylic acid | G, C | A (2.363) | 100 | *** | **** |
| 7,8-difluoro-4H-thieno[3,2-c]thiochromene-2-carboxylic acid 5,5-dioxide | L | A (1.788) | 99.2 | * | ** |
| 3-amino-4H-thieno[3,2-c]thiochromene-2-carboxylic acid | M | A (1.475) | 94.4 | ** | **** |
| 7-chloro-5,5-dimethyl-4,5-dihydronaphtho[1,2-b]thiophene-2-carboxylic acid | O, C | A (1.525) | 96.1 | * | **** |
| 7,8-difluoro-5,5-dimethyl-4,5-dihydronaphtho[1,2-b]thiophene-2-carboxylic acid | O, C | A (1.502) | 100 | * | **** |
| 4-methyl-4,5-dihydronaphtho[1,2-b]thiophene-2-carboxylic acid | N, C | A (1.352) | 98.3 | * | **** |
| 7,8-difluoro-5-methyl-4,5-dihydronaphtho[1,2-b]thiophene-2-carboxylic acid | P, C | A (1.467) | 99.7 | ** | **** |
| 7,8-difluoro-5-methyl-4,5-dihydronaphtho[1,2-b]thiophene-2-carboxamide | I | A (1.89) | 100 | **** | **** |
| 4-methyl-4,5-dihydronaphtho[1,2-b]thiophene-2-carboxamide | I | A (1.832) | 99.7 | **** | **** |
| 7-chloro-5,5-dimethyl-4,5-dihydronaphtho[1,2-b]thiophene-2-carboxamide | I | A (2.077) | 100 | ** | **** |
| 6,9-difluoro-5-methyl-4,5-dihydronaphtho[1,2-b]thiophene-2-carboxylic acid | P, C | A (1.383) | 98.6 | **** | **** |
| 6,9-difluoro-5-methyl-4,5-dihydronaphtho[1,2-b]thiophene-2-carboxamide | I | A (1.84) | 98.9 | **** | **** |
| 7-chloro-5-methyl-4,5-dihydronaphtho[1,2-b]thiophene-2-carboxylic acid | P, C | A (1.475) | 100 | ** | **** |
| 7-chloro-5-methyl-4,5-dihydronaphtho[1,2-b]thiophene-2-carboxamide | I | A (1.982) | 98.9 | *** | **** |
| 6,8-difluoro-5-methyl-4,5-dihydronaphtho[1,2-b]thiophene-2-carboxylic acid | P, C | A (1.442) | 100 | **** | **** |
| 6,8-difluoro-5-methyl-4,5-dihydronaphtho[1,2-b]thiophene-2-carboxamide | I | A (1.903) | 100 | **** | **** |
| 8-fluoro-5-methyl-4,5-dihydronaphtho[1,2-b]thiophene-2-carboxylic acid | P, C | A (1.348) | 100 | **** | **** |
| 8-fluoro-5-methyl-4,5-dihydronaphtho[1,2-b]thiophene-2-carboxamide | I | A (1.837) | 100 | **** | **** |
| 6,9-difluoro-5,5-dimethyl-4,5-dihydronaphtho[1,2-b]thiophene-2-carboxylic acid | O, C | A (1.43) | 96.2 | ** | **** |
| 6,9-difluoro-5,5-dimethyl-4,5-dihydronaphtho[1,2-b]thiophene-2-carboxamide | I | A (1.962) | 100 | **** | — |

TABLE 1-continued

| Compound | Prep | HPLC Method & Time (min) | Purity (%) | IC$_{50}$ | EC$_{50}$ |
|---|---|---|---|---|---|
| 5-ethyl-6,9-difluoro-4,5-dihydronaphtho[1,2-b]thiophene-2-carboxylic acid | P, C | A (1.457) | 96.7 | ** | **** |
| 5-ethyl-6,9-difluoro-4,5-dihydronaphtho[1,2-b]thiophene-2-carboxamide | I | A (1.968) | 99.1 | **** | **** |
| 6,8-difluoro-4,4-dimethyl-4H-thieno[3,2-c]chromene-2-carboxylic acid | R, C | A (1.39) | 100 | ** | — |
| 6,8-difluoro-4,4-dimethyl-4H-thieno[3,2-c]chromene-2-carboxamide | I | A (1.878) | 100 | ** | ** |
| 7,8-dimethyl-4H-thieno[3,2-c]chromene-2-carboxylic acid | G, A | A (1.375) | 98.6 | ** | **** |
| 7,8-dimethyl-4H-thieno[3,2-c]thiochromene-2-carboxylic acid | G, C | A (1.458) | 100 | >2 | — |
| 7-fluoro-4H-thieno[3,2-c]thiochromene-2-carboxylic acid | G, C | A (1.542) | 99.3 | ** | **** |
| 7,9-difluoro-4H-thieno[3,2-c]thiochromene-2-carboxylic acid | G, C | A (1.377) | 100 | ** | — |
| 8-chloro-7-methyl-4H-thieno[3,2-c]chromene-2-carboxylic acid | G, A | A (1.438) | 98.7 | ** | **** |
| 6-fluoro-7-methyl-4H-thieno[3,2-c]chromene-2-carboxylic acid | G, A | A (1.328) | 98.9 | ** | **** |
| 8-fluoro-6-methyl-4H-thieno[3,2-c]chromene-2-carboxylic acid | G, A | A (1.355) | 100 | *** | **** |
| 8-fluoro-7-methyl-4H-thieno[3,2-c]chromene-2-carboxylic acid | G, A | A (1.343) | 98.4 | *** | **** |
| 8-cyano-4H-thieno[3,2-c]chromene-2-carboxylic acid | G, A | A (1.165) | 99 | >2 | — |
| 8-cyano-6-fluoro-4H-thieno[3,2-c]chromene-2-carboxylic acid | G, A | A (1.232) | 97.4 | ** | — |
| 8-carbamoyl-6-fluoro-4H-thieno[3,2-c]chromene-2-carboxylic acid | G, A | A (0.937) | 100 | >2 | — |
| ethyl 7-methoxy-4,5-dihydronaphtho[1,2-b]thiophene-2-carboxylate | B | G (3.478) | 92.9 | >2 | ** |
| 7-methoxy-4,5-dihydronaphtho[1,2-b]thiophene-2-carboxylic acid | B | G (1.628) | 100 | * | **** |
| ethyl 6-methoxy-4,5-dihydronaphtho[1,2-b]thiophene-2-carboxylate | B | G (3.593) | 87.2 | >2 | ** |
| ethyl 8-methoxy-4,5-dihydronaphtho[1,2-b]thiophene-2-carboxylate | B | G (3.518) | 91.5 | >2 | >1 |
| 6-methoxy-4,5-dihydronaphtho[1,2-b]thiophene-2-carboxylic acid | B | G (1.713) | 100 | >2 | **** |
| 8-methoxy-4,5-dihydronaphtho[1,2-b]thiophene-2-carboxylic acid | B | G (1.712) | 100 | >2 | ** |
| N-hydroxy-4,5-dihydronaphtho[1,2-b]thiophene-2-carboxamide | I | G (2.112) | 96.6 | **** | **** |
| 8-cyano-4,5-dihydronaphtho[1,2-b]thiophene-2-carboxylic acid | S, B | G (1.69) | 97.7 | >2 | * |
| 7-cyano-4,5-dihydronaphtho[1,2-b]thiophene-2-carboxylic acid | Q, B | G (1.577) | 100 | >2 | * |
| 6-cyano-4,5-dihydronaphtho[1,2-b]thiophene-2-carboxylic acid | Q, B | G (1.587) | 97.6 | *** | **** |
| ethyl 7-cyano-4,5-dihydronaphtho[1,2-b]thiophene-2-carboxylate | Q, B | G (3.281) | 100 | >2 | — |
| ethyl 6-cyano-4,5-dihydronaphtho[1,2-b]thiophene-2-carboxylate | Q, B | G (3.295) | 99.6 | >2 | — |
| ethyl 7-methyl-4,5-dihydronaphtho[1,2-b]thiophene-2-carboxylate | T, B | G (3.793) | 99.2 | >2 | — |
| ethyl 7-chloro-4,5-dihydronaphtho[1,2-b]thiophene-2-carboxylate | Y, B | G (3.846) | 99.7 | >2 | — |
| 7-methyl-4,5-dihydronaphtho[1,2-b]thiophene-2-carboxylic acid | T, B | G (1.825) | 98.9 | ** | — |
| 7-chloro-4,5-dihydronaphtho[1,2-b]thiophene-2-carboxylic acid | Y, B | G (1.905) | 97.3 | ** | — |
| 7-bromo-4,5-dihydronaphtho[1,2-b]thiophene-2-carboxylic acid | Z, B | G (2) | 97.1 | ** | **** |
| 9-bromo-4,5-dihydronaphtho[1,2-b]thiophene-2-carboxylic acid | B | G (1.808) | 100 | >2 | — |

TABLE 1-continued

| Compound | Prep | HPLC Method & Time (min) | Purity (%) | IC$_{50}$ | EC$_{50}$ |
| --- | --- | --- | --- | --- | --- |
| 9-cyano-4,5-dihydronaphtho[1,2-b]thiophene-2-carboxylic acid | B | G (1.63) | 100 | >2 | — |
| 4,5-dihydronaphtho[1,2-b]thiophene-2-carboxylic acid | B | L (1.35) | 100 | ** | **** |
| ethyl 4,5-dihydronaphtho[1,2-b]thiophene-2-carboxylate | B | L (3.713) | 96.5 | * | **** |
| tert-butyl (2-(4,5-dihydronaphtho[1,2-b]thiophene-2-carboxamido)ethyl)carbamate | I | L (2.906) | 98.5 | * | **** |
| N-(2-aminoethyl)-4,5-dihydronaphtho[1,2-b]thiophene-2-carboxamide | J | L (1.483) | 100 | * | ** |
| 8-methyl-4H-thieno[3,2-c]chromene-2-carboxylic acid | A | L (1.385) | 94.9 | — | — |
| N-(2-hydroxyethyl)-4,5-dihydronaphtho[1,2-b]thiophene-2-carboxamide | I | L (2.02) | 100 | ** | **** |
| N-(2-(dimethylamino)ethyl)-4,5-dihydronaphtho[1,2-b]thiophene-2-carboxamide | I | L (1.77) | 99.2 | >2 | — |
| N-(2-morpholinoethyl)-4,5-dihydronaphtho[1,2-b]thiophene-2-carboxamide | I | L (2.268) | 100 | >2 | — |
| N-(2-(piperidin-1-yl)ethyl)-4,5-dihydronaphtho[1,2-b]thiophene-2-carboxamide | I | L (2.007) | 100 | ** | * |
| N-propyl-4,5-dihydronaphtho[1,2-b]thiophene-2-carboxamide | I | L (2.84) | 100 | *** | ** |
| N-butyl-4,5-dihydronaphtho[1,2-b]thiophene-2-carboxamide | I | L (3.105) | 100 | ** | — |
| N-ethyl-4,5-dihydronaphtho[1,2-b]thiophene-2-carboxamide | I | L (2.588) | 99.1 | ** | — |
| 4,5-dihydronaphtho[1,2-b]thiophene-2-carboxamide | I | L (2.138) | 100 | **** | **** |
| 4H-thieno[3,2-c]chromene-2-carboxylic acid | A, J | L (1.188) | 100 | * | — |
| 8-fluoro-4H-thieno[3,2-c]chromene-2-carboxylic acid | A, J | L (1.255) | 100 | ** | — |
| 5-methyl-4,5-dihydronaphtho[1,2-b]thiophene-2-carboxylic acid | B | L (1.505) | 98.7 | ** | **** |
| 4H-thieno[3,2-c]chromene-2-carboxamide | I | L (1.903) | 100 | **** | **** |
| 6-cyano-4,5-dihydronaphtho[1,2-b]thiophene-2-carboxamide | I | L (1.92) | 97.7 | ** | **** |
| 5-methyl-4,5-dihydronaphtho[1,2-b]thiophene-2-carboxamide | I | L (2.348) | 99.4 | **** | **** |
| 8-fluoro-4H-thieno[3,2-c]chromene-2-carboxamide | I | L (2.02) | 100 | **** | **** |
| 5,5-dimethyl-4,5-dihydronaphtho[1,2-b]thiophene-2-carboxylic acid | B | L (1.635) | 100 | ** | — |
| ethyl 8-fluoro-4-methyl-4H-thieno[3,2-c]chromene-2-carboxylate | B | L (3.68) | 100 | >2 | — |
| 8-fluoro-4-methyl-4H-thieno[3,2-c]chromene-2-carboxylic acid | B | L (1.407) | 100 | ** | — |
| 4,4-dimethyl-4H-thieno[3,2-c]chromene-2-carboxylic acid | B | L (1.462) | 100 | >2 | — |
| 8-chloro-4H-thieno[3,2-c]chromene-2-carboxylic acid | B | L (1.488) | 99.1 | ** | **** |
| 8-fluoro-4-methyl-4H-thieno[3,2-c]chromene-2-carboxamide | I | L (2.237) | 100 | *** | **** |
| 5,5-dimethyl-4,5-dihydronaphtho[1,2-b]thiophene-2-carboxamide | I | L (2.525) | 100 | **** | **** |
| 8-chloro-4H-thieno[3,2-c]chromene-2-carboxamide | I | L (2.292) | 100 | ** | — |
| 8-methoxy-4H-thieno[3,2-c]chromene-2-carboxylic acid | A | A (1.502) | 100 | >2 | — |
| 6,8-dichloro-4H-thieno[3,2-c]chromene-2-carboxylic acid | A | A (1.788) | 99.6 | **** | **** |
| 7-(trifluoromethyl)-4H-thieno[3,2-c]chromene-2-carboxylic acid | A | A (1.39) | 99.6 | ** | **** |
| 1-(7-chloro-6-fluoro-4H-thieno[3,2-c]chromene-2-carbonyl)pyrrolidine-3-carbonitrile | I | A (2.01) | 99.7 | ** | **** |

TABLE 1-continued

| Compound | Prep | HPLC Method & Time (min) | Purity (%) | $IC_{50}$ | $EC_{50}$ |
|---|---|---|---|---|---|
| methyl 1-(7-chloro-6-fluoro-4H-thieno[3,2-c]chromene-2-carbonyl)-4-(2-fluorophenyl)pyrrolidine-3-carboxylate | I | A (2.413) | 100 | *** | **** |
| 1-(7-chloro-6-fluoro-4H-thieno[3,2-c]chromene-2-carbonyl)-4-(2-methoxyphenyl)pyrrolidine-3-carboxylic acid | I | A (1.715) | 96 | ** | **** |
| 7-chloro-6-fluoro-N-(2-morpholinoethyl)-4H-thieno[3,2-c]chromene-2-carboxamide | I | A (1.84) | 100 | >2 | ** |
| 7-chloro-6-fluoro-N-(2-methoxy-2-methylpropyl)-4H-thieno[3,2-c]chromene-2-carboxamide | I | A (2.16) | 99.6 | >2 | ** |
| 1-(7-chloro-6-fluoro-4H-thieno[3,2-c]chromene-2-carbonyl)-4-(thiophen-2-yl)pyrrolidine-3-carboxylic acid | I | A (1.585) | 99.5 | ** | **** |
| 6,7-difluoro-N-(pyridin-2-ylmethyl)-4,5-dihydronaphtho[1,2-b]thiophene-2-carboxamide | I | A (2.005) | 99 | **** | **** |
| ethyl 6,8-dimethyl-4,5-dihydronaphtho[1,2-b]thiophene-2-carboxylate | B | K (2.52) | 99.5 | * | *** |
| 6,8-dimethyl-4,5-dihydronaphtho[1,2-b]thiophene-2-carboxylic acid | B | B (4.13) | 98.5 | **** | **** |
| 6,8-dimethyl-4,5-dihydronaphtho[1,2-b]thiophene-2-carboxamide | I | C (1.95) | 99.6 | ** | **** |
| methyl 2-(6,8-dimethyl-4,5-dihydronaphtho[1,2-b]thiophene-2-carboxamido)acetate | I | D (1.73) | 99.3 | * | *** |
| 2-(6,8-dimethyl-4,5-dihydronaphtho[1,2-b]thiophene-2-carboxamido)acetic acid | J | E (2.14) | 98.1 | ** | *** |
| ethyl 6-fluoro-8-methyl-4,5-dihydronaphtho[1,2-b]thiophene-2-carboxylate | U, V, B | D (2.14) | 98.8 | ** | **** |
| ethyl 6-chloro-7-methyl-4,5-dihydronaphtho[1,2-b]thiophene-2-carboxylate | B | D (2.26) | 94.7 | ** | **** |
| 6-fluoro-8-methyl-4,5-dihydronaphtho[1,2-b]thiophene-2-carboxylic acid | B | E (2.37) | 100 | **** | **** |
| 6-chloro-7-methyl-4,5-dihydronaphtho[1,2-b]thiophene-2-carboxylic acid | B | D (1.29) | 95.3 | *** | **** |
| ethyl 7-methyl-6-nitro-4,5-dihydronaphtho[1,2-b]thiophene-2-carboxylate | B | D (2.04) | 97.6 | *** | **** |
| 6-chloro-7-methyl-4,5-dihydronaphtho[1,2-b]thiophene-2-carboxamide | I | D (1.7) | 99.3 | **** | **** |
| 6-fluoro-8-methyl-4,5-dihydronaphtho[1,2-b]thiophene-2-carboxamide | I | D (1.56) | 99.4 | **** | **** |
| 7-methyl-6-nitro-4,5-dihydronaphtho[1,2-b]thiophene-2-carboxylic acid | B | D (1.15) | 98.5 | **** | **** |
| methyl 1-(6-fluoro-8-methyl-4,5-dihydronaphtho[1,2-b]thiophene-2-carbonyl)-4-phenylpyrrolidine-3-carboxylate | I | D (2.01) | 97.4 | ** | **** |
| ethyl 6-cyano-7-methyl-4,5-dihydronaphtho[1,2-b]thiophene-2-carboxylate | B, W, X | D (1.98) | 99.2 | **** | **** |
| ethyl 6-fluoro-7-methyl-4,5-dihydronaphtho[1,2-b]thiophene-2-carboxylate | U, V, B | D (2.15) | 98.8 | ** | — |
| 6-fluoro-7-methyl-4,5-dihydronaphtho[1,2-b]thiophene-2-carboxylic acid | B | E (2.38) | 99.4 | *** | **** |
| 6-fluoro-7-methyl-4,5-dihydronaphtho[1,2-b]thiophene-2-carboxamide | I | D (1.56) | 98.1 | **** | **** |

TABLE 1-continued

| Compound | Prep | HPLC Method & Time (min) | Purity (%) | IC$_{50}$ | EC$_{50}$ |
|---|---|---|---|---|---|
| N-(cyanomethyl)-4,5-dihydronaphtho[1,2-b]thiophene-2-carboxamide | I | A (2.08) | 99.8 | **** | **** |
| 1-(4,5-dihydronaphtho[1,2-b]thiophene-2-carbonyl)pyrrolidine-2-carboxylic acid | I | A (1.47) | 99.4 | >2 | — |
| methyl 2-(4,5-dihydronaphtho[1,2-b]thiophene-2-carboxamido)acetate | I | A (2.08) | 98 | ** | **** |
| N-(2-cyanopropan-2-yl)-4,5-dihydronaphtho[1,2-b]thiophene-2-carboxamide | I | A (2.23) | 95.3 | ** | ** |
| 2-(4,5-dihydronaphtho[1,2-b]thiophene-2-carboxamido)acetic acid | I | A (1.45) | 99.9 | *** | **** |
| (4,5-dihydronaphtho[1,2-b]thiophene-2-carbonyl)sulfamic acid | I | K (1.58) | 99.1 | * | — |
| N-(methylsulfonyl)-4,5-dihydronaphtho[1,2-b]thiophene-2-carboxamide | I | K (1.58) | 99.7 | >2 | — |
| 5,6-dihydro-4H-benzo[6,7]cyclohepta[1,2-b]thiophene-2-carboxylic acid | B | K (1.65) | 97.9 | ** | — |
| 9-fluoro-5,6-dihydro-4H-benzo[6,7]cyclohepta[1,2-b]thiophene-2-carboxylic acid | B | K (1.69) | 99.5 | ** | — |
| 5,6-dihydro-4H-benzo[6,7]cyclohepta[1,2-b]thiophene-2-carboxamide | I | K (2.09) | 98.5 | **** | **** |
| 9-fluoro-5,6-dihydro-4H-benzo[6,7]cyclohepta[1,2-b]thiophene-2-carboxamide | I | K (2.11) | 100 | *** | **** |
| 4,5-dihydrobenzo[b]thieno[2,3-d]oxepine-2-carboxamide | I | K (1.91) | 100 | **** | **** |
| 5-acetyl-4,5-dihydrothieno[3,2-c]quinoline-2-carboxylic acid | A | K (1.4) | 100 | * | *** |
| 4,5-dihydrobenzo[b]thieno[2,3-d]oxepine-2-carboxylic acid | A | K (1.49) | 95.8 | ** | **** |
| N-(2-hydroxyethyl)-5,6-dihydro-4H-benzo[6,7]cyclohepta[1,2-b]thiophene-2-carboxamide | I | K (2) | 96.7 | ** | *** |
| N-(2-methoxyethyl)-5,6-dihydro-4H-benzo[6,7]cyclohepta[1,2-b]thiophene-2-carboxamide | I | K (2.25) | 99.8 | >2 | ** |
| 9-chloro-4,5-dihydrobenzo[b]thieno[2,3-d]oxepine-2-carboxylic acid | A | K (1.66) | 99.8 | ** | *** |
| 9-chloro-4,5-dihydrobenzo[b]thieno[2,3-d]oxepine-2-carboxamide | I | K (2.07) | 97.6 | ** | *** |
| 9-fluoro-4,5-dihydrobenzo[b]thieno[2,3-d]oxepine-2-carboxylic acid | A | K (1.56) | 97.6 | ** | **** |
| 9-fluoro-4,5-dihydrobenzo[b]thieno[2,3-d]oxepine-2-carboxamide | I | K (1.94) | 98.1 | *** | **** |
| 9-fluoro-N-(2-methoxyethyl)-4,5-dihydrobenzo[b]thieno[2,3-d]oxepine-2-carboxamide | I | K (2.11) | 96.4 | >2 | ** |
| 7-chloro-8-fluoro-4H-thieno[3,2-c]thiochromene-2-carboxylic acid | G, C | K (1.74) | 100 | *** | **** |
| 6,8-dichloro-4H-thieno[3,2-c]thiochromene-2-carboxylic acid | G, C | K (1.68) | 95.1 | ** | **** |
| 7-chloro-8-fluoro-4H-thieno[3,2-c]thiochromene-2-carboxamide | I | K (2.06) | 97.2 | *** | **** |
| 6,8-dichloro-4H-thieno[3,2-c]thiochromene-2-carboxamide | I | K (2.17) | 97.5 | * | **** |
| 7-chloro-8-fluoro-4H-thieno[3,2-c]thiochromene-2-carboxylic acid 5,5-dioxide | G, C, L | K (1.36) | 96.8 | * | **** |
| 7,8-dichloro-4,5-dihydrobenzo[b]thieno[2,3-d]oxepine-2-carboxylic acid | A | J (1.79) | 96.6 | ** | **** |
| 7,8-dichloro-4,5-dihydrobenzo[b]thieno[2,3-d]oxepine-2-carboxamide | I | K (2.04) | 95.8 | * | **** |
| 6,8-difluoro-4H-thieno[3,2-c]thiochromene-2-carboxylic acid | C, G | I (2.31) | 99.7 | **** | **** |

TABLE 1-continued

| Compound | Prep | HPLC Method & Time (min) | Purity (%) | IC$_{50}$ | EC$_{50}$ |
|---|---|---|---|---|---|
| 6,8-difluoro-4H-thieno[3,2-c]thiochromene-2-carboxamide | I | H (2.05) | 98.4 | **** | **** |
| 6,8-difluoro-4H-thieno[3,2-c]thiochromene-2-carboxylic acid 5,5-dioxide | C, G, L | H (1.27) | 99 | ** | ** |
| 6-chloro-4H-thieno[3,2-c]thiochromene-2-carboxylic acid | C, G | H (1.77) | 99 | * | **** |
| 6,8-difluoro-4H-thieno[3,2-c]thiochromene-2-carboxylic acid 5-oxide | C, G, K | H (0.93) | 92.3 | >2 | ** |
| 6-chloro-4H-thieno[3,2-c]thiochromene-2-carboxamide | I | H (1.83) | 97.1 | ** | **** |
| 4,5-dihydrobenzo[b]thieno[2,3-d]thiepine-2-carboxylic acid | C, G | H (1.42) | 96.8 | >2 | *** |
| 4,5-dihydrobenzo[b]thieno[2,3-d]thiepine-2-carboxamide | I | H (1.72) | 97.7 | *** | **** |
| 6,7-dichloro-4H-thieno[3,2-c]thiochromene-2-carboxylic acid | C, G | H (1.48) | 98.8 | *** | **** |
| 6,9-difluoro-4H-thieno[3,2-c]thiochromene-2-carboxylic acid | C, G | H (1.3) | 99.5 | **** | **** |
| 6,9-difluoro-4H-thieno[3,2-c]thiochromene-2-carboxamide | I | H (1.73) | 99.7 | **** | **** |
| 6,7-dichloro-4H-thieno[3,2-c]thiochromene-2-carboxamide | I | H (2.03) | 96.5 | *** | **** |
| 4,5-dihydrobenzo[b]thieno[2,3-d]thiepine-2-carboxylic acid 6,6-dioxide | B, L | H (0.97) | 100 | >2 | * |
| methyl 1-(6,8-difluoro-4H-thieno[3,2-c]thiochromene-2-carbonyl)pyrrolidine-3-carboxylate | I | H (2.07) | 97.9 | ** | **** |
| 1-(6,8-difluoro-4H-thieno[3,2-c]thiochromene-2-carbonyl)pyrrolidine-3-carboxylic acid | I | H (1.37) | 97.5 | ** | **** |
| 7-chloro-6-fluoro-4H-thieno[3,2-c]thiochromene-2-carboxylic acid | C, G | H (1.4) | 98.1 | **** | **** |
| ethyl 7-chloro-6-fluoro-4H-thieno[3,2-c]thiochromene-2-carboxylate | C, G | H (2.64) | 98.3 | ** | *** |
| 7-chloro-6-fluoro-4H-thieno[3,2-c]thiochromene-2-carboxamide | I | H (1.91) | 96.2 | **** | **** |
| (6,8-difluoro-4H-thieno[3,2-c]thiochromen-2-yl)(2-(hydroxymethyl)pyrrolidin-1-yl)methanone | I | H (1.92) | 96.7 | ** | *** |
| (6,8-difluoro-4H-thieno[3,2-c]thiochromen-2-yl)(3-hydroxypyrrolidin-1-yl)methanone | I | H (1.74) | 97.1 | *** | **** |
| (6,8-difluoro-4H-thieno[3,2-c]thiochromen-2-yl)(3-hydroxypyrrolidin-1-yl)methanone | I | H (1.74) | 96.2 | **** | **** |
| 1-(6,8-difluoro-4H-thieno[3,2-c]thiochromene-2-carbonyl)pyrrolidin-3-one | I | H (1.93) | 95.5 | **** | **** |
| (6,8-difluoro-4H-thieno[3,2-c]thiochromen-2-yl)(3-methoxypyrrolidin-1-yl)methanone | I | H (2.06) | 96.7 | *** | **** |
| tert-butyl 2-(1-(6,8-difluoro-4H-thieno[3,2-c]thiochromene-2-carbonyl)pyrrolidin-2-yl)acetate | I | H (2.5) | 98.4 | >2 | — |
| (6,8-difluoro-4H-thieno[3,2-c]thiochromen-2-yl)(2-(methoxymethyl)pyrrolidin-1-yl)methanone | I | H (2.23) | 97.7 | >2 | — |
| 1-(6,8-difluoro-4H-thieno[3,2-c]thiochromene-2-carbonyl)pyrrolidine-2-carboxylic acid | I | H (1.34) | 100 | * | — |
| 1-(6,9-difluoro-4H-thieno[3,2-c]thiochromene-2-carbonyl)pyrrolidine-3-carboxylic acid | I | H (1.31) | 96.7 | *** | **** |
| 1-(6,9-difluoro-4H-thieno[3,2-c]thiochromene-2-carbonyl)pyrrolidine-2-carboxylic acid | I | H (1.29) | 94.7 | ** | — |
| 1-(6,9-difluoro-4H-thieno[3,2-c]thiochromene-2-carbonyl)-3-hydroxypyrrolidine-2-carboxylic acid | I | H (1.18) | 100 | >2 | — |
| 6-chloro-8-fluoro-4H-thieno[3,2-c]thiochromene-2-carboxylic acid | C, G | H (1.4) | 99.3 | **** | **** |

TABLE 1-continued

| Compound | Prep | HPLC Method & Time (min) | Purity (%) | IC$_{50}$ | EC$_{50}$ |
|---|---|---|---|---|---|
| ethyl 6-chloro-8-fluoro-4H-thieno[3,2-c]thiochromene-2-carboxylate | C, G | H (2.66) | 95.3 | >2 | — |
| 6-chloro-8-fluoro-4H-thieno[3,2-c]thiochromene-2-carboxamide | I | H (1.9) | 96.8 | *** | **** |
| 6,7,8-trifluoro-4H-thieno[3,2-c]thiochromene-2-carboxylic acid | C, G | H (1.41) | 96.8 | **** | **** |
| 6,7,8-trifluoro-4H-thieno[3,2-c]thiochromene-2-carboxamide | I | H (1.882) | 95 | **** | **** |
| (S)-(6,9-difluoro-4H-thieno[3,2-c]thiochromen-2-yl)(3-fluoropyrrolidin-1-yl)methanone | I | H (2.08) | 96.6 | *** | **** |
| (S)-(7-chloro-8-fluoro-4H-thieno[3,2-c]thiochromen-2-yl)(3-fluoropyrrolidin-1-yl)methanone | I | H (2.243) | 97.9 | ** | **** |
| (S)-(6,8-difluoro-4H-thieno[3,2-c]thiochromen-2-yl)(3-fluoropyrrolidin-1-yl)methanone | I | H (2.09) | 96.8 | ** | **** |
| 8-fluoro-6-methyl-4H-thieno[3,2-c]thiochromene-2-carboxylic acid | C, G | H (1.405) | 97.7 | ** | **** |
| 8-fluoro-7-methyl-4H-thieno[3,2-c]thiochromene-2-carboxylic acid | C, G | H (1.403) | 98.7 | *** | **** |
| 5,6-dihydro-4H-benzo[6,7]cyclohepta[1,2-b]thiophene-2-carboxylic acid | B | K (1.647) | 97.7 | — | * |
| 9-fluoro-5,6-dihydro-4H-benzo[6,7]cyclohepta[1,2-b]thiophene-2-carboxylic acid | B | K (1.69) | 99.5 | — | * |
| 5,6-dihydro-4H-benzo[6,7]cyclohepta[1,2-b]thiophene-2-carboxamide | I | K (2.087) | 98.5 | **** | **** |
| 9-fluoro-5,6-dihydro-4H-benzo[6,7]cyclohepta[1,2-b]thiophene-2-carboxamide | I | K (2.112) | 100 | **** | *** |
| 4,5-dihydrobenzo[b]thieno[2,3-d]oxepine-2-carboxamide | A, I | K (1.91) | 100 | **** | **** |
| 4,5-dihydrobenzo[b]thieno[2,3-d]oxepine-2-carboxylic acid | A | K (1.487) | 95.8 | **** | * |
| N-(2-hydroxyethyl)-5,6-dihydro-4H-benzo[6,7]cyclohepta[1,2-b]thiophene-2-carboxamide | I | K (1.995) | 96.7 | *** | * |
| 9-chloro-4,5-dihydrobenzo[b]thieno[2,3-d]oxepine-2-carboxylic acid | A | K (1.652) | 100 | *** | * |
| 9-chloro-4,5-dihydrobenzo[b]thieno[2,3-d]oxepine-2-carboxamide | A, I | K (2.072) | 97.6 | *** | * |
| 9-fluoro-4,5-dihydrobenzo[b]thieno[2,3-d]oxepine-2-carboxylic acid | A | K (1.558) | 97.6 | **** | ** |
| 9-fluoro-4,5-dihydrobenzo[b]thieno[2,3-d]oxepine-2-carboxamide | I | K (1.935) | 98.1 | **** | *** |
| 7,8-dichloro-4,5-dihydrobenzo[b]thieno[2,3-d]oxepine-2-carboxylic acid | AB, A | G (1.788) | 96.6 | **** | * |
| 4,5-dihydrobenzo[b]thieno[2,3-d]thiepine-2-carboxamide | AB, I | H (1.718) | 97.9 | **** | *** |
| 4,5-dihydrobenzo[1,2-b:3,4-b']dithiophene-2-carboxylic acid | B | H (1.205) | 95.6 | **** | ** |
| 4,5-dihydrobenzo[1,2-b:3,4-b']dithiophene-2-carboxamide | I | H (1.628) | 96 | **** | **** |
| 4,5-dihydrobenzo[1,2-b:6,5-b']dithiophene-2-carboxylic acid | B | H (1.293) | 97.9 | — | * |
| 7-chloro-4,5-dihydrobenzo[1,2-b:6,5-b']dithiophene-2-carboxylic acid | AC | H (1.408) | 97.5 | **** | ** |
| 8-chlorobenzo[1,2-b:3,4-b']dithiophene-2-carboxylic acid | AC | H (1.478) | 99.1 | **** | * |
| 4,5-dihydrothieno[2,3-e]benzofuran-2-carboxylic acid | B | H (1.11) | 99.3 | — | >1 |
| 4,5-dihydrothieno[2',3':3,4]benzo[1,2-d]thiazole-7-carboxylic acid | B | H (0.965) | 99.5 | — | >1 |

6.35. Pharmacology of 6,9-difluoro-4H-thieno[3,2-c]thiochromene-2-carboxylic acid

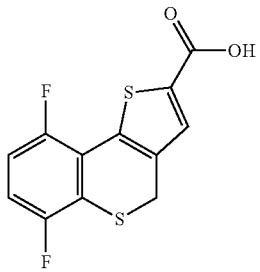 [SMILES: O=C(O)c1cc2c(s1)-c1c(F)ccc(F)c1SC2]

Figure 5:
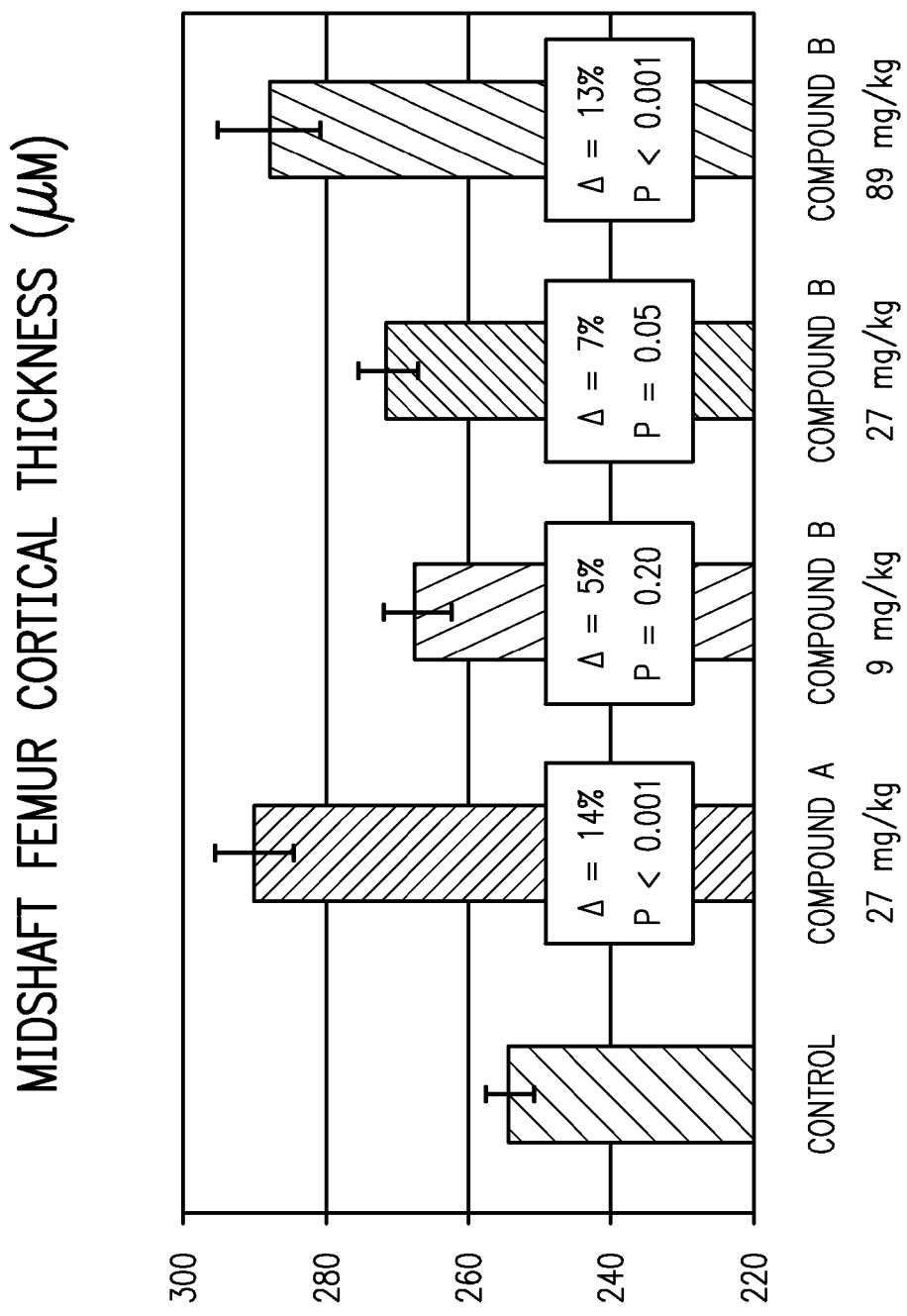

FIG. 5 shows the in vivo effect of 6,9-difluoro-4H-thieno[3,2-c]thiochromene-2-carboxylic acid ("Compound B") as compared to control and the NOTUM inhibitor 2-((5-chloro-6-methylthieno[2,3-d]pyrimidin-4-yl)thio)acetic acid ("Compound A"). The effect was determined by treating F1 male hybrid (129×C57) mice for 28 days with the compounds, starting at 9.7 weeks of age. The compounds were administered in the animals' diet. Five groups of mice were used: control (N=16); 27 mg/kg Compound A (N=12); 9 mg/kg Compound B (N=12); 27 mg/kg Compound B (N=12); and 89 mg/kg Compound B (N=12). Mice treated with Compound B exhibited a 14% (p<0.001) increase in midshaft femur cortical thickness.

6.36. Pharmacology of 4H-thieno[3,2-c]thiochromene-2-carboxylic acid 5,5-dioxide

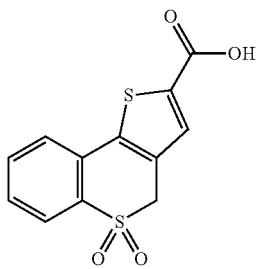 [SMILES: O=C(O)c1cc2c(s1)-c1ccccc1S(=O)(=O)C2]

Figure 6:
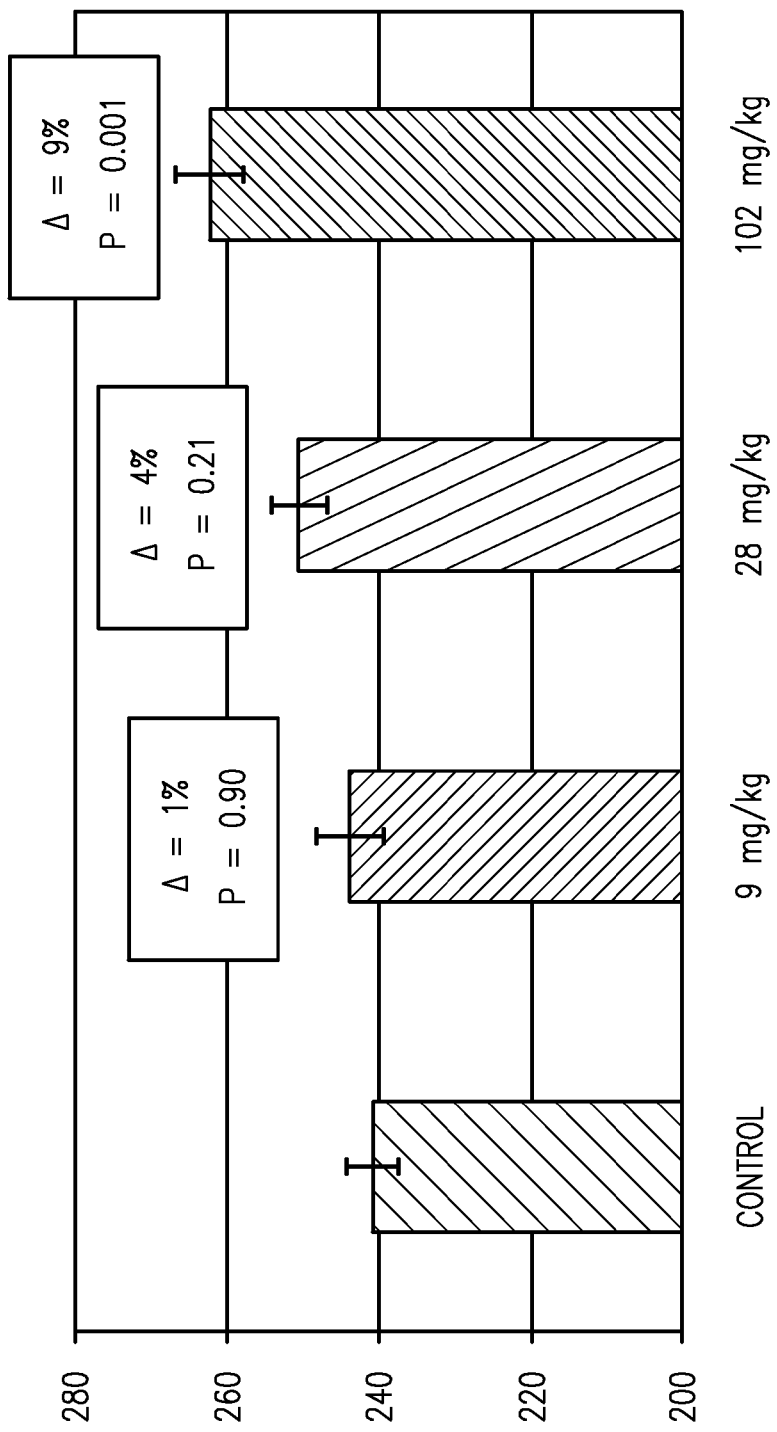
FIG. 6 shows the effects of administering 4H-thieno[3,2-c]thiochromene-2-carboxylic acid 5,5-dioxide on the midshaft femur cortical thickness of mice.

The in vivo effect of 4H-thieno[3,2-c]thiochromene-2-carboxylic acid 5,5-dioxide was determined by treating F1 male hybrid (129×C57) mice for 26 days with the compound, starting at 8.3 weeks of age. The compound was administered in the animals' diet. Four groups of mice were used: control (N=12); 9 mg/kg compound (N=12); 28 mg/kg compound (N=12); and 102 mg/kg compound (N=12). As shown in FIG. 6, mice treated with 102 mg/kg exhibited a 9% (p<0.001) increase in midshaft femur cortical thickness.

6.37. Pharmacology of 6,8-difluoro-4H-thieno[3,2-c]thiochromene-2-carboxylic acid

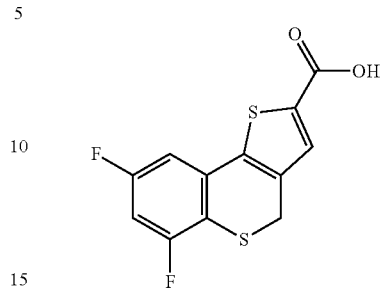

Figure 7:
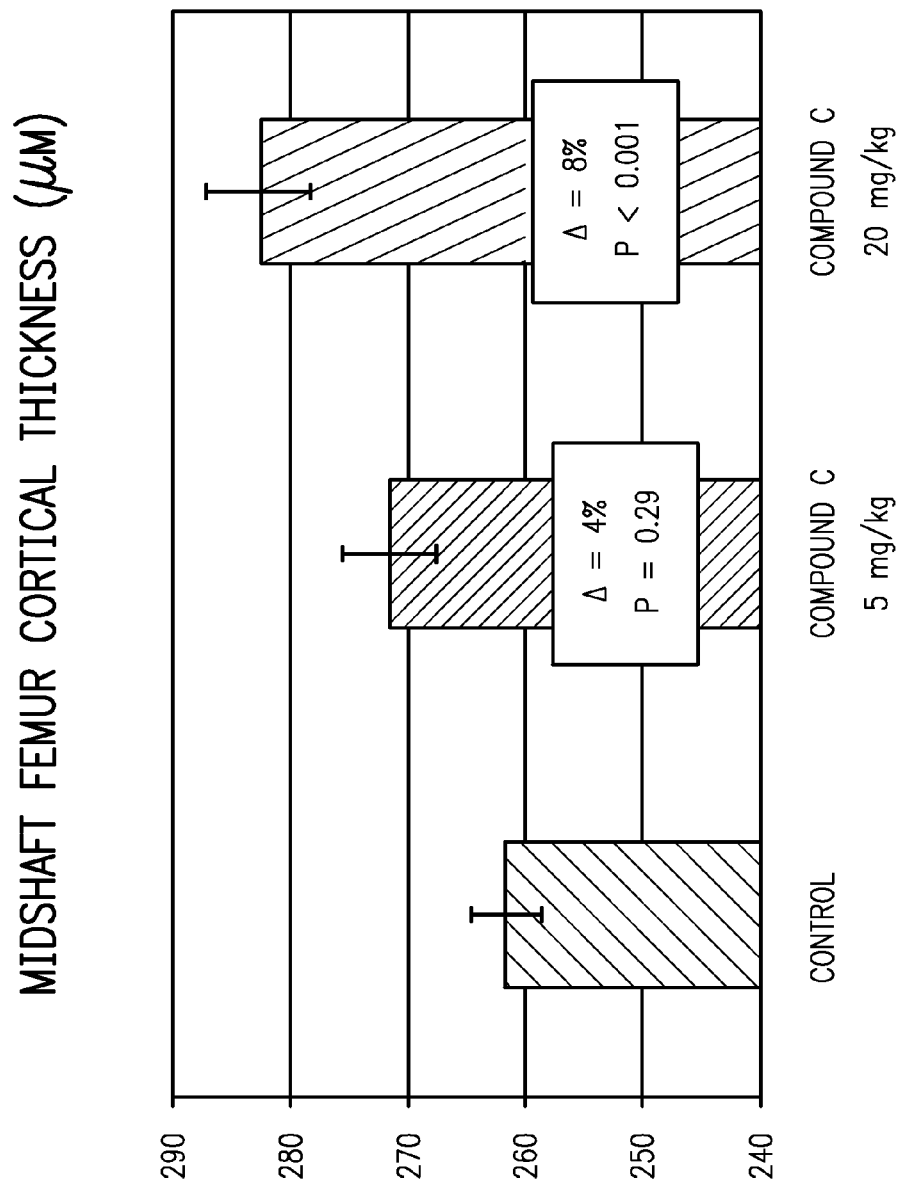
FIG. 7 shows the effects of administering 6,8-difluoro-4H-thieno[3,2-c]thiochromene-2-carboxylic acid on the midshaft femur cortical thickness of mice.

FIG. 7 shows the in vivo effect of 6,8-difluoro-4H-thieno[3,2-c]thiochromene-2-carboxylic acid ("Compound C"). The effect was determined by treating F1 male hybrid (129×C57) mice for 28 days with the compound, starting at 10.5 weeks of age. The compound was administered in the animals' diet. Three groups of mice were used: control (N=15); 5 mg/kg compound (N=12); and 21 mg/kg compound (N=12). Mice treated with the compound exhibited dose-dependent increases in midshaft femur cortical thickness.

All references (e.g., patents and published patent applications) cited above are incorporated herein by reference.

What is claimed is:
1. A compound of the formula:

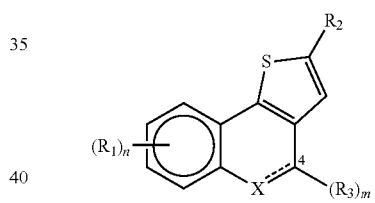

or a pharmaceutically acceptable salt thereof, wherein:
X is S, S(O), or S(O)$_2$;
each $R_1$ is independently $R_{1A}$ or alkyl or heteroalkyl optionally substituted with one or more $R_{1A}$;
each $R_{1A}$ is independently alkoxyl, amido, amino, carbamide, carboxyl, cyano, halo, hydroxyl, nitro, sulfanyl, sulfinyl, sulfonyl, or thio;
n is 0-4;
$R_2$ is —C(O)$R_{2A}$ or 5- or 6-membered cycloalkyl or heterocycle optionally substituted with one or more $R_{2B}$;
$R_{2A}$ is —O$R_{2C}$, —N($R_{2C}$)$_2$, —C($R_{2C}$)$_2$NO$_2$, —C($R_{2C}$)$_2$O$R_{2C}$, —C($R_{2C}$)$_2$CN, or aryl or 5- or 6-membered heterocycle optionally substituted with one or more $R_{2B}$;
each $R_{2B}$ is independently alkoxyl, amido, amino, carboxamide, carboxyl, cyano, halo, hydroxyl, nitro, sulfanyl, sulfinyl, sulfonyl, or thio;
each $R_{2C}$ is independently hydrogen, alkyl, aryl, heteroalkyl, or 5- or 6-membered heterocycle;
m is 0-2;
when m is 1, $R_3$ is H or $C_{1-2}$-alkyl;
when m is 2, one of $R_3$ is $C_{1-2}$-alkyl or cycloalkyl, and the other $R_3$ is H or $C_{1-2}$-alkyl; and
each $R_4$ is independently H, fluoro or $C_{1-2}$-alkyl.

2. The compound of claim 1, wherein at least one $R_4$ is H.

3. The compound of claim 1, wherein at least one $R_1$ is $R_{1A}$.

4. The compound of claim 1, wherein $R_{1A}$ is halo.

5. The compound of claim 1, wherein $R_{1A}$ is cyano.

6. The compound of claim 1, wherein $R_{1A}$ is nitro.

7. The compound of claim 1, wherein $R_2$ is C(O)OH.

8. The compound of claim 1, wherein $R_{2A}$ is $-OR_{2C}$, $-N(R_{2C})_2$, $-CH_2NO_2$, $-CH_2OR_{2C}$, or $-CH_2CN$.

9. The compound of claim 1, wherein n is 2.

10. The compound of claim 1, wherein n is 3.

11. The compound of claim 1, wherein m is 0.

12. The compound of claim 1, wherein m is 1 and $R_3$ is methyl.

13. A formulation comprising a compound of claim 1 and a pharmaceutically acceptable excipient.

\* \* \* \* \*